(12) United States Patent
Aceña et al.

(10) Patent No.: US 7,138,547 B2
(45) Date of Patent: Nov. 21, 2006

(54) ANTITUMORAL COMPOUNDS

(75) Inventors: Jose Luis Aceña, Madrid (ES); Javier Adrio, Madrid (ES); Carmen Cuevas, Madrid (ES); Pilar Gallego, Madrid (ES); Ignacio Manzanares, Madrid (ES); Simon Munt, Madrid (ES); Ignacio Rodriguez, Madrid (ES)

(73) Assignee: Pharma Mar, S.A., Madrid ( * ) Notice: Subject to any disclaimer, the term of this patent is extended or adjusted under 35 U.S.C. 154(b) by 75 days.

(21) Appl. No.: 10/297,352

(22) PCT Filed: Jun. 6, 2001

(86) PCT No.: PCT/GB01/02487

§ 371 (c)(1),
(2), (4) Date: Aug. 18, 2003

(87) PCT Pub. No.: WO01/94357

PCT Pub. Date: Dec. 13, 2001

(65) Prior Publication Data

US 2004/0048834 A1 Mar. 11, 2004

(30) Foreign Application Priority Data

Jun. 6, 2000 (GB) .................................. 0013783.6
Jan. 31, 2001 (GB) .................................. 0102472.8
Feb. 26, 2001 (GB) .................................. 0104732.3

(51) Int. Cl.
C07C 233/00 (2006.01)
C07D 493/00 (2006.01)
A61K 31/42 (2006.01)
A61K 31/35 (2006.01)

(52) U.S. Cl. ...................... 564/219; 549/239; 514/376; 514/459

(58) Field of Classification Search ................ 564/219, 564/223, 360, 468, 503, 507, 509; 549/239, 549/530; 514/376, 459, 625, 629, 630
See application file for complete search history.

(56) References Cited

U.S. PATENT DOCUMENTS 2,346,771 A 4/1944 Lodge et al.
(Continued)

FOREIGN PATENT DOCUMENTS

DE 828 547 1/1952
(Continued)

OTHER PUBLICATIONS

Alaupovik et al., "Necrosamine Series II. Synthesis of Racemic 4,5-Diaminoeicosane and of 2-Methyl-3,4-Diaminononadecane", *Croatica Chemica Acta*, 28:211-218 (1956).
(Continued)

Primary Examiner—Deborah C. Lambkin
(74) Attorney, Agent, or Firm—Fish & Richardson P.C.

(57) ABSTRACT

New spisulosine derivatives of use in treating tumors are of the formula (I) wherein: each X is the same or different, and represents H, OH, OR', SH, SR', SOR', $SO_2R'$, $NO_2$, $NH_2$, NHR', $N(R')_2$, CN, halogen, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, or two groups X may together form =O; Y is $NR_1$, $OR_1$, $PR_1$, $SR_1$, or halogen, wherein the number of substituents $R_1$ is selected to suit the valency and each $R_1$ is independently selected of H, OH, C(=O)R', P(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, and wherein the dotted line indicates an optional double bond; each Z is the same different, and represents H, OH, OR', SH, SR', SOR', $SO_2R'$, $NO_2$, $NH_2$, NHR', $N(R')_2$, NHC(O)R', CN, halogen, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, or two groups Z may together form =O; z is 0 to 25; y is to 0 to 20; $R_2$ is H, C(=O)R', P(=O)R'R", S(=O)R'R", $S(=O)_2R'$, substituted or unsubstituted $C_1$–$C_{18}$ alkyl, substituted or unsubstituted $C_2$–$C_{18}$ Alkenyl, substituted or unsubstituted $C_2$–$C_{18}$ alkynyl, substituted or unsubstituted aryl; $R_3$ is H, C(=O)R', P(=O)R'R", S(=O)R'R", $S(=O)_2R'$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl; each of the R', R" groups is independently selected from the group consisting of H, OH, $NO_2$, $NH_2$, SH, CN, halogen, =O, C(=O)H, C(=O)$CH_3$, $CO_2H$, $CO_{2,CH_3}$, substituted or unsubstituted $C_1$–$C_{18}$ alkyl, substituted or unsubstituted $C_1$–$C_{18}$ alkoxy, substituted or unsubstituted $C_2$–$C_{18}$ alkenyl, substituted or unsubstituted $C_2$–$C_{18}$ alkynl, substituted or unsubstituted aryl; there may be one or more unsaturations in the hydrocarbon backbone defined by the chain (II) and salts thereof; with the exception of a $C_{16}$–$C_{24}$ 2-amino-3-hydroxyalkane or a $C_{16}$–$C_{24}$ 2-amino-3-hydroxyalkene

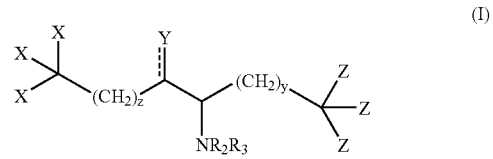

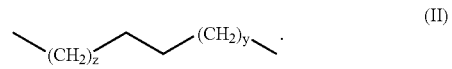

13 Claims, No Drawings

U.S. PATENT DOCUMENTS

| | | | |
|---|---|---|---|
| 2,363,082 | A | 11/1944 | Ringk |
| 2,399,118 | A | 4/1946 | Homeyer |
| 2,424,311 | A | 7/1947 | Harris |
| 6,107,520 | A * | 8/2000 | Rinehart et al. ............ 564/360 |
| 6,756,504 | B1 * | 6/2004 | Dagan et al. ................. 554/52 |
| 6,800,661 | B1 * | 10/2004 | Rinehart et al. ............ 514/667 |
| 6,835,831 | B1 * | 12/2004 | Hirth .......................... 540/607 |
| 6,852,892 | B1 * | 2/2005 | Van Boom et al. ......... 564/503 |
| 6,881,546 | B1 * | 4/2005 | Sabbadini ................... 435/7.1 |
| 6,888,015 | B1 * | 5/2005 | Kobayashi et al. ........... 554/66 |

FOREIGN PATENT DOCUMENTS

| | | |
|---|---|---|
| GB | 1 057 652 | 2/1967 |
| GB | 1 433 920 | 4/1976 |
| WO | WO 99/52521 | 10/1999 |

OTHER PUBLICATIONS

Claus, "Zur Kenntnis der Birbrombernsteinsaeure aus der Diamidobernsteinsaeure", *Berichte der Deutschen Chemischen Gesellschaft*, 15:1844-1851 (1882).

Cuadros et al., "The Marine Compound Spisulosine and Inhibitor of Cell Proliferation, Promotes the Disassembly of Actin Stress Fibers", *Cancer Letters*, 152(2):23-29 (2000).

Garrido et al., "Obscuraminols, New Unsaturated Amino Alcohols from the Tunicate Pseudodistoma Obscurum: Structure and Absolute Configuration", *Tetrahedron*, 57(21):4579-4588 (2001).

Gerencevik et al., "N-Acyl Amino Acids in the Dakin-West Reaction: Replacements of the acyl Groups", *Bulletin Scientifique, Conseil des Academies des Sciences et des Arts de la RSF de Yougoslavie, Section A: Sciences Naturelles, Techniques et Medicales*, 15(5-6):158 (1970).

Ikawa, "Studies on a Lipopolysaccharide from *Escherichai coli*", *Annals of the New York Academy of Sciences*, 133(2):476-485 (1966).

Jaenecke, "Ueber Amidodiaethylketon und Amidodiaethylcarbinol", *Berichte der Deutschen Chemischen Gesellschaft*, 32:1095-1103 (1899).

Jares-Erijman et al., "Crucigasterins, New Polyunsaturated Amino Alcohols from the Mediterranean Tunicate Pseudodistoma Crucigaster", *Journal of Organic Chemistry*, 58(21):5732-5737 (1993).

Jimenez et al., "Novel Marine Sponge Amino Acids, 10. Xestoaminols from Xestospongia Sp", *Journal of Natural Products*, 53(4):978-982 (1990).

Koehl, "Ueber Die Beta, Beta-Diaminoadiponsaeure und Eine Neue Methode zur Darstelling von Gama-Aminosaeuren", *Berichte der Deutschen Chemischen Gesellschaft*, 36:172-174, (1903).

Kok et al., "Dihydrocermide Biology Structure-Specific Metabolism and Intracellular Localization", *Journal of Biological Chemistry*, 272(34):2428-2436 (1997).

Mori et al., "Synthesis and Absolute Configuration of the Two Epimeric Aliphatic Amino Alcohols '(5E, 7E)-2-amino-5,7-tetradecadien-3-ols! Isolated from a Sponge, Xestospogia sp.", *Liebigs Annalen der Chemie*, 2:131-137 (1992).

Palameta et al., "Chromatography of the Lipide Based on Paper Impregnated with Silicic Acid", *Croatica Chemica Acta*, 33:133-135 (1961).

Poch et al., "Relative Stereochemistry of Funomisin B1 and C-2 and C-3", *Tetrahedron Letters*, 35(42):7707-7710 (1994).

Prostenik et al., "Application of the Asymmetric Synthesis in the Determination of the Configuration of Amino Alcohols and Diamines with Two Adjacent Asymmetric Carbon Atoms", *Croatica Chemica Acta*, 29:393-402 (1957).

Prostenik et al., "Necrosaminreihe, 6 Mitteilung: Uber Eine Einfache Synthese von Racemischem necrosamin", *Bulletin Scientifique, Conseil Academies Des Sciences Et Des Arts De La RSF De Yougoslavie, Section A: Sciences Naturelles, Techniques Et Medicales*, 17(5-6):145-146 (1972).

Prostenik et al., "Synthetische Versuche in der Necrosamin-Reihe", *Naturwissenschaften*, 43:349-350 (1956).

Prostenik et al., "Ueber Eine Einfache Synthese Von Aliphatischen Alpha-Diaminen", *Monatschefie Fur Chemie*, 97(2):340-347 (1966).

Rao et al, "Isolation and Constitution of Pedicellic Acid a New Dicarboxylic Acid From the Leaves of Didymocarpus Pedicellata", *Tetrahedron*, 22(4):1495-1498 (1966).

Salako et al., "99mTC-Labelling Studies of Solubilized Ligands—Part 1", *International Journal of Radiation Applications and Instrumentation Part A: Applied Radiation and Isotopes*, 40(7):621-624 (1989).

Strauss, "Ueber Aminopropanol-(2,1) und Aminobutanol-(2.3)", *Berichte der Deutschen Chemischen Gesellschaft*, 33:2825-2830 (1900).

Turel et al., "Sphingolipids: Part II—Synthesis of 1, 3-Dihydroxy-2-Aminotetradecane", *Indian Journal of Chemistry*, 18B:219-221 (1979).

Leonardi. "Attivita'citolitica e citostatica della necrosamina sintetica (4,5-diaminoeicosano) su due ceppi di cellule tumorali umane coltivate in vitro", *Giornale Italiano di Chemio Terapia*, 5:291-295 (1958).

Leonardi, "Cytolytic and cytostatic activity of synthetic necrosamine (4,5-diaminoeicosane) on two strains of human tumor cells cultivated in vitro", *CAPLUS accession No. 1960: 30191*. Jan. 9, 1961, Chemical Abstracts Service, Columbus, OH.

Alaupovic, et al., Croatica Chemica Acta., 19956, 28, 219-223.

* cited by examiner

ANTITUMORAL COMPOUNDS

CROSS-REFERENCE TO RELATED APPLICATION

This application claims priority from PCT/GB01/02487 filed on Jun. 6, 2001, which claims priority from United Kingdom Patent Application No. GB 0013783.6, filed on Jun. 6, 2000, United Kingdom Patent Application No. GB 0102472.8 filed on Jan. 31, 2001, and United Kingdom Patent Application No. GB 0104732.3, all of which are incorporated herein by reference in their entirety.

FIELD OF THE INVENTION

The present invention relates to new antitumoral derivatives of spisulosine-285.

BACKGROUND OF THE INVENTION

Spisulosine 285 is a bioactive compound that has been found to possess specific antitumor activity, described in the International Patent WO 99/52521. In the same patent specification are also described sphingoid-type bases spisulosines 299 and 313 and some sphingosine analogs.

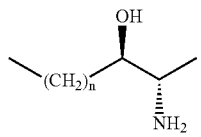

1 (spisulosine-285) n=14
2 (spisulosine-299) n=15
3 (spisulosine-313) n=16

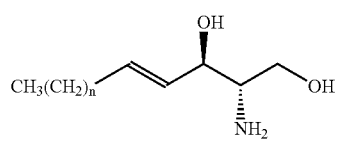

sphingosine, n=12 and nonadeca-4-sphingenine, n=13; and

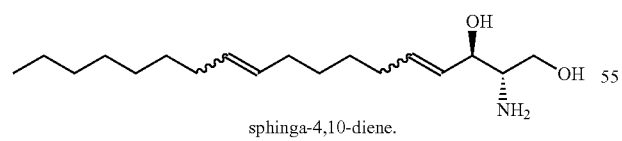

sphinga-4,10-diene.

Spisulosines 285, 299 and 313 were isolated from *Spisula polynyma*, an edible clam originally isolated from samples found off the coast of Japan. The compound we call spisulosine 285 and the syn diastereoisomer were first synthetized by Croatian researchers in the determination of absolute configurations of lipid bases with two or more asymmetric carbon atoms (Prostenik, M.; Alaupovic, P. *Croat. Chem. Acta.* 1957, 29, 393).

SUMMARY OF THE INVENTION

The present invention is directed to analogs of the spisulosine family having the following formulae I and II:

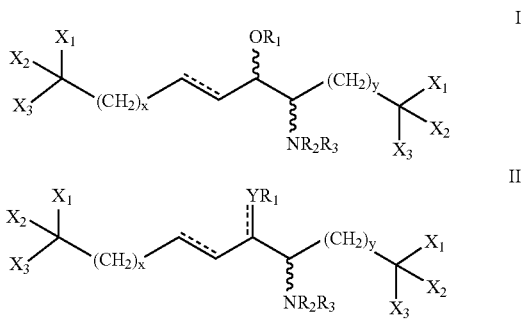

Wherein the substituent groups defined by $R_1$, $R_2$ and $R_3$ are each independently selected of H, C(=O)R', P(=O)R'R'', S(=O)R'R'', substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl. Wherein each of the R', R'' groups is independently selected from the group consisting of H, OH, $NO_2$, $NH_2$, SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ynyl, substituted or unsubstituted aryl.

$R_2$ can be independently an internal salt. Preferred internal salts are formed using any kind of mineral or organic acid such as hydrochloric acid, hydrobromic acid, tartaric acid, succinic acid, etc.

Wherein the substituent groups defined by $X_1$, $X_2$ and $X_3$ are independently selected of H, OH, OR', SH, SR', SOR', $SO_2R'$, $NO_2$, $NH_2$, NHR', N(R')$_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic. Wherein substituent groups defined by R' are each independently selected from the group consisting of H, OH, OR', SH, SR', SOR', $SO_2R'$, $NO_2$, $NH_2$, NHR', N(R')$_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic.

Wherein x and y can be between 0 and 20. Preferably x is in the range 8 to 16, more preferably 10, 11, 12, 13 or 14. Preferably y is 0, 1 or 2. Currently the most preferred is that x is 11, 12 or 13, and y is 0 or 1.

Wherein the dotted line is one or several double bonds placed in any particular position of the side chain.

Wherein the stereochemistry of the groups $OR_1$ and $NR_2R_3$ in formula I can be independently syn or anti.

Wherein the group defined by Y in formula II is independently selected from the group consisting of N, O, P, S, halogen. Wherein the dotted line is a single or double bond. Wherein $R_1$ is independently selected of H, C(=O)R', P(=O)R'R'', S(=O)R'R'', substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl. Wherein each of the R', R'' groups is independently selected from the group consisting of H, OH, $NO_2$, $NH_2$, SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl.

In one aspect, we provide compounds of the formula I:

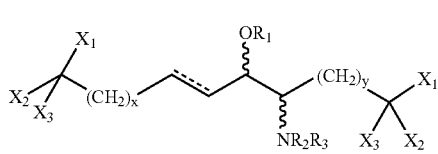

Wherein the substituent groups defined by $R_1$, $R_2$ and $R_3$ are each independently selected of H, C(=O)R', substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl.

$R_2$ can be independently an internal salt. Preferred internal salts are formed using any kind of mineral or organic acid such as hydrochloric acid, hydrobromic acid, tartaric acid, succinic acid, etc.

Wherein each of the R' groups is independently selected from the group consisting of H, OH, $NO_2$, $NH_2$, SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl.

Wherein $X_1$, $X_2$ and $X_3$ are independently selected of H, OH, OR', SH, SR', SOR', $SO_2R'$, $NO_2$, $NH_2$, NHR', N(R')$_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic.

Wherein substituent groups defined by R' are each independently selected from the group consisting of H, OH, OR', SH, SR', SOR', $SO_2R'$, $NO_2$, $NH_2$, NHR', N(R')$_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic.

Wherein x and y can be between 0 and 20.

Wherein the dotted line is one or several double bonds placed in any particular position of the side chain.

Wherein the stereochemistry of the groups $OR_1$ and $NR_2R_3$ can be independently syn or anti.

Suitable halogen substituents in the compounds of the present invention include F, Cl, Br and I.

Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alksulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazolyl. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 2, 3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

References herein to substituted R' groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1–6 alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl. Substituent groups may themselves be substituted, as in a trifluoromethylcinnamoyl group or an aminoacid acyl group such as with valine or Boc-valine.

1. The present invention notably provides compounds of formula:

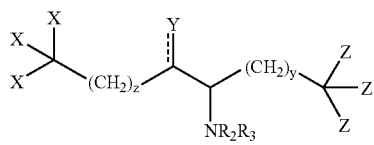

wherein:

each X is the same or different, and represents H, OH, OR', SH, SR', SOR', $SO_2R'$, $NO_2$, $NH_2$, NHR', $N(R')_2$, NHC(O)R', CN, halogen, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, or two groups X may together form =O;

Y is $NR_1$, $OR_1$, $PR_1$, $SR_1$, or halogen, wherein the number of substituents $R_1$ is selected to suit the valency and each $R_1$ is independently selected of H, OH, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, and wherein the dotted line indicates an optional double bond such that Y can also be =O or =N—OH or the group Y with $NR_2R_3$ and the intervening atoms can form a heterocycle;

each Z is the same or different, and represents H, OH, OR', SH, SR', SOR', $SO_2R'$, $NO_2$, $NH_2$, NHR', $N(R')_2$, NHC(O)R', CN, halogen, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, or two groups Z may together form =O;

z is 0 to 25;

y is 0 to 20;

$R_2$ and $R_3$ are the same or different and each is H, C(=O)R', C(=S)R', P(=O)R'R", S(=O)R'R", S(=O)2R', substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl;

each of the R', R" groups is independently selected from the group consisting of H, OH, $NO_2$, $NH_2$, NHR', NR'R", SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_1$–$C_{18}$ alkoxy, substituted or unsubstituted $C_2$–$C_{18}$ alkenyl, substituted or unsubstituted $C_2$–$C_{18}$ alkynyl, substituted or unsubstituted aryl;

there may be one or more unsaturations in the hydrocarbon backbone defined by the chain:

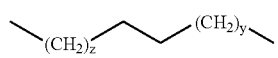

and salts thereof.

Typically each X is H.

Typically Y is $NR_1$, $OR_1$, $PR_1$, or halogen, wherein the number of substituents $R_1$ is selected to suit the valency and each $R_1$ is independently selected of H, C(=O)R', P(=O)R'R", substituted or unsubstituted $C_1$–$C_{18}$ alkyl, and wherein the dotted line indicates an optional double bond such that Y can also be =O or =N—OH, or the group Y with $NR_2R_3$ and the intervening atoms can form a heterocycle.

Typically Z represents H, $NH_2$, NHR', $N(R')_2$, halogen, substituted or unsubstituted $C_1$–$C_{18}$ alkyl, substituted or unsubstituted aryl, substituted or unsubstituted heteroaromatic.

Typically z is 10 to 20.

Typically is 0 to 4.

Typically $R_2$ and $R_3$ are the same or different and each is H, C(=O)R', C(=S)R', S(=O)R'R", S(=O)$_2$R', substituted or unsubstituted $C_1$–$C_{18}$ alkyl;

Each of the R', R" groups is independently selected from the group consisting of H, OH, $NO_2$, $NH_2$, NHR', NR'R", SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_1$–$C_{18}$ alkoxy, substituted or unsubstituted $C_2$–$C_{18}$ alkenyl, substituted or unsubstituted $C_2$–$C_{18}$ alkynyl, substituted or unsubstituted aryl, the selection of respective classes of defintions being made as appropriate to suit the preferred defintions given subsequently.

Compounds of this invention extend to salts, notably pharmaceutically acceptable salts. Such salts may be formed with organic or inorganic acids, and examples are given in this text.

In one class of compounds of this invention, the hydrocarbon backbone defined by the chain:

is of the formula:

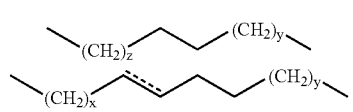

where x is 0 to 20 and the dotted line indicates one or more double bonds in the backbone. For example there can a double bond at the position shown by the dotted line. For example, the hydrocarbon backbone is of the formula:

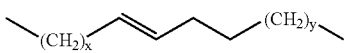

where x and y are as defined.

A preferred group of compounds of this invention include those wherein the terminal group —C(X)$_3$ is —CH$_3$.

In another preferred class, there are no unsaturations in the hydrocarbon backbone.

For preference, z is from 10 to 19.

Suitable compounds include those where Y is OH, O(C=O)R' where R' is optionally halogen-substituted alkyl, OR' where R' is alkyl, halogen, OP(=O)R'$_2$ where R' is alkoxy, NH$_2$, =O, =NOH, or the group Y when OH with NR$_2$R$_3$ and the intervening atoms form a heterocycle of formula:

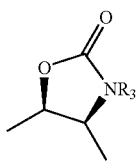

If desired, R$_2$ and R$_3$ are the same. Typically at least one of R$_2$ and R$_3$ is alkyl; alkyl substituted by aryl; hydrogen; C(=O)R' where R' is alkyl or alkoxy, halogen-substituted alkyl, optionally substituted amino-substitued alkyl, aryloxy, alkoxy, optionally substituted aryl-substituted alkenyl; (C=S)NHR' where R' is aryl; (C=O)NHR' where R' is aryl or alkyl; SO$_2$R' where R' is alkyl, or (C=O)R' where R' is optionally substituted aminoalkyl thereby giving an optionally substituted aminoacid acyl group.

In preferred compounds, y is 0 to 3.

The terminal group —C(Z)$_3$ can be —CH$_3$.

The stereochemistry is usually:

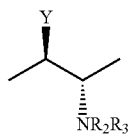

Notable preferred compounds meet two or more of the following criteria:
(a) the terminal group —C(X)$_3$ is —CH$_3$;
(b) z is 10, 11, 12, 13, 14, 15, 16, 17, 18 or 19;
(c) the hydrocarbon backbone is of the formula:

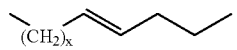

where x is 12;
(d) Y is OR$_1$ where R$_1$ is H, methyl, acetyl, PO(OMe)2, COCF3 or Y is Cl, NH$_3^+$Cl—, =O, =NOH;
(e) R$_2$ and R$_3$ are independently selected from the group consisting of H, methyl, acetyl, benzyl, Boc, CSNHPh, CONHPh, CONH"Bu, SO$_2$Me, COCF$_3$, COCH=CHPh, COCH=CHPhCF$_3$, COC$_{15}$H$_{32}$, COCH(NHBoc)CHMe$_2$, COCH(NH$_3^+$Cl$^-$)CHMe$_2$;

(f) y is 0, 1, 2 or 3;
(g) Z is the same or different, and represents H, F, methyl, ethyl, hydroxyphenyl, amino, dibenzylamino or NH$_3$Cl;
(h) the stereochemistry is

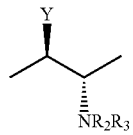

or
(i) the compound or salt is in the form of a salt.

At least one of the following criteria can apply:
(j) z is not 12, 13 or 14;
(k) Y is not OH;
(l) at least one of R$_2$ and R$_3$ is not hydrogen;
(m) y is at least 1;
(n) at least one Z is not hydrogen;
(o) the compound or salt is in the form of a salt.

Preferred combinations of these criteria include (k) with (l), (k) with (n), (l) with (n), any of these with (i), any of these with (a), any of these with (b). Other preferred combinations which may be taken with or without these combinations include (d) taken with (k), (e) taken with (l), (g) taken with (n).

A preferred class of compounds is of the formula:

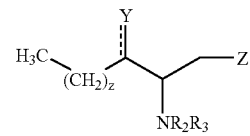

where z is 10 to 19;

Y is OR$_1$ where R$_1$ is H, methyl, acetyl, PO(OMe)$_2$, COCF$_3$ or Y is Cl, NH$_3^+$Cl$^-$, =O, =NOH;

R$_2$ and R$_3$ are independently selected from the group consisting of H, methyl, acetyl, benzyl, Boc, CSNHPh, CONHPh, CONH"Bu, SO$_2$Me, COCF$_3$, COCH=CHPh, COCH=CHPhCF$_3$, COC$_{15}$H$_{32}$, COCH(NHBoc)CHMe$_2$, COCH(NH$_3^+$Cl$^-$)CHMe$_2$;

Z represents H, F, methyl, ethyl, hydroxyphenyl, amino, dibenzylamino or NH$_3$Cl.

Typical compounds of this invention include the following:

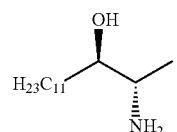

30

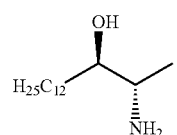

32

| # | Structure |
|---|---|
| 34 | H₂₇C₁₃–CH(OH)–CH(NH₂)–CH₃ |
| 35 | H₂₇C₁₃–CH(OH)–CH(NH₃⁺Cl⁻)–CH₃ |
| 36 | H₂₉C₁₄–CH(OH)–CH(NBn₂)–CH₃ |
| 37 | H₂₉C₁₄–CH(OH)–CH(NH₂)–CH₃ |
| 38 | H₂₉C₁₄–CH(OH)–CH(NH₃⁺Cl⁻)–CH₃ |
| 40 | H₃₁C₁₅–CH(OH)–CH(NH₃)₂⁺(C₂H₂O₃⁻)₂–CH₃ |
| 41 | H₃₁C₁₅–CH(OH)–CH(NH₃⁺Cl⁻)–CH₃ |
| 42 | H₃₃C₁₆–CH(OH)–CH(NBn₂)–CH₃ |
| 43 | H₃₃C₁₆–CH(OH)–CH(NH₃⁺Cl⁻)–CH₃ |
| 44 | H₃₅C₁₇–CH(OH)–CH(NBn₂)–CH₃ |
| 45 | H₃₅C₁₇–CH(OH)–CH(NH₃⁺Cl⁻)–CH₃ |
| 47 | H₃₇C₁₈–CH(OH)–CH(NH₂)–CH₃ |
| 48 | H₃₇C₁₈–CH(OH)–CH(NH₃⁺Cl⁻)–CH₃ |
| 50 | H₃₉C₁₉–CH(OH)–CH(NH₂)–CH₃ |
| 52 | H₄₁C₂₀–CH(OH)–CH(NH₂)–CH₃ |
| 54 | H₂₉C₁₄–CH(OH)–CH(NH₂)–CH₂CH₃ |
| 55 | H₂₉C₁₄–CH(OH)–CH(NH₃⁺Cl⁻)–CH₂CH₃ |
| 57 | H₃₁C₁₅–CH(OH)–CH(NH₂)–CH₂CH₃ |
| 58 | H₃₁C₁₅–CH(OH)–CH(NH₃⁺Cl⁻)–CH₂CH₃ |
| 60 | H₃₃C₁₆–CH(OH)–CH(NH₂)–CH₂CH₃ |
| 61 | H₃₃C₁₆–CH(OH)–CH(NH₃⁺Cl⁻)–CH₂CH₃ |
| 63 | H₃₅C₁₇–CH(OH)–CH(NH₂)–CH₂CH₃ |

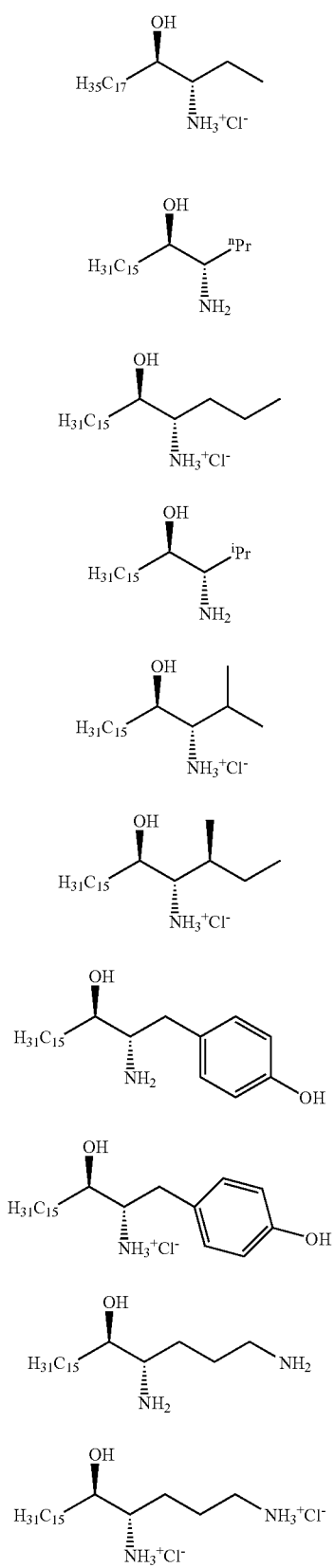
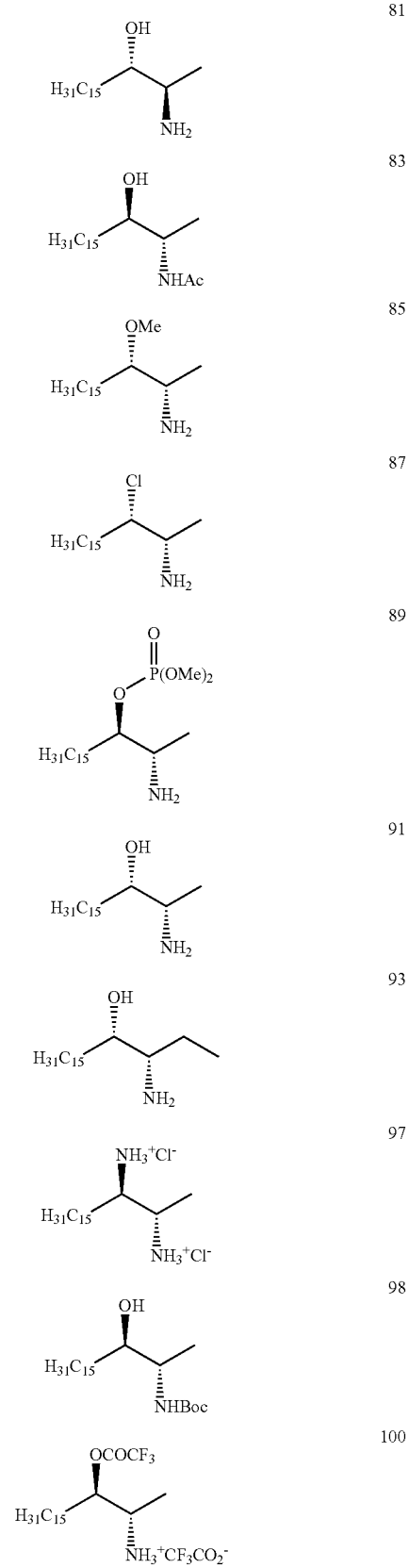

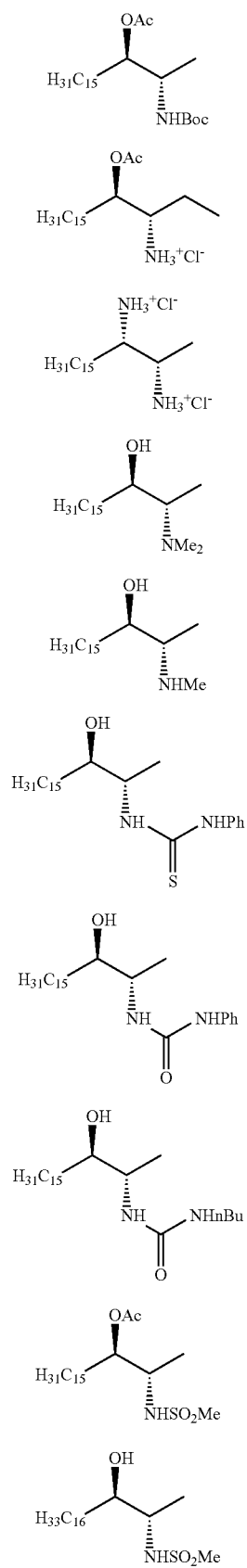

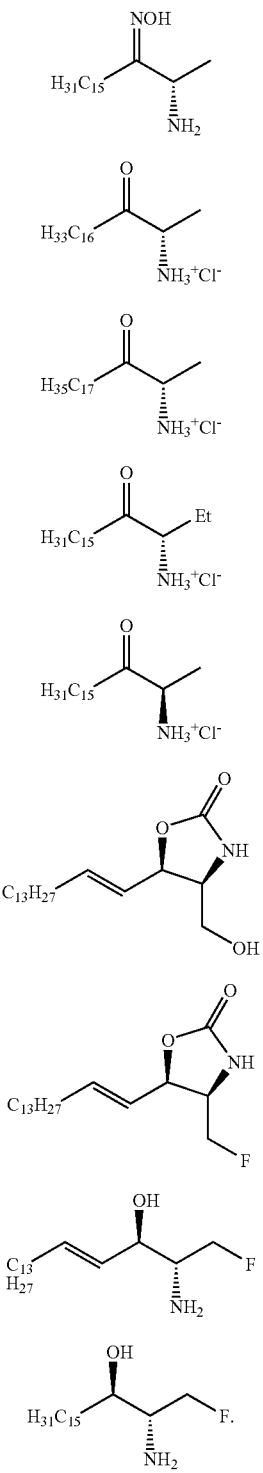

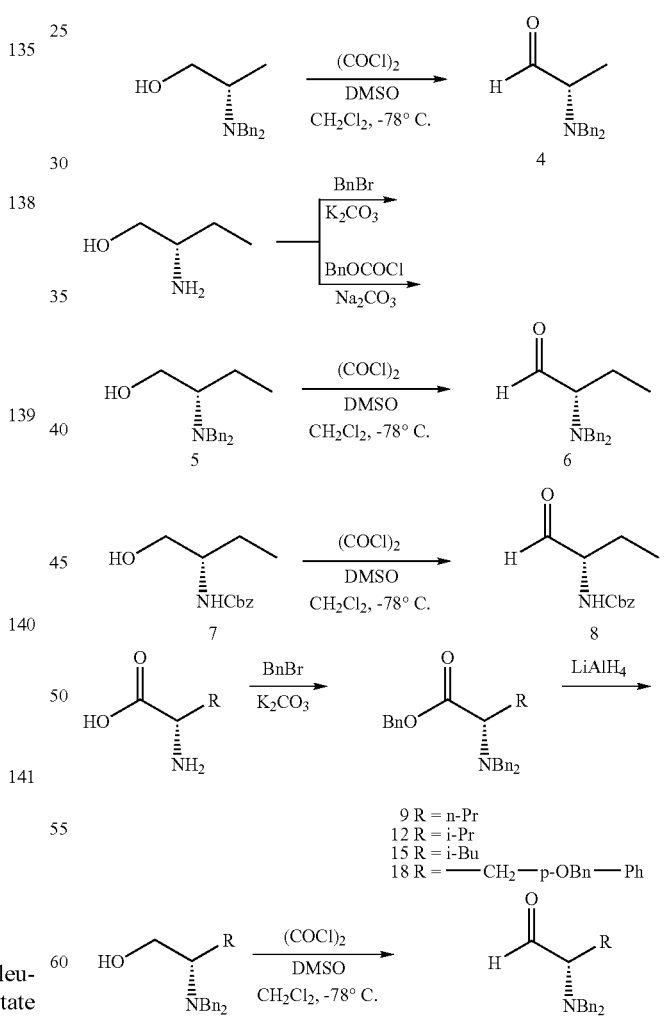

Antitumoral activities of these compounds include leukaemias, lung cancer, colon cancer, kidney cancer, prostate cancer, ovarian cancer, breast cancer, sarcomas and melanomas.

Another especially preferred embodiment of the present invention is pharmaceutical compositions useful as antitumor agents which contain as active ingredient a compound or compounds of the invention, including salts, as well as the processes for their preparation.

Examples of pharmaceutical compositions include any solid (tablets, pills, capsules, granules etc.) or liquid (solutions, suspensions or emulsions) with suitable composition or oral, topical or parenteral administration.

Administration of the compounds or compositions of the present invention may be any suitable method, such as intravenous infusion, oral preparation, intraperitoneal and intravenous preparation.

DETAILED DESCRIPTION OF THE PREFERRED EMBODIMENTS

The compounds of the present invention can be prepared synthetically. The present invention includes the synthetic processes described in the following schemes. Scheme 1 illustrates the preparation of the different aldehydes used as starting materials for the synthesis of spisulosine derivatives.

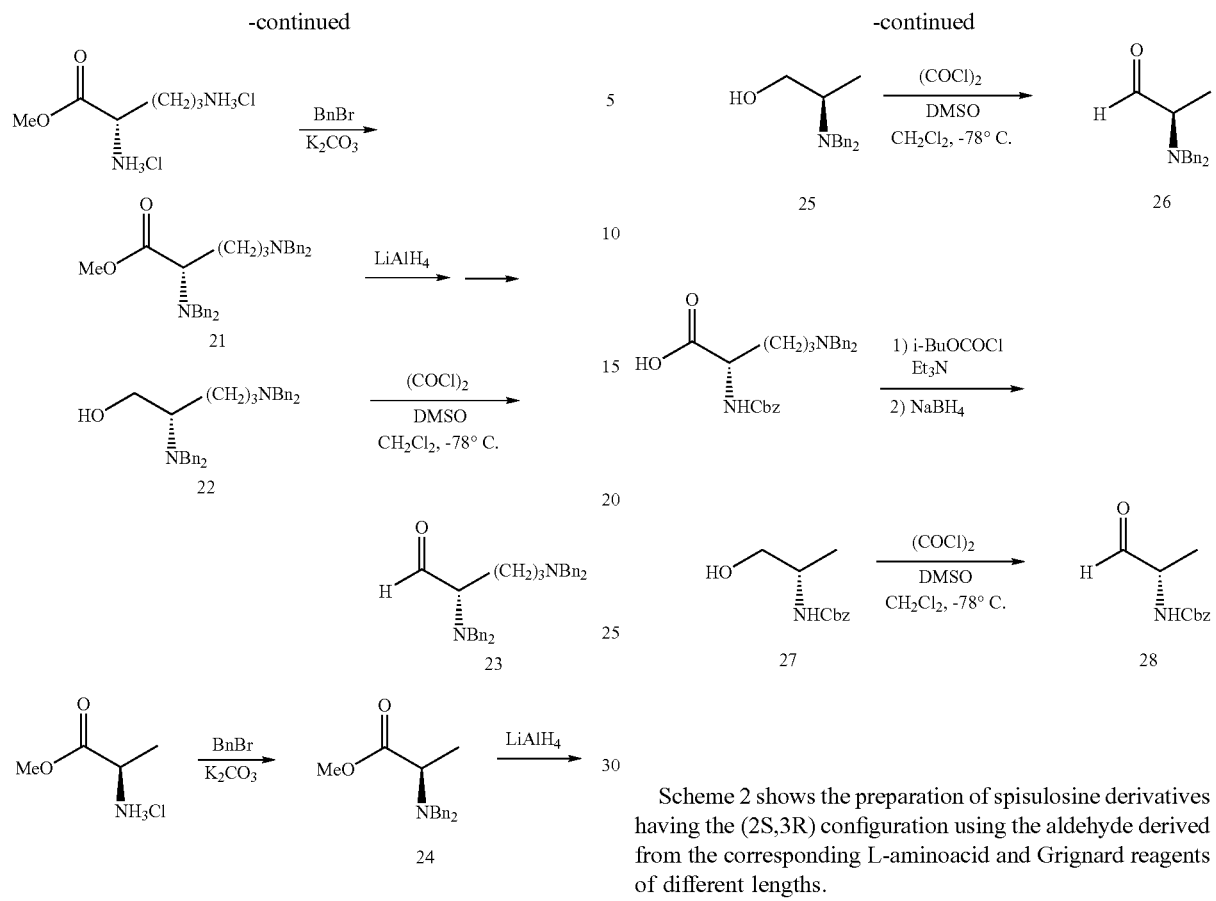
Scheme 2 shows the preparation of spisulosine derivatives having the (2S,3R) configuration using the aldehyde derived from the corresponding L-aminoacid and Grignard reagents of different lengths.
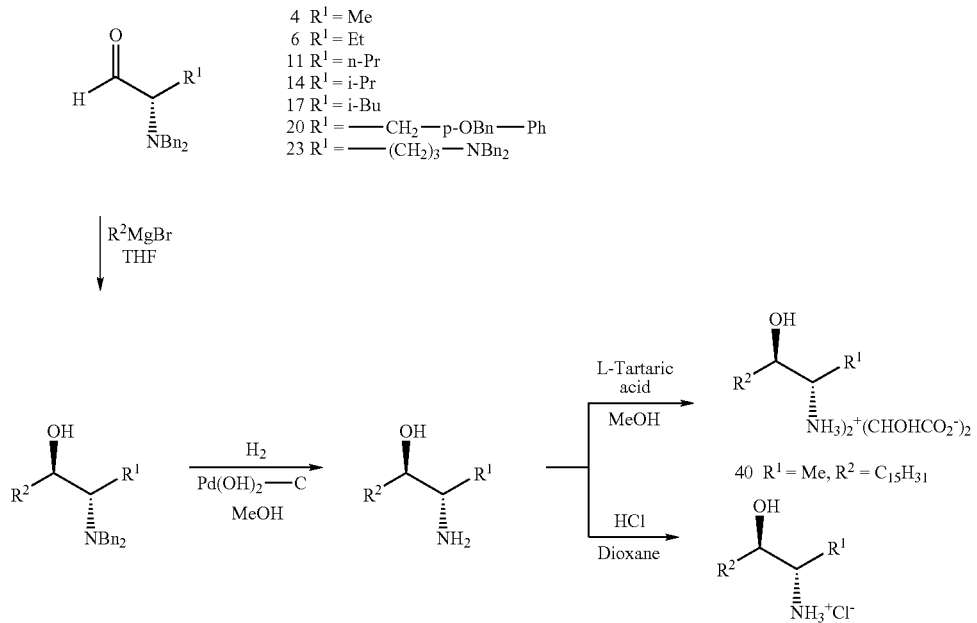

29 $R^1$ = Me, $R^2$ = $C_{11}H_{23}$
31 $R^1$ = Me, $R^2$ = $C_{12}H_{25}$
33 $R^1$ = Me, $R^2$ = $C_{13}H_{27}$
36 $R^1$ = Me, $R^2$ = $C_{14}H_{29}$
39 $R^1$ = Me, $R^2$ = $C_{15}H_{31}$
42 $R^1$ = Me, $R^2$ = $C_{16}H_{33}$
44 $R^1$ = Me, $R^2$ = $C_{17}H_{35}$
46 $R^1$ = Me, $R^2$ = $C_{18}H_{37}$
49 $R^1$ = Me, $R^2$ = $C_{19}H_{39}$
51 $R^1$ = Me, $R^2$ = $C_{20}H_{41}$
53 $R^1$ = Et, $R^2$ = $C_{14}H_{29}$
56 $R^1$ = Et, $R^2$ = $C_{15}H_{31}$
59 $R^1$ = Et, $R^2$ = $C_{16}H_{33}$
62 $R^1$ = Et, $R^2$ = $C_{17}H_{35}$
65 $R^1$ = n-Pr, $R^2$ = $C_{15}H_{31}$
68 $R^1$ = i-Pr, $R^2$ = $C_{15}H_{31}$
71 $R^1$ = i-Bu, $R^2$ = $C_{15}H_{31}$
74 $R^1$ = —$CH_2$—p-OBn—Ph, $R^2$ = $C_{15}H_{31}$
77 $R^1$ = —$(CH_2)_3$—$NBn_2$, $R^2$ = $C_{15}H_{31}$

-continued

30 $R^1$ = Me, $R^2$ = $C_{11}H_{23}$
32 $R^1$ = Me, $R^2$ = $C_{12}H_{25}$
34 $R^1$ = Me, $R^2$ = $C_{13}H_{27}$
37 $R^1$ = Me, $R^2$ = $C_{14}H_{29}$
1 $R^1$ = Me, $R^2$ = $C_{15}H_{31}$
2 $R^1$ = Me, $R^2$ = $C_{16}H_{33}$
3 $R^1$ = Me, $R^2$ = $C_{17}H_{35}$
47 $R^1$ = Me, $R^2$ = $C_{18}H_{37}$
50 $R^1$ = Me, $R^2$ = $C_{19}H_{39}$
52 $R^1$ = Me, $R^2$ = $C_{20}H_{41}$
54 $R^1$ = Et, $R^2$ = $C_{14}H_{29}$
57 $R^1$ = Et, $R^2$ = $C_{15}H_{31}$
60 $R^1$ = Et, $R^2$ = $C_{16}H_{33}$
63 $R^1$ = Et, $R^2$ = $C_{17}H_{35}$
66 $R^1$ = n-Pr, $R^2$ = $C_{15}H_{31}$
69 $R^1$ = i-Pr, $R^2$ = $C_{15}H_{31}$
72 $R^1$ = i-Bu, $R^2$ = $C_{15}H_{31}$
75 $R^1$ = $CH_2$—p-OH—Ph, $R^2$ = $C_{15}H_{31}$
78 $R^1$ = $(CH_2)_3NH_2$, $R^2$ = $C_{15}H_{31}$

35 $R^1$ = Me, $R^2$ = $C_{13}H_{27}$
38 $R^1$ = Me, $R^2$ = $C_{14}H_{29}$
41 $R^1$ = Me, $R^2$ = $C_{15}H_{31}$
43 $R^1$ = Me, $R^2$ = $C_{16}H_{33}$
45 $R^1$ = Me, $R^2$ = $C_{17}H_{35}$
48 $R^1$ = Me, $R^2$ = $C_{18}H_{37}$
55 $R^1$ = Et, $R^2$ = $C_{14}H_{29}$
58 $R^1$ = Et, $R^2$ = $C_{15}H_{31}$
61 $R^1$ = Et, $R^2$ = $C_{16}H_{33}$
64 $R^1$ = Et, $R^2$ = $C_{17}H_{35}$
67 $R^1$ = n-Pr, $R^2$ = $C_{15}H_{31}$
70 $R^1$ = i-Pr, $R^2$ = $C_{15}H_{31}$
73 $R^1$ = i-Bu, $R^2$ = $C_{15}H_{31}$
76 $R^1$ = $CH_2$—p-OH—Ph, $R^2$ = $C_{15}H_{31}$
79 $R^1$ = $(CH_2)_3NH_3Cl$, $R^2$ = $C_{15}H_{31}$

Scheme 3 describes the synthesis of the enantiomeric form of the final products of spisulosine starting from the corresponding D-alanine derivative.

Scheme 3

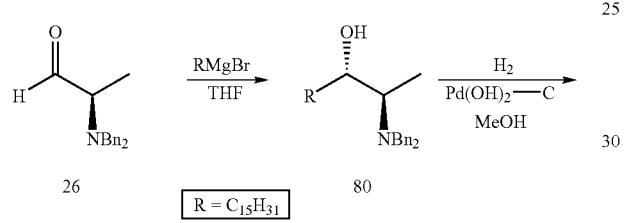

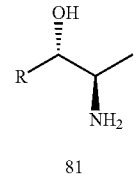

The methods for the synthesis of N-acetyl, O-methyl, 3-halo-3-deoxy and O-phosphate derivatives of spisulosine are outlined in Scheme 4.

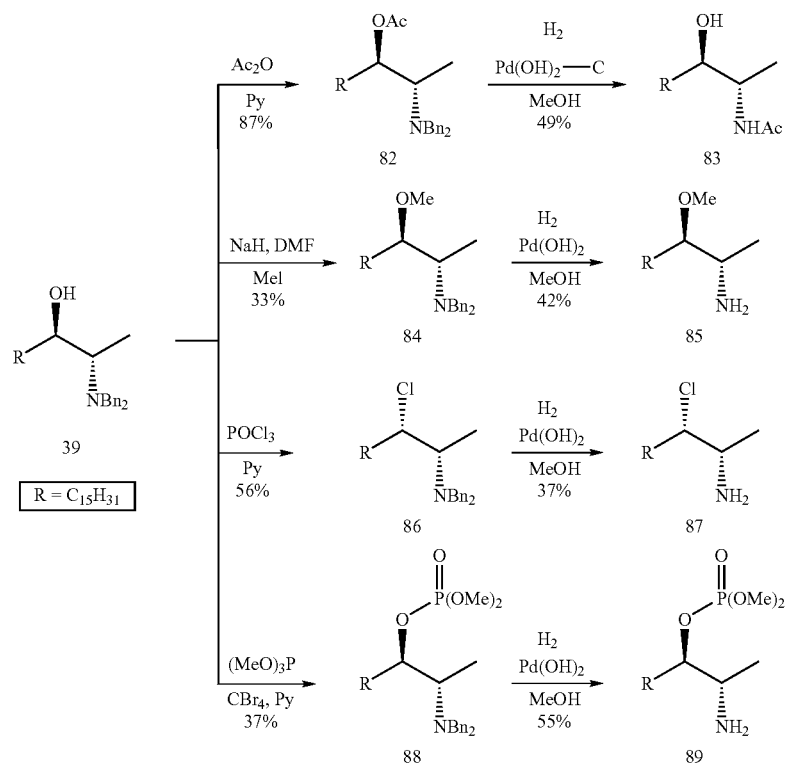

Scheme 5 shows the preparation of the corresponding (2S,3S) diastereoisomers of spisulosine, in which the final diamine is prepared via the azide intermediate. Preparation of the diastereoisomeric form of this diamine is outlined in Scheme 6.

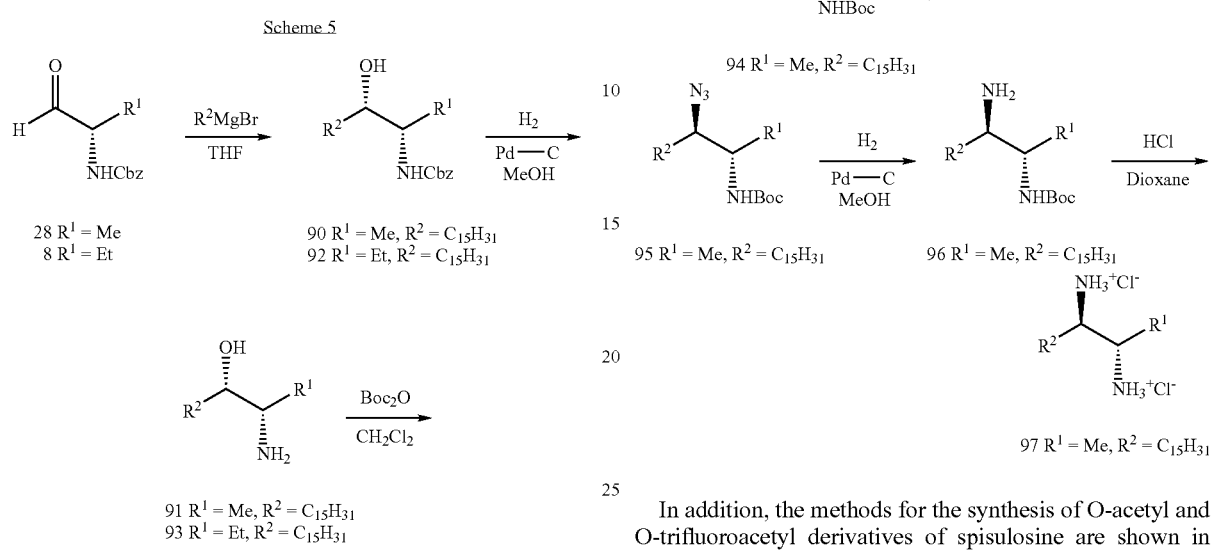

In addition, the methods for the synthesis of O-acetyl and O-trifluoroacetyl derivatives of spisulosine are shown in Scheme 6.

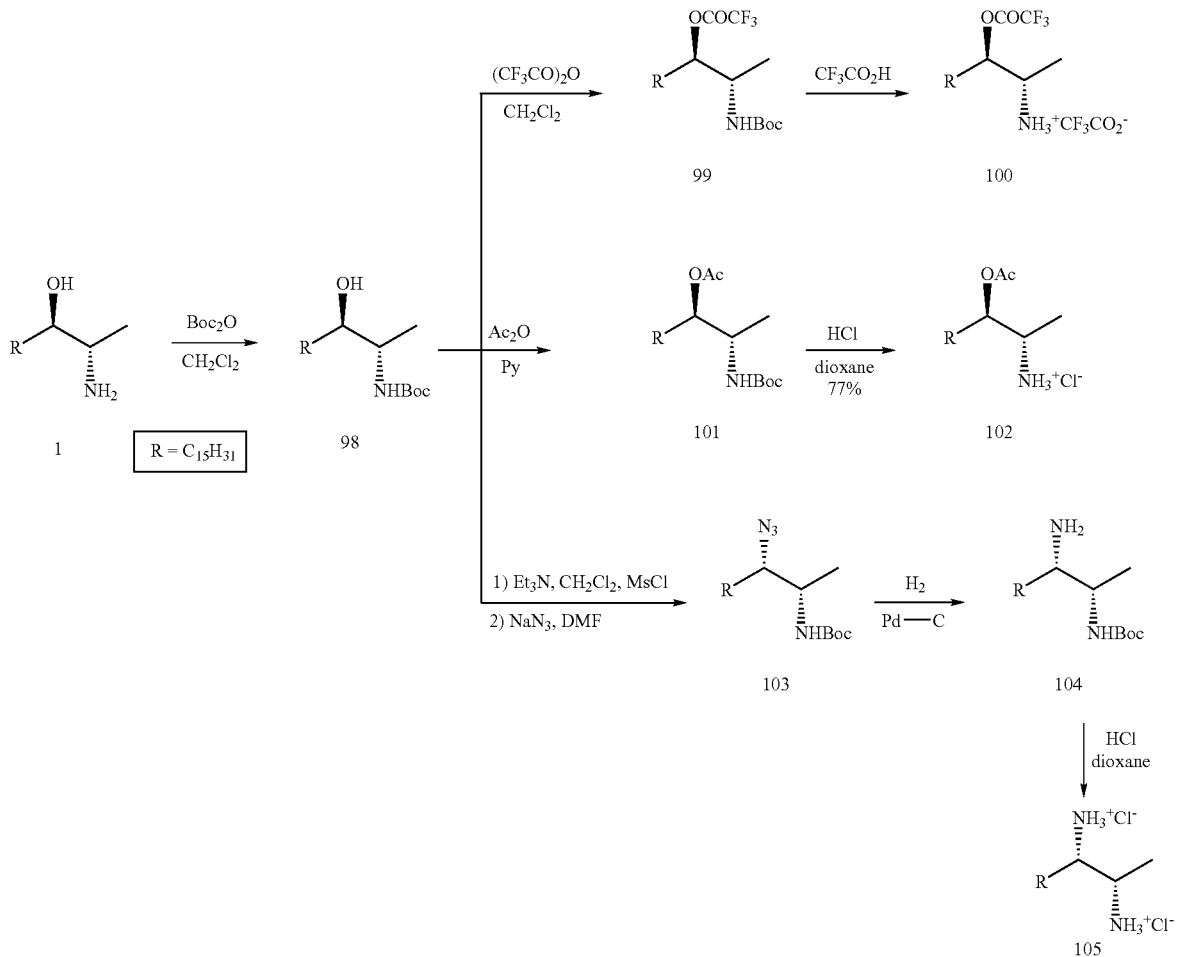

Other Spisulosines 285 and 299 derivatives are prepared following different procedures which are described in Scheme 7.
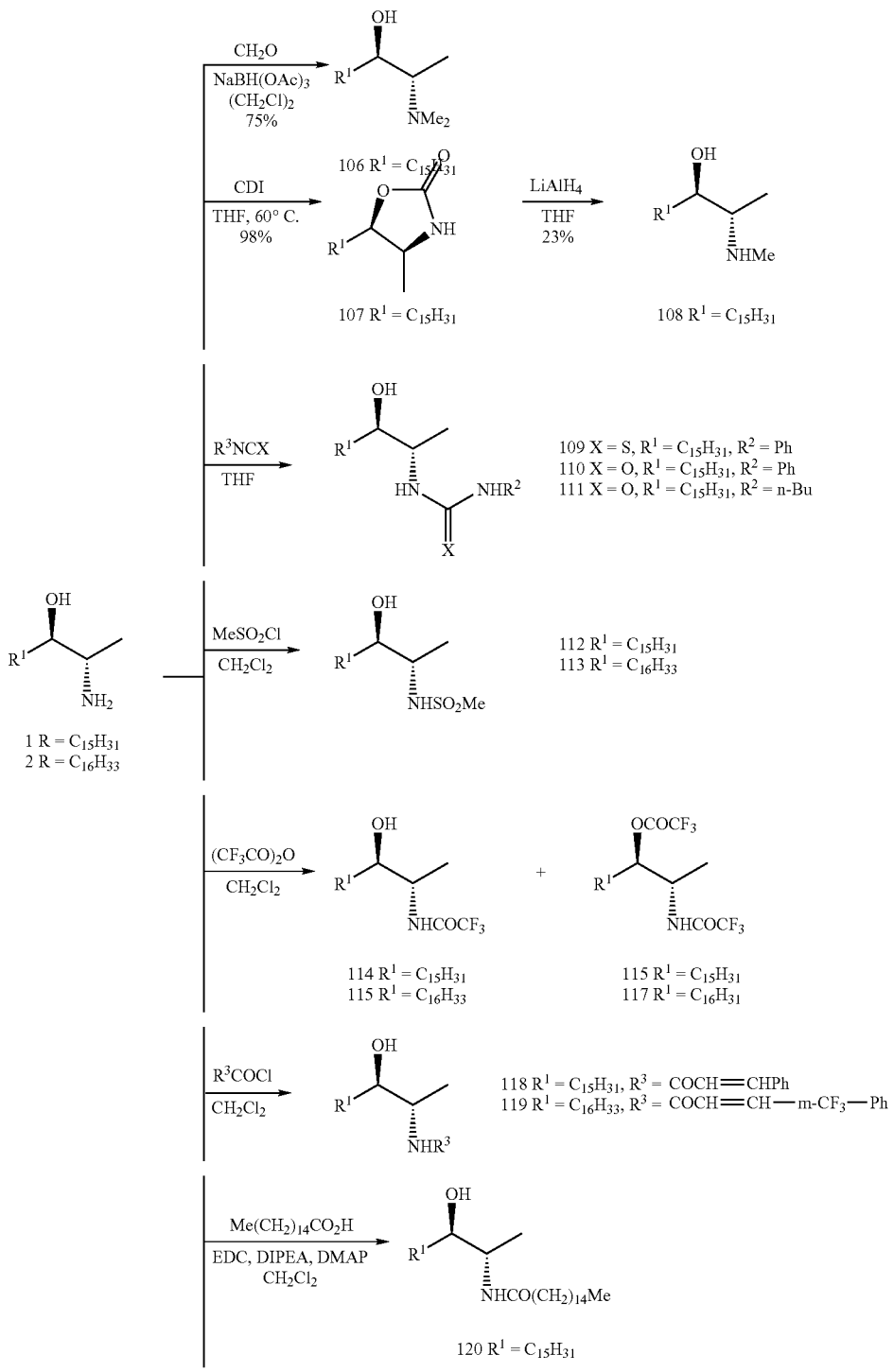

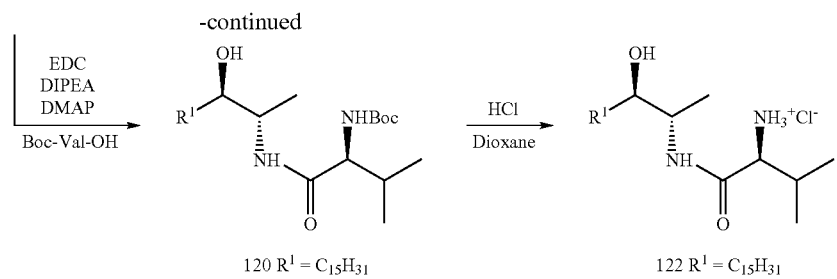
3-Keto derivatives of spisulosine and their corresponding oximes can be prepared as described in Scheme 8.
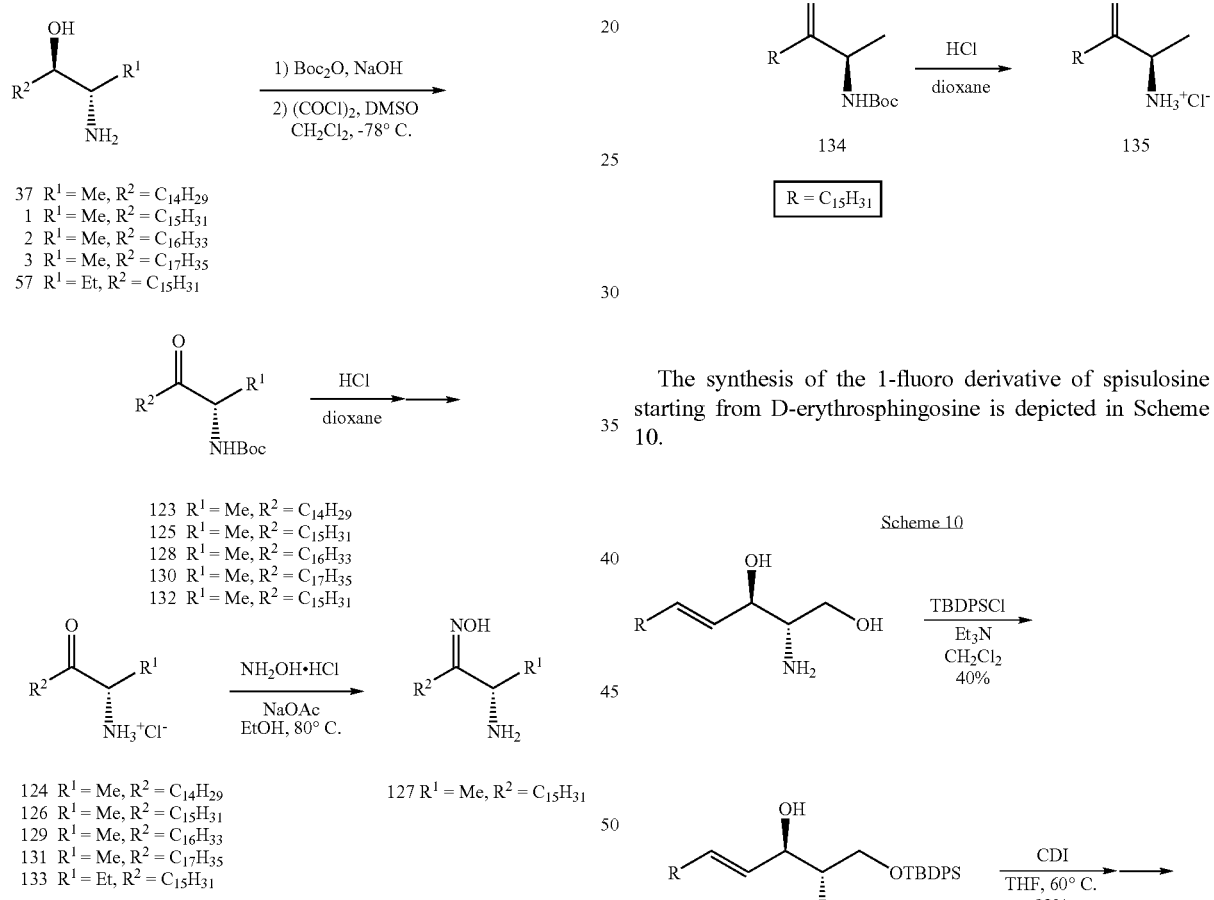
The enantiomeric form of ketone 126 is prepared from the appropriate aminoalcohol as indicated in Scheme 9.
The synthesis of the 1-fluoro derivative of spisulosine starting from D-erythrosphingosine is depicted in Scheme 10.
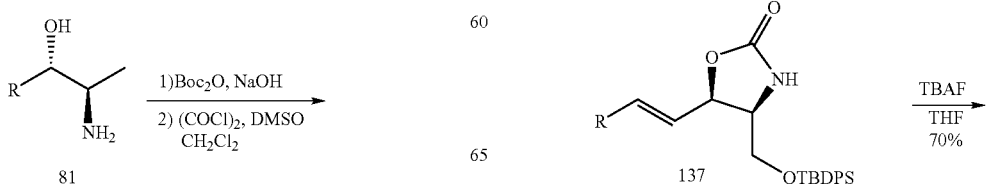

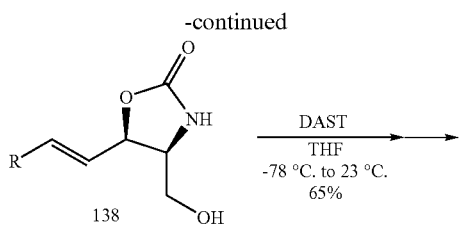
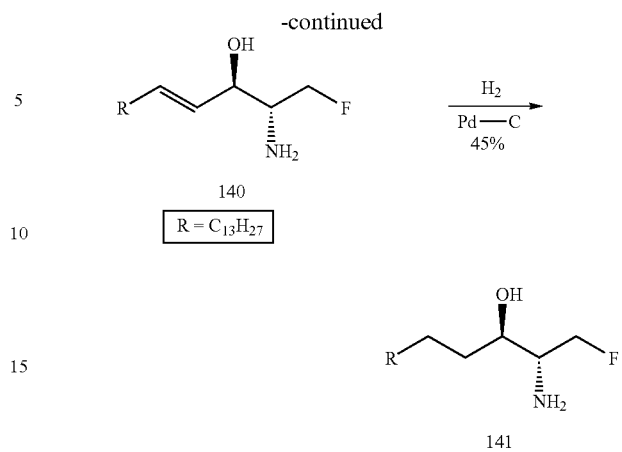
TABLE 1
Cytotoxicity of Spisulosine Analogs (IC50, Molar)
| Compound | MW | P388 | A549 | HT29 | MEL28 | DU145 |
|---|---|---|---|---|---|---|
| 1 | 285.51 | 3.50E−08 | 3.50E−08 | 3.50E−08 | 1.75E−07 | 3.50E−08 |
| 2 | 299.53 | 3.34E−08 | 3.34E−08 | 3.34E−08 | 3.34E−08 | 3.34E−08 |
| 3 | 313.56 | 3.19E−08 | 3.19E−08 | 3.19E−08 | 3.19E−07 | 3.19E−08 |
| 30 | 229.40 | 4.36E−07 | 2.18E−06 | 4.36E−07 | 2.18E−06 | 2.18E−06 |
| 32 | 243.43 | 4.11E−07 | 4.11E−07 | 4.11E−07 | 2.05E−06 | 4.11E−07 |

TABLE 1-continued

Cytotoxicity of Spisulosine Analogs (IC50, Molar)

| Compound | MW | P388 | A549 | HT29 | MEL28 | DU145 |
|---|---|---|---|---|---|---|
| 34: $H_{27}C_{13}$–CH(OH)–CH(NH$_2$)–CH$_3$ | 257.46 | 3.88E−07 | 1.94E−07 | 3.88E−07 | 3.68E−07 | 1.94E−07 |
| 35: $H_{27}C_{13}$–CH(OH)–CH(NH$_3^+$Cl$^-$)–CH$_3$ | 293.92 | | 3.40E−09 | 3.40E−09 | | |
| 36: $H_{29}C_{14}$–CH(OH)–CH(NBn$_2$)–CH$_3$ | 451.73 | NA | NA | NA | NA | NA |
| 37: $H_{29}C_{14}$–CH(OH)–CH(NH$_2$)–CH$_3$ | 271.48 | 3.68E−08 | 3.68E−08 | 3.68E−08 | 3.68E−08 | 3.68E−08 |
| 38: $H_{29}C_{14}$–CH(OH)–CH(NH$_3^+$Cl$^-$)–CH$_3$ | 307.94 | | 3.25E−08 | 3.25E−08 | | |
| 40: $H_{31}C_{15}$–CH(OH)–CH(NH$_3)_2^+$(C$_2$H$_2$O$_3^-$)$_2$–CH$_3$ | 360.55 | 2.77E−08 | 2.77E−08 | 2.77E−08 | 2.77E−08 | 2.77E−08 |
| 41: $H_{31}C_{15}$–CH(OH)–CH(NH$_3^+$Cl$^-$)–CH$_3$ | 321.97 | 3.11E−08 | 3.11E−08 | 1.55E−08 | 3.11E−07 | 3.11E−08 |
| 42: $H_{33}C_{16}$–CH(OH)–CH(NBn$_2$)–CH$_3$ | 479.78 | NA | NA | NA | NA | NA |

TABLE 1-continued
Cytotoxicity of Spisulosine Analogs (IC50, Molar)
| Compound | MW | P388 | A549 | HT29 | MEL28 | DU145 |
|---|---|---|---|---|---|---|
| 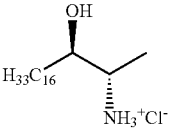 43 | 336.00 | | 2.98E−08 | 2.98E−08 | | |
| 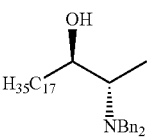 44 | 493.81 | NA | NA | NA | NA | NA |
| 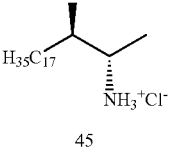 45 | 350.02 | | 1.43E−08 | 1.43E−08 | | |
| 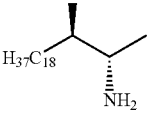 47 | 327.59 | 1.53E−07 | 3.05E−07 | 3.05E−07 | 3.05E−07 | 3.05E−07 |
| 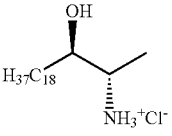 48 | 364.05 | | 2.75E−08 | 2.75E−08 | | |
| 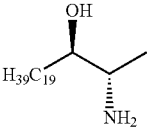 50 | 341.61 | 2.93E−07 | NA | 1.46E−06 | NA | 1.46E−06 |
| 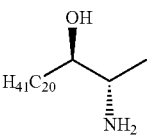 52 | 355.64 | 1.41E−06 | NA | 2.81E−06 | NA | 2.81E−06 |
| 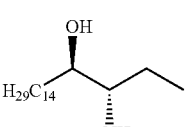 54 | 285.51 | | 3.50E−09 | 3.50E−09 | | |

TABLE 1-continued
Cytotoxicity of Spisulosine Analogs (IC50, Molar)
| Compound | MW | P388 | A549 | HT29 | MEL28 | DU145 |
|---|---|---|---|---|---|---|
| 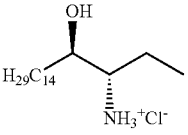<br>55 | 321.97 | | 1.55E−08 | 1.55E−08 | | |
| 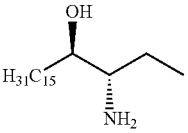<br>57 | 299.53 | 3.34E−08 | 3.34E−08 | 3.34E−08 | 3.34E−07 | 3.34E−08 |
| 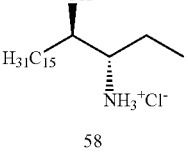<br>58 | 336.00 | | 2.98E−09 | 2.98E−09 | | |
| 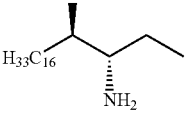<br>60 | 313.56 | | 3.19E−07 | 3.19E−07 | | |
| 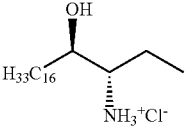<br>61 | 350.02 | | 2.86E−08 | 2.86E−08 | | |
| 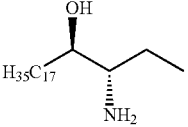<br>63 | 327.59 | | 3.05E−08 | 3.05E−08 | | |
| 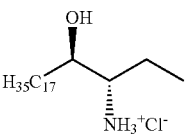<br>64 | 364.05 | | 2.75E−08 | 2.75E−08 | | |
| 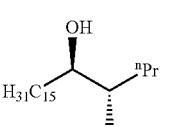<br>66 | 313.56 | | 1.59E−07 | 1.59E−07 | | |

TABLE 1-continued
Cytotoxicity of Spisulosine Analogs (IC50, Molar)
| Compound | MW | P388 | A549 | HT29 | MEL28 | DU145 |
|---|---|---|---|---|---|---|
| 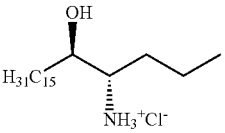 67 | 350.02 | | 2.86E−08 | 2.86E−08 | | |
| 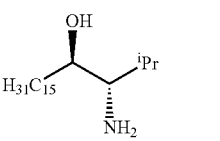 69 | 313.56 | | NA | NA | | |
| 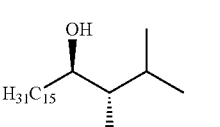 70 | 350.02 | | NA | NA | | |
| 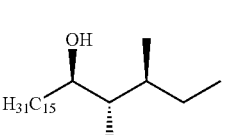 73 | 364.05 | | NA | NA | | |
| 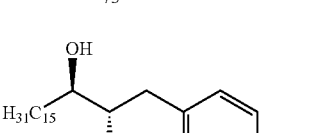 75 | 377.60 | | 1.32E−06 | 1.32E−06 | | |
| 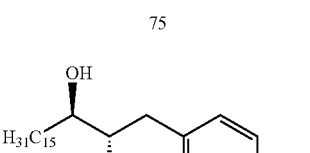 76 | 414.06 | | 2.42E−07 | 2.42E−07 | | |
| 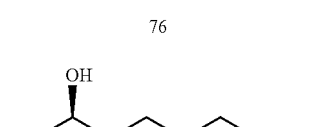 78 | 328.58 | | 1.52E−06 | 1.52E−06 | | |
| 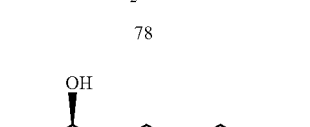 79 | 401.50 | | 1.24E−06 | 1.24E−06 | | |

TABLE 1-continued

Cytotoxicity of Spisulosine Analogs (IC50, Molar)

| Compound | MW | P388 | A549 | HT29 | MEL28 | DU145 |
|---|---|---|---|---|---|---|
| 81 (OH, H₃₁C₁₅, NH₂) | 285.51 | 3.50E−07 | 3.50E−07 | 3.50E−07 | 3.50E−07 | 3.50E−07 |
| 83 (OH, H₃₁C₁₅, NHAc) | 327.55 | NA | NA | NA | NA | NA |
| 85 (OMe, H₃₁C₁₅, NH₂) | 299.53 | | 1.67E−06 | 1.67E−06 | | |
| 87 (Cl, H₃₁C₁₅, NH₂) | 303.95 | 3.29E−07 | 3.29E−07 | 3.29E−07 | 3.29E−07 | 3.29E−07 |
| 89 (O-P(O)(OMe)₂, H₃₁C₁₅, NH₂) | 393.54 | 1.27E−06 | 1.27E−06 | 1.27E−06 | 1.27E−06 | 1.27E−06 |
| 91 (OH, H₃₁C₁₅, NH₂) | 285.51 | 3.50E−07 | 3.50E−07 | 3.50E−07 | 3.50E−07 | 3.50E−07 |
| 93 (OH, H₃₁C₁₅, NH₂, ethyl) | 299.53 | 3.34E−07 | 3.34E−07 | 3.34E−07 | 3.34E−07 | 3.34E−07 |

TABLE 1-continued
Cytotoxicity of Spisulosine Analogs (IC50, Molar)
| Compound | MW | P388 | A549 | HT29 | MEL28 | DU145 |
|---|---|---|---|---|---|---|
| 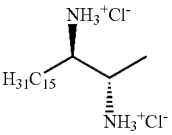 97 | 357.44 | | 1.40E−06 | 1.40E−06 | | |
| 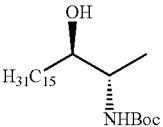 98 | 385.62 | | NA | NA | | |
| 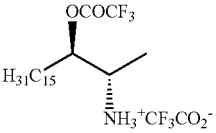 100 | 495.54 | | 2.02E−08 | 2.02E−08 | | |
| 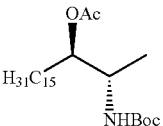 101 | 427.66 | NA | NA | NA | NA | NA |
| 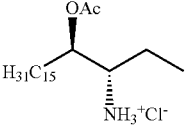 102 | 364.01 | 2.75E−07 | 2.75E−07 | 1.37E−07 | 2.75E−07 | 1.37E−07 |
| 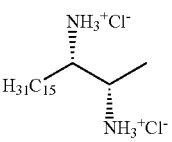 105 | 357.44 | | 2.80E−07 | 2.80E−07 | | |
| 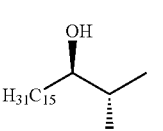 106 | 313.56 | 3.19E−07 | 3.19E−07 | 3.19E−07 | 3.19E−07 | 3.19E−07 |
| 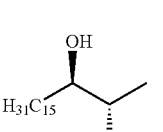 108 | 299.53 | 3.34E−07 | 3.34E−07 | 3.34E−07 | 3.34E−07 | 3.34E−07 |

TABLE 1-continued
Cytotoxicity of Spisulosine Analogs (IC50, Molar)
| Compound | MW | P388 | A549 | HT29 | MEL28 | DU145 |
|---|---|---|---|---|---|---|
| 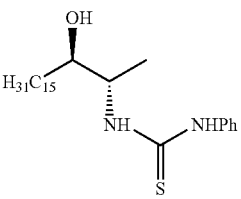 109 | 420.70 | NA | NA | NA | NA | NA |
| 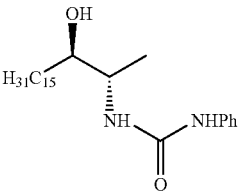 110 | 404.63 | | NA | NA | | |
| 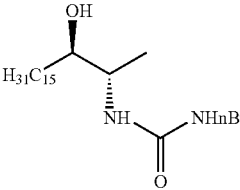 111 | 384.64 | | NA | NA | | |
| 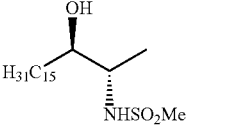 112 | 363.60 | | 2.75E−08 | 2.75E−08 | | |
| 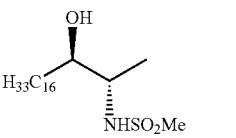 113 | 377.63 | | 2.65E−07 | 2.65E−07 | | |
| 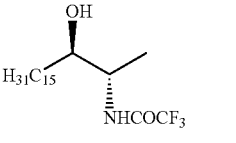 114 | 395.54 | | NA | NA | | |
| 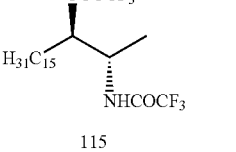 115 | 477.52 | | NA | NA | | |

TABLE 1-continued
Cytotoxicity of Spisulosine Analogs (IC50, Molar)
| Compound | MW | P388 | A549 | HT29 | MEL28 | DU145 |
|---|---|---|---|---|---|---|
| 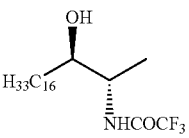 116 | 395.54 | | NA | NA | | |
| 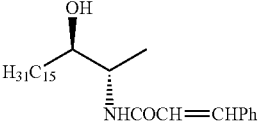 118 | 415.65 | | NA | NA | | |
| 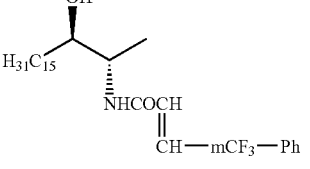 119 | 483.65 | | NA | NA | | |
| 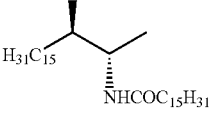 120 | 539.96 | | NA | NA | | |
| 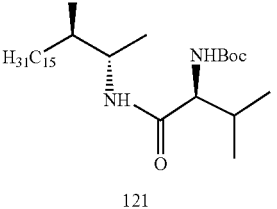 121 | 484.76 | | NA | NA | | |
| 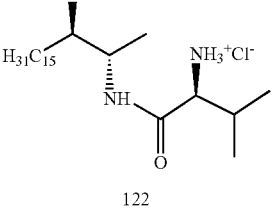 122 | 421.10 | | NA | NA | | |
| 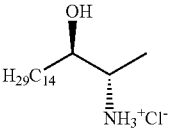 124 | 305.93 | 1.63E−07 | 1.63E−07 | 1.63E−07 | 3.27E−07 | 1.63E−07 |

TABLE 1-continued

| Cytotoxicity of Spisulosine Analogs (IC50, Molar) | | | | | | |
|---|---|---|---|---|---|---|
| Compound | MW | P388 | A549 | HT29 | MEL28 | DU145 |
| 126 | 319.95 | 3.13E−08 | 1.56E−07 | 3.13E−08 | 1.56E−07 | 3.13E−08 |
| 127 | 298.51 | 3.35E−07 | 3.35E−07 | 3.35E−07 | 3.35E−07 | 3.35E−07 |
| 129 | 333.98 | 1.50E−07 | 1.50E−07 | 1.50E−07 | 2.99E−07 | 1.50E−07 |
| 131 | 348.01 | 1.44E−07 | 1.44E−07 | 1.44E−07 | 2.87E−07 | 1.44E−07 |
| 133 | 333.98 | 2.99E−08 | 2.99E−08 | 2.99E−08 | 2.99E−07 | 2.99E−08 |
| 135 | 319.95 | 1.56E−07 | 1.56E−07 | 1.56E−07 | 3.13E−07 | 1.56E−07 |
| 138 | 325.49 | NA | NA | NA | NA | NA |

TABLE 1-continued

Cytotoxicity of Spisulosine Analogs (IC50, Molar)

| Compound | MW | P388 | A549 | HT29 | MEL28 | DU145 |
|---|---|---|---|---|---|---|
| 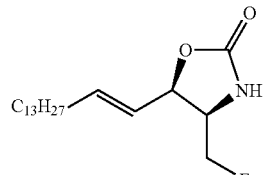 139 | 327.48 | NA | NA | NA | NA | NA |
| 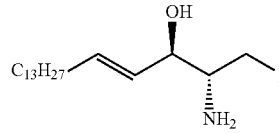 140 | 301.48 | | 3.32E−08 | 3.32E−08 | | |
| 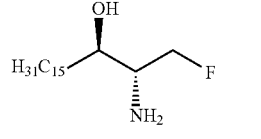 141 | 303.50 | 3.29E−08 | 3.29E−08 | 3.29E−08 | 3.29E−07 | 3.29E−07 |

Methodology: after Berjeron et al, Biochem and Bioph Res. Comm., 1984, 121, 3, 848–854

NA=not active

TABLE 2

Cytotoxicity of Spisulosine Analogs (IC50, Molar)

| Solid Tumors | Line | 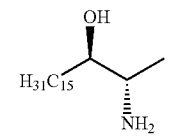 1 | 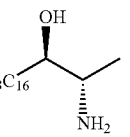 2 | 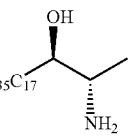 3 | 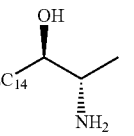 37 |
|---|---|---|---|---|---|
| Bladder | 5637 | | 4.72E−08 | 6.34E−06 | 3.65E−08 |
| Breast | MX-1 | 1.95E−06 | | | |
| Colon | HT-29 | 1.28E−07 | 6.43E−08 | 9.07E−06 | 2.64E−07 |
| Gastric | Hs746t | 3.95E−07 | | | |
| Liver | SK-HEP-1 | 2.97E−07 | | | |
| NSCL | A549 | 8.57E−08 | 3.43E−08 | 9.79E−06 | 1.01E−05 |
| Ovary | SK-OV-3 | 7.02E−07 | | | |
| Pancreas | PANC-1 | | 1.67E−07 | 7.22E−07 | 8.64E−08 |
| Pharynx | FADU | 2.49E−07 | 1.03E−08 | 8.12E−08 | 7.84E−08 |
| Prostate | PC-3 | | 8.60E−08 | 4.9E−08 | 3.79E−07 |
| Prostate | DU-145 | | 7.39E−08 | 9.86E−06 | 2.01E−07 |
| Prostate | LNCAP | | 4.44E−08 | 7.69E−06 | 7.15E−08 |
| Renal | 786-O | 1.38E−07 | | | |
| SCL | NCI-H187 | | 1.63E−07 | 7.17E−06 | NA |
| Retinoblastoma | Y-79 | | 4.65E−06 | NA | NA |
| Melanoma | Mel-28 | | 7.21E−06 | NA | 1.03E−05 |
| Fibrosarcoma | SW 694 | NA | 6.49E−06 | 1.04E−05 | 1.01E−05 |
| Chondrosarcoma | CHSA | | 1.80E−08 | 1.58E−06 | 9.65E−06 |
| Osteosarcoma | OSA-FH | | 1.83E−07 | 8.60E−06 | NA |

Methodology: MTS. 4-Parameter Curve Fit w/SoftMax. Values are Molar
NA = not active TABLE 2-continued Cytotoxicity of Spisulosine Analogs (IC50, Molar)

| Solid Tumors | Line | 57 (H₃₁C₁₅, OH, NH₂) | 124 (H₂₉C₁₄, OH, NH₃⁺Cl⁻) | 126 (H₃₁C₁₅, O, NH₃⁺Cl⁻) | 129 (H₃₃C₁₆, O, NH₃⁺Cl⁻) |
|---|---|---|---|---|---|
| Bladder | 5637 | 7.80E−06 | 3.26E−06 | NA | 2.99E−05 |
| Breast | MX-1 | | NA | 2.84E−06 | 1.49E−05 |
| Colon | HT-29 | 9.11E−06 | NA | | NA |
| Gastric | Hs746t | | | NA | |
| Liver | SK-HEP-1 | | | NA | |
| NSCL | A549 | 1.03E−05 | 4.90E−05 | NA | NA |
| Ovary | SK-OV-3 | | | NA | |
| Pancreas | PANC-1 | 1.86E−07 | NA | NA | NA |
| Pharynx | FADU | 2.25E−07 | 1.96E−05 | NA | NA |
| Prostate | PC-3 | 1.02E−05 | | | |
| Prostate | DU-145 | 7.55E−08 | | NA | |
| Prostate | LNCAP | 6.35E−06 | | NA | |
| Renal | 786-O | | NA | 1.62E−07 | NA |
| SCL | NCI-H187 | 7.29E−06 | | 3.55E−06 | |
| Retinoblastoma | Y-79 | 9.51E−06 | | 1.21 E−05 | |
| Melanoma | Mel-28 | 9.4E−06 | NA | NA | NA |
| Fibrosarcoma | SW 694 | 7.57E−06 | | | |
| Chondrosarcoma | CHSA | 8.94E−06 | NA | NA | NA |
| Osteosarcoma | OSA-FH | 8.52E−06 | NA | NA | 1.49E−05 |

| Solid Tumors | Line | 131 (H₃₅C₁₇, O, NH₃⁺Cl⁻) | 133 (H₃₁C₁₅, O, Et, NH₃⁺Cl⁻) | 141 (H₃₁C₁₅, OH, F, NH₂) |
|---|---|---|---|---|
| Bladder | 5637 | NA | 1.58E−06 | 1.45E−06 |
| Breast | MX-1 | NA | 1.72E−06 | 4.29E−06 |
| Colon | HT-29 | NA | NA | |
| Gastric | Hs746t | | | 1.62E−05 |
| Liver | SK-HEP-1 | | | 1.55E−05 |
| NSCL | A549 | 2.01E−05 | NA | |
| Ovary | SK-OV-3 | | | NA |
| Pancreas | PANC-1 | NA | NA | |
| Pharynx | FADU | 1.43E−05 | 2.99E−06 | 3.96E−06 |
| Prostate | PC-3 | | | 2.18E−05 |
| Prostate | DU-145 | | | 4.95E−08 |
| Prostate | LNCAP | | | NA |
| Renal | 786-O | NA | 5.98E−05 | 3.30E−06 |
| SCL | NCI-H187 | | | |
| Retinoblastoma | Y-79 | | | 1.65E−06 |
| Melanoma | Mel-28 | NA | NA | 2.54E−06 |
| Fibrosarcoma | SW 694 | | | |
| Chondrosarcoma | CHSA | NA | NA | 4.62E−06 |
| Osteosarcoma | OSA-FH | NA | NA | |

Methodology: MTS. 4-Parameter Curve Fit w/SoftMax. Values are Molar

NA = not active

TABLE 3

Cytotoxicity of Spisulosine Analogs (IC50, Molar)

Compounds (top row):
- 1: $H_{31}C_{15}$-CH(OH)-CH($NH_2$)-CH$_3$
- 2: $H_{33}C_{16}$-CH(OH)-CH($NH_2$)-CH$_3$
- 3: $H_{35}C_{17}$-CH(OH)-CH($NH_2$)-CH$_3$
- 37: $H_{29}C_{14}$-CH(OH)-CH($NH_2$)-CH$_3$

| Leukemias/Lymphomas | Line | 1 | 2 | 3 | 37 |
|---|---|---|---|---|---|
| ALL (Promyelocytic leukemia) | HL-60 | 4.25E−07 | | | |
| ALL (Acute lymphobalstic) | Molt 3 | | 1.12E−06 | 7.61E−06 | 9.83E−09 |
| CML (Chronic myelogenous) | K562 | 7.84E−07 | | | |
| ALL (B-cell) | CCRF-SB | NA | | | |
| Leukemia (Hairy B-cell) | Mo-B | | | | |
| Leukemia (Plasma cell) | ARH-77 | 6.82E−07 | | | |
| Lymphoma (T cell) | H9 | 1.55E−06 | | | |
| Lymphoma (Cutaneous T cell) | Hut 78 | 2.16E−06 | 1.06E−05 | NA | 8.81E−06 |
| Lymphoma (undifferentiated) | MC116 | | 8.82E−06 | 1.09E−05 | 9.58E−06 |
| Lymphoma (Burkitts B cell) | RAMOS | 2.14E−06 | | | |
| Lymphoma (Histiocytic) | U-937 | 9.81E−07 | 2.98E−08 | NA | |
| Lymphoma (B cell) | CCRF-SB | | | | |
| Lymphoma (B cell) | MoB | | | | |
| Lymphoma (Burkitts ascites) | P3HR1 | 3.37E−06 | | | |

Methodology: MTS. 4-Parameter Curve Fit w/SoftMax. Values are Molar
NA = not active Compounds:
- 57: $H_{31}C_{15}$-CH(OH)-CH($NH_2$)-CH$_2$CH$_3$
- 124: $H_{29}C_{14}$-CH(OH)-CH($NH_3^+Cl^-$)-CH$_3$
- 126: $H_{31}C_{15}$-C(=O)-CH($NH_3^+Cl^-$)-CH$_3$
- 129: $H_{33}C_{16}$-C(=O)-CH($NH_3^+Cl^-$)-CH$_3$

| Leukemias/Lymphomas | Line | 57 | 124 | 126 | 129 |
|---|---|---|---|---|---|
| ALL (Promyelocytic leukemia) | HL-60 | | | | |
| ALL (Acute lymphobalstic) | Molt 3 | 3.76E−08 | 2.61E−05 | | NA |
| CML (Chronic myelogenous) | K562 | | | 0.001 | |
| ALL (B-cell) | CCRF-SB | | | | |
| Leukemia (Hairy B-cell) | Mo-B | | | | |
| Leukemia (Plasma cell) | ARH-77 | | | | |
| Lymphoma (T cell) | H9 | | NA | NA | NA |
| Lymphoma (Cutaneous T cell) | Hut 78 | 9.15E−06 | | | |
| Lymphoma (undifferentiated) | MC116 | NA | NA | | NA |
| Lymphoma (Burkitts B cell) | RAMOS | | NA | | NA |
| Lymphoma (Histiocytic) | U-937 | | NA | | NA |
| Lymphoma (B cell) | CCRF-SB | | | | |
| Lymphoma (B cell) | MoB | | | | |
| Lymphoma (Burkitts ascites) | P3HR1 | | | | |

Compounds:
- 131: $H_{35}C_{17}$-C(=O)-CH($NH_3^+Cl^-$)-CH$_3$
- 133: $H_{31}C_{15}$-C(=O)-CH($NH_3^+Cl^-$)-Et
- 141: $H_{31}C_{15}$-CH(OH)-CH($NH_2$)-CH$_2$F

| Leukemias/Lymphomas | Line | 131 | 133 | 141 |
|---|---|---|---|---|
| ALL (Promyelocytic leukemia) | HL-60 | | | 1.29E−06 |
| ALL (Acute lymphobalstic) | Molt 3 | 1.43E−05 | 5.81E−07 | |
| CML (Chronic myelogenous) | K562 | | | |
| ALL (B-cell) | CCRF-SB | | | |
| Leukemia (Hairy B-cell) | Mo-B | | | |
| Leukemia (Plasma cell) | ARH-77 | | | |
| Lymphoma (T cell) | H9 | 2.59E−06 | 5.98E−06 | |
| Lymphoma (Cutaneous T cell) | Hut 78 | | | |
| Lymphoma (undifferentiated) | MC116 | NA | NA | |
| Lymphoma (Burkitts B cell) | RAMOS | 1.65E−06 | 1.21E−06 | |
| Lymphoma (Histiocytic) | U-937 | NA | NA | |
| Lymphoma (B cell) | CCRF-SB | | | |

TABLE 3-continued

Cytotoxicity of Spisulosine Analogs (IC50, Molar)

| | | $H_{31}C_{15}$ structure | $H_{33}C_{16}$ structure | $H_{35}C_{17}$ structure | $H_{29}C_{14}$ structure |
|---|---|---|---|---|---|
| Leukemias/Lymphomas | Line | 1 | 2 | 3 | 37 |
| Lymphoma (B cell) | MoB | | | | |
| Lymphoma (Burkitts ascites) | P3HR1 | | | | |

Methodology: MTS. 4-Parameter Curve Fit w/SoftMax. Values are Molar
NA = not active

Experimental Section

General Procedures

All solvents were reagent grade (used in work-ups) or HPLC grade (used as reaction and/or as purification solvent). Anhydrous solvents were used directly as supplied by the manufacturer. All other reagents were commercial compounds of the highest purity available. All amino acids and their derivatives used as starting materials were commercially available. Compounds 1 and 39 were described in the International Patent WO 99/52521. Analytical thin-layer chromatography (TLC) was performed on Merck silica gel aluminium sheets (60, F254) precoated with a fluorescent indicator. Visualization was effected using ultraviolet light (254 nm), phosphomolybdic acid (7% w/v) in 95% ethanol. Proton and carbon magnetic resonance spectra ($^1$H, $^{13}$C-NMR) were recorded on a Varian-300 (300 MHz) Fourier transform spectrometer, and chemical shifts were expressed in parts per million (ppm) relative to $CHCl_3$ as an internal reference (7.26 ppm for $^1$H and 77.0 for $^{13}$C). Multiplicities are designated as singlet (s), doublet (d), doublet of doublets (dd), doublet of triplets (dt), triplet (t), quartet (q), quintet (quint), multiplet (m), and broad singlet (br s). Electrospray ionization mass spectra (ESI-MS) were obtained on a Hewlett Packard Series 1100 MSD. Flash column chromatography was carried out on E. Merck silica gel 60 (240–400 mesh) using the solvent systems listed under individual experiments.

EXAMPLES OF THE INVENTION

Illustrative examples of the synthesis of spisulosine derivatives according to the present invention are as follows:

Example 1

(S)-2-(N,N-Dibenzylamino)-propionaldehyde, 4

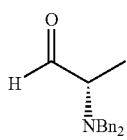

To a cold (−78° C.) solution of $(COCl)_2$ (2M in $CH_2Cl_2$, 2.47 mL, 4.94 mmol) in $CH_2Cl_2$ (8 mL), DMSO (0.70 mL, 9.89 mmol) was added dropwise. After stirring at −78° C. for 15 min, a solution of (S)-2-(N,N-dibenzylamino)-1-propanol (1.01 g, 3.96 mmol) in $CH_2Cl_2$ (10 mL) was added dropwise. The mixture was stirred at −78° C. for 1 h, and then $Et_3N$ (2.76 mL, 19.78 mmol) was added. The reaction was warmed up to 0° C. and stirred for 15 min, followed by the addition of $NH_4Cl$ (25 mL, sat. aq.). The crude was extracted with $CH_2Cl_2$ (3×25 mL), washed successively with $NaHCO_3$ (50 mL, sat. aq.) and brine (50 mL), dried over $Na_2SO_4$ and concentrated in vacuo. Aldehyde 4 was obtained as a yellow oil and used without further purification (928 mg, 93% yield).

$R_f$ 0.57 (hexane/EtOAc 5:1);

$^1$H NMR (300 MHz, $CDCl_3$) δ 1.18 (d, 3H, J=6.7 Hz), 3.33 (q, 1H, J=6.7 Hz), 3.57 (d, 2H, J=13.8 Hz), 3.74 (d, 2H, J=13.6 Hz), 7.23–7.42 (m, 10H), 9.73 (s, 1H);

$^{13}$C NMR (75 MHz, $CDCl_3$) δ 6.8, 54.9, 62.8, 127.3, 128.4, 128.8, 139.0, 204.5.

Exampl 2

(S)-2-(N,N-Dibenzylamino)-1-butan 1, 5

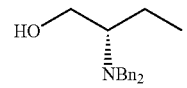

To a solution of (S)-2-amino-1-butanol (1.0 mL, 10.58 mmol) in MeOH (20 mL), BnBr (5.0 mL, 42.32 mmol) and $K_2CO_3$ (5.85 g, 42.32 mmol) were added. The mixture was stirred at 60° C. for 5 h, and then cooled down to room temperature and filtered, washing the solid with EtOAc. The filtrates were concentrated in vacuo and the residue purified by column chromatography on silica (100% hexane to hexane/EtOAc 5:1) to obtain alcohol 5 as a white solid (2.7 g, 95% yield).

$R_f$ 0.26 (hexane/EtOAc 5:1);

$^1$H NMR (300 MHz, $CDCl_3$) δ 0.98 (t, 3H, J=7.5 Hz), 1.25–1.37 (m, 1H), 1.79–1.89 (m, 1H), 2.74–2.83 (m, 1H), 3.31 (br s, 1H), 3.45–3.52 (m, 1H), 3.50 (d, 2H, J=13.1 Hz), 3.55–3.65 (m, 1H), 3.88 (d, 2H, J=13.3 Hz), 7.26–7.41 (m, 10H);

$^{13}$C NMR (75 MHz, $CDCl_3$) δ 11.6, 17.8, 53.0, 60.4, 127.0, 128.3, 128.8, 139.3.

Example 3

(S)-2-(N,N-Dibenzylamino)-butyraldehyde, 6

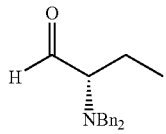

According to the method of Example 1, from alcohol 5 (1.0 g, 3.7 mmol), aldehyde 6 was obtained as a yellow oil and used without further purification (1.0 g, 100% yield).

$R_f$ 0.73 (hexane/Et$_2$O 1:1);

$^1$H NMR (300 MHz, CDCl$_3$) δ 0.97 (t, 3H, J=7.5 Hz), 1.64–1.85 (m, 2H), 3.08 (t, 1H, J=6.8 Hz), 3.72 (d, 2H, J=13.6 Hz), 3.80 (d, 2H, J=13.8 Hz), 7.22–7.39 (m, 10H), 9.73 (s, 1H).

Example 4

(S)-2-(N-Benzyloxycarbonylamino)-1-butanol, 7

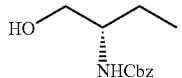

To a cold (0° C.) solution of (S)-2-amino-1-butanol (2.0 g, 22.5 mmol) in acetone/H$_2$O 1:1 (50 mL), Na$_2$CO$_3$ (8.7 g, 81.9 mmol) and BnOCOCl (5.8 g, 33.8 mmol) were added. After stirring at 0° C. for 1 h, the solid was filtered off and washed with acetone (2×30 mL). The filtrates were concentrated in vacuo and the residue was purified by column chromatography on silica (100% CH$_2$Cl$_2$ to CH$_2$Cl$_2$/MeOH 20:1) to obtain alcohol 7 as a white solid (2.14 g, 43% yield).

Example 5

(S)-2-(N-Benzyloxycarbonylamino)-butyraldehyde, 8

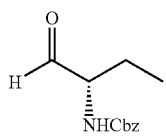

According to the method of Example 1, from alcohol 7 (750 mg, 3.4 mmol), aldehyde 8 was obtained as a yellow oil and used without further purification (700 mg, 94% yield).

$R_f$ 0.31 (MeOH/CH$_2$Cl$_2$ 3:1).

Example 6

Benzyl (S)-2-(N,N-dibenzylamino)-pentanoate, 9

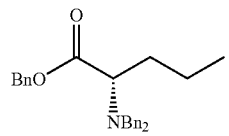

To a solution of L-norvaline (685 mg, 5.85 mmol) in MeCN (15 mL), BnBr (3.48 mL, 29.24 mmol) and K$_2$CO$_3$ (4.04 g, 29.24 mmol) were added. The mixture was stirred at 60° C. for 9 h, and then cooled down to room temperature and filtered, washing the solid with EtOAc. The filtrates were concentrated in vacuo and the residue purified by column chromatography on silica (100% hexane to hexane/EtOAc 5:1) to obtain benzyl ester 9 as a colorless oil (1.6 g, 71% yield).

$R_f$ 0.29 (hexane/EtOAc 5:1);

$^1$H NMR (300 MHz, CDCl$_3$) δ 0.82 (t, 3H, J=7.4 Hz), 1.25–1.40 (m, 1H), 1.45–1.60 (m, 1H), 1.70–1.85 (m, 2H), 3.42 (dd, 1H, J=8.2, 6.7 Hz), 3.55 (d, 2H, J=13.9 Hz), 3.96 (d, 2H, J=13.9 Hz), 5.18 (d, 1H, J=12.3 Hz), 5.30 (d, 1H, J=12.3 Hz), 7.25–7.45 (m, 15H);

$^{13}$C NMR (75 MHz, CDCl$_3$) δ 13.7, 19.3, 31.6, 54.4, 60.5, 65.8, 126.8, 128.1, 128.2, 128.4, 128.5, 128.8, 136.1, 139.7, 173.0.

Example 7

(S)-2-(N,N-Dibenzylamino)-1-pentanol, 10

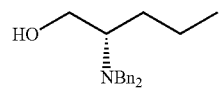

To a cold (0° C.) suspension of LiAlH$_4$ (184 mg, 4.84 mmol) in THF (10 mL), a solution of ester 9 (375 mg, 0.97 mmol) in THF (2.5 mL) was added. The mixture was stirred at 0° C. for 2 h, and then quenched by dropwise addition of EtOH (3 ml). Na—K tartrate solution (10% aq, 30 mL) was added, and the crude was extracted with EtOAc (3×30 mL), dried over Na$_2$SO$_4$, concentrated in vacuo and purified by column chromatography on silica (hexane/EtOAc 5:1) to obtain alcohol 10 as a colorless oil (170 mg, 62% yield).

$R_f$ 0.31 (hexane/EtOAc 5:1);

$^1$H NMR (300 MHz, CDCl$_3$) δ 0.97 (t, 3H, J=7.1 Hz), 1.17–1.42 (m, 3H), 1.71–1.76 (m, 1H), 2.80–2.86 (m, 1H), 3.25 (br s, 1H), 3.41–3.56 (m, 2H), 3.44 (d, 2H, J=13.3 Hz), 3.85 (d, 2H, J=13.3 Hz), 7.24–7.37 (m, 10H);

$^{13}$C NMR (75 MHz, CDCl$_3$) δ 14.3, 20.3, 27.2, 53.1, 58.7, 60.8, 127.1, 128.4, 129.0, 139.3.

Example 8

(S)-2-(N,N-Dibenzylamino)-pentanal, 11

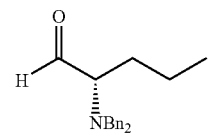

According to the method of Example 1, from alcohol 10 (163 mg, 0.58 mmol), aldehyde 11 was obtained as a yellow oil and used without further purification (140 g, 87% yield).

$R_f$ 0.73 (hexane/EtOAc 10:1);

$^1$H NMR (300 MHz, CDCl$_3$) δ 0.89 (t, 3H, J=7.3 Hz), 1.34–1.44 (m, 2H), 1.60–1.76 (m, 2H), 3.17 (t, 1H, J=6.7 Hz), 3.73 (d, 2H, J=13.8 Hz), 3.81 (d, 2H, J=13.8 Hz), 7.23–7.40 (m, 10H), 9.74 (s, 1H).

Example 9

Benzyl (S)-2-(N,N-dibenzylamino)-3-methylbutyrate, 12

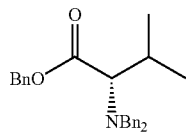

According to the method of Example 6, from L-valine (927 mg, 7.91 mmol), benzyl ester 12 was obtained as a colorless oil (2.58 g, 84% yield).

$R_f$ 0.31 (hexane/EtOAc 10:1);

$^1$H NMR (300 MHz, CDCl$_3$) δ 0.86 (d, 3H, J=6.4 Hz), 1.11 (d, 3H, J=6.5 Hz), 2.20–2.35 (m, 1H), 3.02 (d, 1H, J=10.7 Hz), 3.39 (d, 2H, J=13.9 Hz), 4.07 (d, 2H, J=13.9 Hz), 5.25 (d, 1H, J=12.3 Hz), 5.39 (d, 1H, J=12.1 Hz), 7.27–7.54 (m, 15H);

$^{13}$C NMR (75 MHz, CDCl$_3$) δ 19.5, 19.9, 27.2, 54.5, 65.6, 68.0, 126.9, 128.2, 128.3, 128.5, 128.6, 128.7, 136.1, 139.4, 171.8;

ESMS calcd for C$_{26}$H$_{30}$NO$_2$ (M+H) 388.2, found 388.2.

Example 10

(S)-2-(N,N-Dibenzylamino)-3-methyl-1-butanol, 13

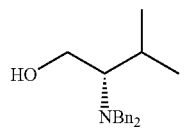

According to the method of Example 7, from ester 12 (2.3 g, 5.93 mmol), alcohol 13 was obtained as a colorless oil (1.55 g, 92% yield).

$R_f$ 0.24 (hexane/EtOAc 10:1);

$^1$H NMR (300 MHz, CDCl$_3$) δ 0.97 (dd, 3H, J=6.5, 1.2 Hz), 1.17 (dd, 3H, J=6.7, 1.2 Hz), 2.05–2.12 (m, 1H), 2.52–2.60 (m, 1H), 3.05 (br s, 1H), 3.47 (td, 1H, J=10.2, 1.3 Hz), 3.61 (br d, 1H, J=10.1 Hz), 3.71 (d, 2H, J=13.3 Hz), 3.91 (d, 2H, J=13.3 Hz), 7.23–7.36 (m, 10H);

$^{13}$C NMR (75 MHz, CDCl$_3$) δ 20.1, 22.6, 27.5, 54.1, 59.1, 64.6, 127.1, 128.4, 129.1, 139.6;

ESMS calcd for C$_{19}$H$_{26}$NO (M+H) 284.2, found 284.2.

Example 11

(S)-2-(N,N-Dibenzylamino)-3-methylbutyraldehyde, 14

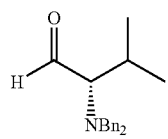

According to the method of Example 1, from alcohol 13 (450 mg, 1.59 mmol), aldehyde 14 was obtained as a yellow oil and used without further purification (447 mg, 100% yield).

$R_f$ 0.57 (hexane/EtOAc 5:1);

$^1$H NMR (300 MHz, CDCl$_3$) δ 0.87 (d, 3H, J=6.5 Hz), 1.08 (d, 3H, J=6.5 Hz), 2.25–2.32 (m, 1H), 2.72 (dd, 1H, J=10.2, 3.7 Hz), 3.70 (d, 2H, J=13.6 Hz), 4.02 (d, 2H, J=13.8 Hz), 7.24–7.38 (m, 10H), 9.85 (d, 1H, J=3.5 Hz).

Example 12

Benzyl (2S,3S)-2-(N,N-dibenzylamino)-3-methylpentanoate, 15

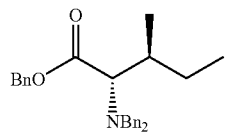

According to the method of Example 6, from L-isoleucine (1.0 g, 7.6 mmol), benzyl ester 15 was obtained as a colorless oil (2.4 g, 80% yield).

$R_f$ 0.62 (hexane/EtOAc 20:1);

$^1$H NMR (300 MHz, CDCl$_3$) δ 0.71–0.79 (m, 6H), 1.09–1.21 (m, 1H), 1.82–2.01 (m, 2H), 3.02 (d, 1H, J=6.5 Hz), 3.23 (d, 2H, J=9.5 Hz), 3.89 (d, 2H, J=9.5 Hz), 5.15 (d, 1H, J=7.5 Hz), 5.24 (d, 1H, J=7.5 Hz), 7.11–7.46 (m, 15H);

ESMS calcd for C$_{27}$H$_{32}$NO$_2$ (M+H) 402.2, found 402.5.

Example 13

(2S,3S)-2-(N,N-Dibenzylamino)-3-methyl-1-pentanol, 16

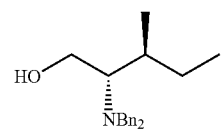

According to the method of Example 7, from ester 15 (0.50 g, 1.23 mmol), alcohol 16 was obtained as a colorless oil (0.36 g, 99% yield).

$R_f$ 0.43 (hexane/EtOAc 9:1);

$^1$H NMR (300 MHz, CDCl$_3$) δ 0.92–0.99 (m, 6H), 1.13–1.18 (m, 1H), 1.63–1.67 (m, 1H), 1.88–1.97 (m, 1H), 2.63–2.67 (m, 1H), 3.45 (d, 2H, J=6.5 Hz), 3.49 (d, 2H, J=9.5 Hz), 3.88 (d, 2H, J=9.5 Hz), 7.18–7.42 (m, 10H);

$^{13}$C NMR (75 MHz, CDCl$_3$) δ 11.4, 15.8, 28.2, 32.7, 53.9, 58.7, 62.7, 127.0, 128.3, 129.0, 139.7;

ESMS calcd for C$_{20}$H$_{28}$NO (M+H) 298.4, found 298.4.

Example 14

(2S,3S)-2-(N,N-Dibenzylamino)-3-methylpentanal, 17

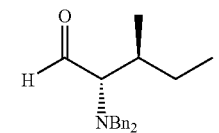

According to the method of Example 1, from alcohol 16 (479 mg, 1.61 mmol), aldehyde 17 was obtained as a yellow oil and used without further purification (470 mg, 98% yield).

$R_f$ 0.71 (hexane/EtOAc 9:1);

$^1$H NMR (300 MHz, CD$_3$OD) δ 0.78–0.82 (m, 6H), 1.13–1.20 (m, 1H), 1.80–1.85 (m, 1H), 2.02–2.10 (m, 1H), 2.71 (dd, 1H, J=7.8, 3.5 Hz), 3.61 (d, 2H, J=11.8 Hz), 3.99 (d, 2H, J=11.8 Hz), 7.15–7.29 (m, 10H), 9.77 (d, 1H, J=2.0 Hz).

Example 15

Benzyl (S)-3-(4'-benzyloxyphenyl)-2-(N,N-dibenzylamino)-propionate, 18

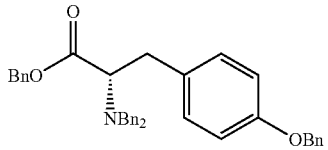

According to the method of Example 6, from L-tyrosine (1.49 g, 8.22 mmol), ester 18 was obtained as a colorless oil (2.10 g, 47% yield).

$R_f$ 0.25 (hexane/EtOAc 10:1);

$^1$H NMR (300 MHz, CDCl$_3$) δ 3.06 (dd, 1H, J=14.0, 8.1 Hz), 3.20 (dd, 1H, J=14.0, 7.6 Hz), 3.65 (d, 2H, J=13.9 Hz), 3.79 (t, 1H, J=7.7 Hz), 4.04 (d, 2H, J=13.9 Hz), 5.15 (s, 2H), 5.22 (d, 1H, J=12.2 Hz), 5.33 (d, 1H, J=12.2 Hz), 6.94 (d, 2H, J=8.8 Hz), 7.03 (d, 2H, J=8.5 Hz), 7.26–7.57 (m, 20H);

$^{13}$C NMR (75 MHz, CDCl$_3$) δ 34.7, 54.3, 62.5, 65.9, 69.9, 102.1, 114.5, 126.8, 127.4, 127.8, 128.1, 128.2, 128.4, 128.5, 128.5, 128.6, 130.3, 135.9, 137.1, 139.2, 157.3, 172.1;

ESMS calcd for $C_{37}H_{36}NO_3$ (M+H) 542.3, found 542.3.

Example 16

(S)-3-(4'-Benzyloxyphenyl)-2-(N,N-dibenzylamino)-1-propanol, 19

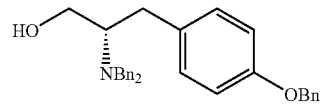

According to the method of Example 7, from ester 18 (1.90 g, 3.51 mmol), alcohol 19 was obtained as a colorless oil (1.20 g, 78% yield).

$R_f$ 0.15 (hexane/EtOAc 5:1);

$^1$H NMR (300 MHz, CDCl$_3$) δ 2.45 (dd, 1H, J=14.6, 10.7 Hz), 3.05–3.15 (m, 3H), 3.44 (br s, 1H), 3.52–3.60 (m, 1H), 3.55 (d, 2H, J=13.3 Hz), 3.98 (d, 2H, J=13.3 Hz), 5.10 (s, 2H), 6.97 (d, 2H, J=8.6 Hz), 7.08 (d, 2H, J=8.4 Hz), 7.29–7.52 (m, 15H);

$^{13}$C NMR (75 MHz, CDCl$_3$) δ 30.8, 53.1, 60.3, 60.8, 69.9, 114.9, 127.2, 127.3, 127.8, 128.4, 128.5, 128.9, 129.8, 131.3, 137.0, 139.1, 157.2;

ESMS calcd for $C_{30}H_{32}NO_2$ (M+H) 438.2, found 438.3.

Example 17

(S)-2-(N,N-dibenzylamino)-3-(4'-benzyloxyphenyl)-propionaldehyde, 20

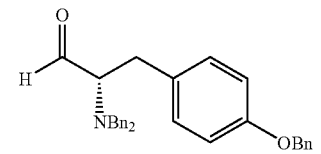

According to the method of Example 1, from alcohol 19 (600 mg, 1.37 mmol), aldehyde 20 was obtained as a yellow oil and used without further purification (597 mg, 100% yield).

$R_f$ 0.38 (hexane/EtOAc 5:1);

$^1$H NMR (300 MHz, CDCl$_3$) δ 2.89 (dd, 1H, J=14.1, 6.1 Hz), 3.09 (dd, 1H, J=14.1, 7.2 Hz), 3.51 (t, 1H, J=6.8 Hz), 3.67 (d, 2H, J=13.8 Hz), 3.82 (d, 2H, J=13.8 Hz), 5.06 (s, 2H), 6.88 (d, 2H, J=8.7 Hz), 7.06 (d, 2H, J=8.6 Hz), 7.22–7.45 (m, 15H), 9.72 (s, 1H).

Example 18

Methyl (S)-2,5-bis-(N,N-dibenzylamin)-pentanoate, 21

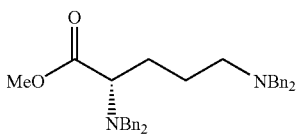

According to the method of Example 6, from L-ornithine methyl ester (1.20 g, 5.48 mmol), ester 21 was obtained as a colorless oil (2.18 g, 79% yield).

$R_f$ 0.27 (hexane/EtOAc 5:1);

$^1$H NMR (300 MHz, CDCl$_3$) δ 1.50–1.60 (m, 1H), 1.75–1.90 (m, 3H), 2.41 (t, 2H, J=6.7 Hz), 3.36 (t, 1H, J=7.3 Hz), 3.55 (d, 2H, J=13.8 Hz), 3.63 (d, 2H, J=13.9 Hz), 3.65 (d, 2H, J=13.6 Hz), 3.84 (s, 3H), 4.02 (d, 2H, J=13.8 Hz), 7.29–7.45 (m, 20H);

$^{13}$C NMR (75 MHz, CDCl$_3$) δ 23.6, 27.2, 50.8, 52.9, 54.5, 58.2, 60.6, 126.7, 126.9, 128.0, 128.1, 128.7, 128.8, 139.6, 139.7, 173.4;

ESMS calcd for $C_{34}H_{39}N_2O_2$ (M+H) 507.3, found 507.3.

Example 19

(S)-2,5-Bis-(N,N-dibenzylamino)-1-pentanol, 22

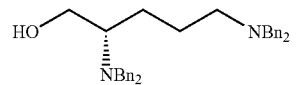

According to the method of Example 7, from ester 21 (1.75 g, 3.45 mmol), alcohol 22 was obtained as a colorless oil (1.50 g, 91% yield).

$R_f$ 0.27 (hexane/EtOAc 5:1);

$^1$H NMR (300 MHz, CDCl$_3$) δ 1.25–1.35 (m, 1H), 1.53–1.63 (m, 2H), 1.78–1.89 (m, 1H), 2.60 (t, 2H, J=6.8 Hz), 2.83–2.93 (m, 1H), 3.35 (br s, 1H), 3.53 (d, 2H, J=13.3 Hz), 3.54–3.64 (m, 2H), 3.70 (d, 2H, J=13.6 Hz), 3.76 (d, 2H, J=13.8 Hz), 3.93 (d, 2H, J=13.3 Hz), 7.36–7.59 (m, 20H);

$^{13}$C NMR (75 MHz, CDCl$_3$) δ 22.7, 24.6, 53.0, 53.6, 58.4, 58.9, 60.7, 126.7, 127.0, 128.0, 128.2, 128.6, 128.8, 139.2, 139.6;

ESMS calcd for $C_{33}H_{39}N_2O$ (M+H) 479.3, found 479.3.

Example 20

(S)-2,5-Bis-(N,N-dibenzylamino)-pentanal, 23

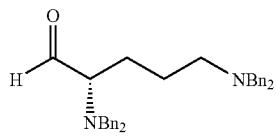

According to the method of Example 1, from alcohol 22 (505 mg, 1.05 mmol), aldehyde 23 was obtained as a yellow oil and used without further purification (503 mg, 100% yield).

$R_f$ 0.57 (hexane/EtOAc 5:1);
$^1$H NMR (300 MHz, CDCl$_3$) δ 1.30–1.40 (m, 1H), 1.55–1.70 (m, 2H), 1.75–1.85 (m, 1H), 2.35–2.45 (m, 2H), 3.02–3.08 (m, 1H), 3.52 (d, 2H, J=13.6 Hz), 3.62 (d, 2H, J=13.6 Hz), 3.71 (d, 2H, J=13.8 Hz), 3.81 (d, 2H, J=13.8 Hz), 7.28–7.41 (m, 20H), 9.69 (s, 1H).

Example 21

Methyl (R)-2-(N,N-dibenzylamino)-propionate, 24

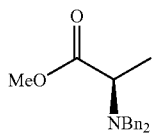

According to the method of Example 6, from D-alanine methyl ester (536 mg, 3.84 mmol), ester 24 was obtained as a colorless oil (625 mg, 57% yield).

$R_f$ 0.40 (hexane/EtOAc 10:1);
$^1$H NMR (300 MHz, CDCl$_3$) δ 1.35 (d, 3H, J=7.1 Hz), 3.53 (q, 1H, J=7.0 Hz), 3.65 (d, 2H, J=13.8 Hz), 3.75 (s, 3H), 3.85 (d, 2H, J=13.8 Hz), 7.22–7.42 (m, 10H).

Example 22

(R)-2-(N,N-dibenzylamino)-1-propanol, 25

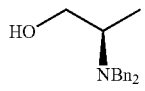

According to the method of Example 7, from ester 24 (625 mg, 2.20 mmol), alcohol 25 was obtained as a colorless oil (450 mg, 80% yield).

$R_f$ 0.21 (hexane/EtOAc 5:1);
$^1$H NMR (300 MHz, CDCl$_3$) δ 0.98 (d, 3H, J=7.1 Hz), 2.95–3.05 (m, 1H), 3.13 (br s, 1H), 3.35 (d, 2H, J=13.8 Hz), 3.40–3.55 (m, 2H), 3.81 (d, 2H, J=13.8 Hz), 7.19–7.41 (m, 10H).

Example 23

(R)-2-(N,N-Dibenzylamino)-propionaldehyde, 26

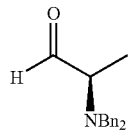

According to the method of Example 1, from alcohol 25 (475 mg, 1.86 mmol), aldehyde 26 was obtained as a yellow oil and used without farther purification (445 mg, 94% yield).

$R_f$ 0.57 (hexane/EtOAc 5:1);
$^1$H NMR (300 MHz, CDCl$_3$) δ 1.18 (t, 3H, J=6.7 Hz), 3.33 (q, 1H, J=6.7 Hz), 3.57 (d, 2H, J=13.8 Hz), 3.74 (d, 2H, J=13.6 Hz), 7.23–7.42 (m, 10H), 9.73 (s, 1H).

Example 24

(S)-2Benzyloxycarbonylamino)-1-propanol, 27

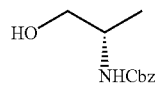

To a cold (−15° C.) solution of N-Cbz-L-alanine (1.0 g, 4.5 mmol) in THF (15 mL), Et$_3$N (360 mg, 4.5 mmol) and i-BuOCOCl (610 mg, 4.5 mmol) were added. After stirring at room temperature for 20 min, the solid Et$_3$N.HCl was filtered off and washed with THF. The filtrates were cooled to −15° C. and a solution of NaBH$_4$ (260 mg, 6.75 mmol) in H$_2$O (10 mL) was added. After 1 h, the reaction was quenched with H$_2$O (70 mL) and the THF removed in vacuo. The residue was extracted with EtOAc (3×30 mL), washed with brine (100 mL), dried over MgSO$_4$ and concentrated in vacuo to obtain alcohol 27 as a white solid (780 mg, 82% yield).

$^1$H NMR (500 MHz, CDCl$_3$) δ 1.15 (d, 3H, J=6.8 Hz), 2.75–2.80 (m, 2H), 3.45–3.55 (m, 1H), 3.60–3.65 (m, 1H), 3.80–3.85 (m, 1H), 5.09 (s, 2H), 7.30–7.35 (m, 5H).

Example 25

(S)-2-(N-Benzyloxycarbonylamino)-propionaldehyde, 28

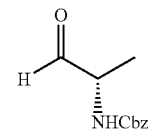

According to the method of Example 1, from alcohol 27 (750 mg, 3.6 mmol), aldehyde 28 was obtained as a yellow oil and used without further purification (680 mg, 92% yield).

$R_f$ 0.31 (MeOH/CH$_2$Cl$_2$ 3:1).

Example 26

(2S,3R)-2-(N,N-Dibenzylamino)-3-tetradecanol, 29

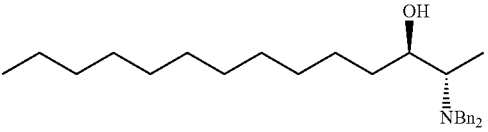

To a suspension of Mg (155 mg, 6.38 mmol) and a few crystals of I$_2$ in THF (3.1 mL), an aliquot of 1-bromoundecane (0.25 mL, 1.12 mmol) was added and the mixture was stirred at 60° C. until the red color of the solution disappeared. Then the remainder of 1-bromoundecane (0.46 mL, 2.07 mmol) was added and the reaction was stirred at room temperature for 1 h. The Grignard solution formed thereof was cooled down to 0° C. and a solution of aldehyde 4 (323.5 mg, 1.28 mmol) in THF (1.6 mL) was added via cannula. After stirring overnight at room temperature, the reaction was quenched with HCl (3N, 10 mL) extracted with EtOAc (3×10 mL), washed successively with NaHCO$_3$ (20 mL, sat. aq.) and brine (20 mL), dried over Na$_2$SO$_4$ and concentrated in vacuo. The crude was purified by column chromatography on silica (100% hexane to 10:1 hexane/EtOAc) to obtain a mixture of diastereoisomers. Further purification by HPLC on silica (95:5 to 80:20 hexane/MTBE) afforded pure anti alcohol 29 as a colorless oil (205 mg, 39% yield).

R$_f$ 0.50 (hexane/EtOAc 5:1);

$^1$H NMR (300 MHz, CDCl$_3$) δ 0.92 (t, 3H, J=6.9 Hz), 1.13 (d, 3H, J=6.9 Hz), 1.20–1.40 (m, 18H), 1.65–1.80 (m, 2H), 1.87 (br s, 1H), 2.74 (quint, 1H, J=6.7 Hz), 3.49 (d, 2H, J=13.9 Hz), 3.57–3.65 (m, 1H), 3.79 (d, 2H, J=13.8 Hz), 7.22–7.38 (m, 10H);

$^{13}$C NMR (75 MHz, CDCl$_3$) δ 8.6, 14.1, 22.7, 25.9, 29.3, 29.6, 29.6, 29.7, 31.9, 34.3, 54.8, 57.3, 73.7, 126.9, 128.2, 128.8, 140.2;

ESMS calcd for C$_{28}$H$_{44}$NO (M+H) 410.3, found 410.6.

Example 27

(2S,3R)-2-Amino-3-tetradecanol, 30

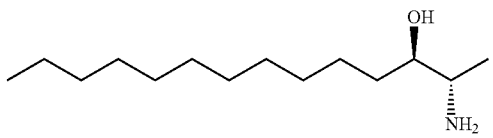

To a solution of N,N-dibenzylamine 29 (182 mg, 0.44 mmol) in MeOH (4.5 mL) at room temperature, Pd(OH)$_2$—C (20% wt, 24 mg, 0.04 mmol) was added. The mixture was purged with a stream of dry Ar, and then H$_2$. The reaction was stirred overnight under a H$_2$ atmosphere (1 atm). The catalyst was filtered off through a 0.45 µm teflon filter in polypropylene housing, washing the filter with MeOH (30 mL) and the solvent was evaporated in vacuo. The crude was purified by column chromatography on silica (90:10 CH$_2$Cl$_2$/MeOH to 100% MeOH) to obtain aminoalcohol 30 as a white solid (87 mg, 85% yield).

$^1$H NMR (300 MHz, CDCl$_3$) δ 0.87 (t, 3H, J=6.7 Hz), 1.03 (d, 3H, J=6.5 Hz), 1.20–1.40 (m, 18H), 1.45–1.55 (m, 2H), 2.66 (br s, 3H), 2.95–3.05 (m, 1H), 3.45–3.55 (m, 1H); $^{13}$C NMR (75 MHz, CDCl$_3$) δ 14.1, 16.2, 22.7, 26.2, 29.3, 29.6, 29.8, 31.9, 32.5, 50.5, 74.2;

ESMS calcd for C$_{14}$H$_{32}$NO (M+H) 230.2, found 230.4.

Example 28

(2S,3R)-2-(N,N-Dibenzylamino)-3-pentadecanol, 31

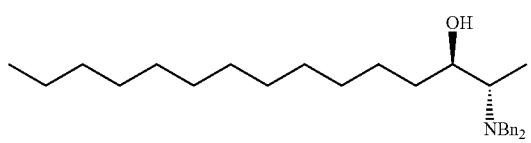

According to the method of Example 26, from aldehyde 4 (273 mg, 1.08 mmol) and 1-bromododecane (671 mg, 2.69 mmol), alcohol 31 was obtained as a colorless oil (195 mg, 43% yield).

R$_f$ 0.50 (hexane/EtOAc 5:1);

$^1$H NMR (300 MHz, CDCl$_3$) δ 0.90 (t, 3H, J=6.9 Hz), 1.12 (d, 3H, J=6.9 Hz), 1.20–1.40 (m, 20H), 1.65–1.75 (m, 2H), 1.82 (br s, 1H), 2.73 (quint, 1H, J=6.7 Hz), 3.48 (d, 2H, J=13.8 Hz), 3.57–3.65 (m, 1H), 3.78 (d, 2H, J=13.8 Hz), 7.21–7.37 (m, 10H); $^{13}$C NMR (75 MHz, CDCl$_3$) δ 8.6, 14.1, 22.7, 25.9, 29.3, 29.6, 29.6, 29.7, 31.9, 34.3, 54.8, 57.3, 73.7, 126.9, 128.2, 128.8, 140.2;

ESMS calcd for C$_{29}$H$_{46}$NO (M+H) 424.4, found 424.7.

Example 29

(2S,3R)-2-Amino-3-pentadecanol, 32

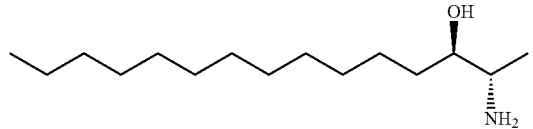

According to the method of Example 27, from N,N-dibenzylamine 31 (145 mg, 0.34 mmol), aminoalcohol 32 was obtained as a white solid (65 mg, 78% yield).

$^1$H NMR (300 MHz, CDCl$_3$) δ 0.87 (t, 3H, J=6.9 Hz), 1.02 (d, 3H, J=6.4 Hz), 1.20–1.40 (m, 20H), 1.45–1.55 (m, 2H), 2.38 (br s, 3H), 2.93–3.03 (m, 1H), 3.42–3.52 (m, 1H); $^{13}$C NMR (75 MHz, CDCl$_3$) δ 14.1, 16.4, 22.7, 26.2, 29.3, 29.6, 29.8, 31.9, 32.5, 50.5, 74.4;

ESMS calcd for C$_{15}$H$_{34}$NO (M+H) 244.3, found 244.4.

Example 30

(2S,3R)-2-(N,N-Dibenzylamino)-3-hexadecanol, 33

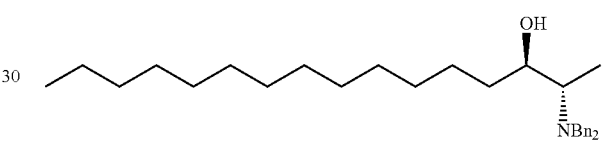

According to the method of Example 26, from aldehyde 4 (332 mg, 1.31 mmol) and 1-bromotridecane (863 mg, 3.28 mmol), alcohol 33 was obtained as a colorless oil (172 mg, 30% yield).

R$_f$ 0.50 (hexane/EtOAc 5:1);

$^1$H NMR (300 MHz, CDCl$_3$) δ 0.90 (t, 3H, J=6.9 Hz), 1.12 (d, 3H, J=6.9 Hz), 1.20–1.40 (m, 22H), 1.65–1.75 (m, 2H), 1.84 (br s, 1H), 2.73 (quint, 1H, J=6.5 Hz), 3.49 (d, 2H, J=13.8 Hz), 3.57–3.65 (m, 1H), 3.78 (d, 2H, J=13.8 Hz), 7.23–7.38 (m, 10H);

$^{13}$C NMR (75 MHz, CDCl$_3$) δ 8.6, 14.1, 22.7, 25.9, 29.3, 29.6, 29.7, 31.9, 34.3, 54.8, 57.3, 73.6, 126.8, 128.2, 128.7, 140.2;

ESMS calcd for C$_{30}$H$_{48}$NO (M+H) 438.4, found 438.7.

Example 31

(2S,3R)-2-Amino-3-hexadecanol, 34

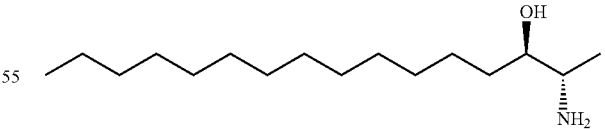

According to the method of Example 27, from N,N-dibenzylamine 33 (149 mg, 0.34 mmol), aminoalcohol 34 was obtained as a white solid (62 mg, 71% yield).

$^1$H NMR (300 MHz, CDCl$_3$) δ 0.87 (t, 3H, J=7.0 Hz), 1.05 (d, 3H, J=6.5 Hz), 1.20–1.40 (m, 22H), 1.45–1.55 (m, 2H), 2.95–3.10 (m, 4H), 3.48–3.58 (m, 1H); $^{13}$C NMR (75 MHz, CDCl$_3$) δ 14.1, 15.9, 22.7, 26.2, 29.3, 29.6, 29.7, 29.7, 31.9, 32.6, 50.6, 73.9;

ESMS calcd for C$_{16}$H$_{36}$NO (M+H) 258.3, found 258.5.

Example 32

(2S,3R)-2-Amino-3-hexadecanol hydrochloride, 35

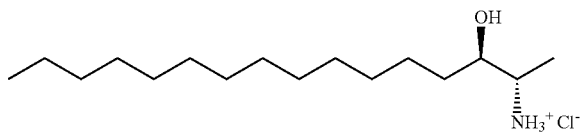

To a solution of amine 34 (26 mg, 0.10 mmol) in dioxane (0.5 mL), anhydrous HCl solution in dioxane (5.3M, 0.38 mL, 2.02 mmol) was added. After stirring at room temperature for 5 h, the solvent was removed in vacuo. The resulting solid was washed with dioxane to obtain hydrochloride 35 as a white solid (19 mg, 64% yield).

$^1$H NMR (300 MHz, CD$_3$OD) δ 0.90 (t, 3H, J=6.7 Hz), 1.21 (d, 3H, J=6.7 Hz), 1.25–1.40 (m, 22H), 1.45–1.60 (m, 2H), 3.27 (qd, 1H, J=6.7, 3.0 Hz), 3.65–3.73 (m, 1H);

$^{13}$C NMR (75 MHz, CD$_3$OD) δ 12.1, 14.4, 23.7, 27.0, 30.5, 30.6, 30.7, 30.7, 30.8, 33.1, 34.0, 52.6, 71.6;

ESMS calcd for C$_{16}$H$_{36}$NO (M−Cl) 258.3, found 258.4.

Example 33

(2S,3R)-2-(N,N-Dibenzylamino)-3-heptadecanol, 36

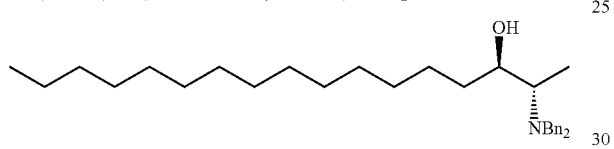

According to the method of Example 26, from aldehyde 4 (309 mg, 1.21 mmol) and 1-bromotetradecane (1.34 g, 4.84 mmol), alcohol 36 was obtained as a colorless oil (270 mg, 49% yield).

R$_f$ 0.50 (hexane/EtOAc 5:1);

$^1$H NMR (300 MHz, CDCl$_3$) δ 0.91 (t, 3H, V 6.9 Hz), 1.12 (d, 3H, J=6.7 Hz), 1.20–1.40 (m, 24H), 1.65–1.75 (m, 2H), 1.85 (br s, 1H), 2.73 (quint, 1H, J=7 6.4 Hz), 3.49 (d, 2H, J=13.9 Hz), 3.57–3.65 (m, 1H), 3.78 (d, 2H, J=13.8 Hz), 7.21–7.38 (m, 10H);

$^{13}$C NMR (75 MHz, CDCl$_3$) δ 8.6, 14.1, 22.7, 25.9, 29.3, 29.6, 29.7, 31.9, 34.4, 54.8, 57.3, 73.6, 126.9, 128.2, 128.8, 140.2;

ESMS calcd for C$_{31}$H$_{50}$NO (M+H) 452.4, found 452.5.

Example 34

(2S,3R)-2-Amino-3-heptadecanol, 37

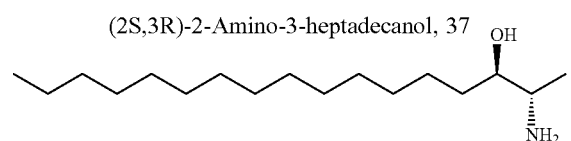

According to the method of Example 27, from N,N-dibenzylamine 36 (182 mg, 0.40 mmol), aminoalcohol 37 was obtained as a white solid (81 mg, 74% yield).

$^1$H NMR (300 MHz, CDCl$_3$) δ 0.88 (t, 3H, J=7.0 Hz), 1.02 (d, 3H, J=6.5 Hz), 1.20–1.40 (m, 24H), 1.45–1.55 (m, 2H), 1.85 (br s, 3H), 2.94–3.04 (m, 1H), 3.42–3.52 (m, 1H);

$^{13}$C NMR (75 MHz, CDCl$_3$) δ 14.1, 16.3, 22.7, 26.2, 29.3, 29.7, 31.9, 32.5, 50.4, 74.2;

ESMS calcd for C$_{17}$H$_{38}$NO (M+H) 272.3, found 272.3.

Example 35

(2S,3R)-2-Amino-3-heptadecanol hydrochloride, 38

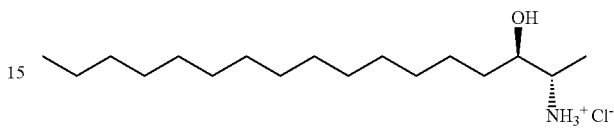

According to the method of Example 32, from aminoalcohol 37 (50 mg, 0.18 mmol), hydrochloride 38 was obtained as a white solid (41 mg, 73% yield).

$^1$H NMR (300 MHz, CD$_3$OD) δ 0.80 (t, 3H, J=6.8 Hz), 1.22 (d, 3H, J=6.8 Hz), 1.21–1.40 (m, 24H), 1.41–1.51 (m, 2H), 3.22–3.31 (m, 1H), 3.63–3.74 (m, 1H).

Example 36

Bis-((2S,3R)-2-ammonium-3-octadecanol) L-tartrate, 40

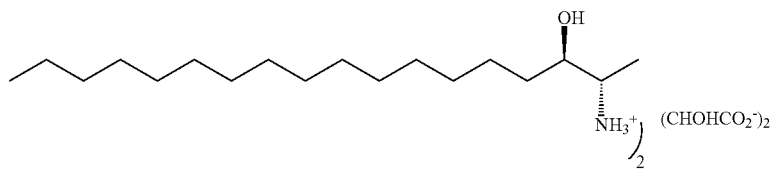

To a solution of aminoalcohol 1 (63 mg, 0.221 mmol) in MeOH (1.1 mL) at room temperature, L-tartaric acid (66 mg, 0.442 mmol) was added. After stirring for 16 h, the solvent was evaporated in vacuo. The resulting solid was washed with H$_2$O and dried under vacuum for 8 h to obtain tartrate 40 as a white solid (53 mg, 67% yield).

$^1$H NMR (300 MHz, CD$_3$OD) δ 0.90 (t, 3H, J=6.7 Hz), 1.21 (d, 3H, J=6.7 Hz), 1.25–1.40 (m, 26H), 1.40–1.55 (m, 2H), 3.26 (qd, 1H, J=6.7, 3.0 Hz), 3.62–3.72 (m, 1H), 4.43 (d, 2H, J=1.8 Hz);

$^{13}$C NMR (75 MHz, CD$_3$OD) δ 12.0, 14.4, 23.7, 27.0, 30.5, 30.8, 33.1, 34.0, 52.6, 71.7, 73.9;

ESMS calc for C$_{18}$H$_{40}$NO (M=CHOHCO$_2$) 286.3, found 286.2.

Example 37

(2S,3R)-2-Amino-3-octadecanol hydrochloride, 41

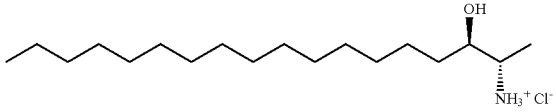

According to the method of Example 32, from aminoalcohol 1 (52.5 mg, 0.184 mmol), hydrochloride 41 was obtained as a white solid (52 mg, 88% yield).

$^1$H NMR (300 MHz, CD$_3$OD) δ 0.90 (t, 3H, J=6.7 Hz), 1.21 (d, 3H, J=6.7 Hz), 1.25–1.40 (m, 26H), 1.40–1.55 (m, 2H), 3.26 (qd, 1H, J=6.7, 3.0 Hz), 3.62–3.72 (m, 1H);
$^{13}$C NMR (75 MHz, CD$_3$OD) δ 12.1, 14.5, 23.7, 27.0, 30.5, 30.7, 30.7, 30.8, 33.1, 34.0, 52.6, 71.6;
ESMS calcd for C$_{18}$H$_{40}$NO (M−Cl) 286.3, found 286.2.

Example 38

(2S,3R)-2-(N,N-Dibenzylamino)-3-nonadecanol, 42

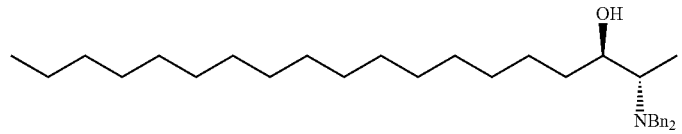

According to the method of Example 26, from aldehyde 4 (294 mg, 1.16 mmol) and 1-bromohexadecane (1.42 g, 4.64 mmol), alcohol 42 was obtained as a colorless oil (283 mg, 51% yield).

R$_f$ 0.50 (hexane/EtOAc 5:1);
$^1$H NMR (300 MHz, CDCl$_3$) δ 0.93 (t, 3H, J=6.9 Hz), 1.14 (d, 3H, J=6.7 Hz), 1.20–1.40 (m, 28H), 1.65–1.80 (m, 2H), 1.95 (br s, 1H), 2.75 (quint, 1H, J=6.5 Hz), 3.50 (d, 2H, J=13.8 Hz), 3.57–3.65 (m, 1H), 3.80 (d, 2H, J=13.8 Hz), 7.23–7.40 (m, 10H);
$^{13}$C NMR (75 MHz, CDCl$_3$) δ 8.6, 14.1, 22.7, 25.9, 29.3, 29.6, 29.7, 31.9, 34.3, 54.7, 57.2, 73.6, 126.8, 128.2, 128.7, 140.1;
ESMS calcd for C$_{33}$H$_{54}$NO (M+H) 480.4, found 480.5.

Example 39

(2S,3R)-2-Amino-3-nonadecanol, 2

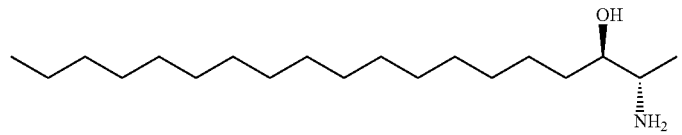

According to the method of Example 27, from N,N-dibenzylamine 42 (204 mg, 0.43 mmol), aminoalcohol 2 was obtained as a white solid (91 mg, 72% yield).

$^1$H NMR (300 MHz, CDCl$_3$) δ 0.88 (t, 3H, J=6.9 Hz), 1.01 (d, 3H, J=6.4 Hz), 1.20–1.40 (m, 28H), 1.45–1.55 (m, 2H), 1.77 (br s, 3H), 2.92–3.02 (m, 1H), 3.39–3.49 (m, 1H);
$^{13}$C NMR (75 MHz, CDCl$_3$) δ 14.1, 16.7, 22.7, 26.2, 29.3, 29.6, 29.7, 29.8, 31.9, 32.4, 50.3, 74.6;
ESMS calcd for C$_{19}$H$_{42}$NO (M+H) 300.3, found 300.3.

Example 40

(2S,3R)-2-Amino-3-nonadecanol hydrochloride, 43

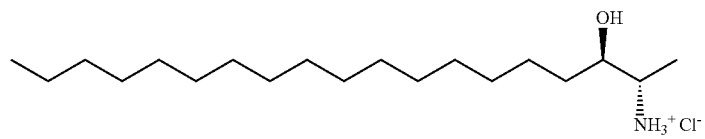

According to the method of Example 32, from aminoalcohol 2 (530 mg, 1.70 mmol), hydrochloride 43 was obtained as a white solid (454 mg, 76% yield).

$^1$H NMR (300 MHz, CD$_3$OD) δ 0.86 (t, 3H, J=6.8 Hz), 1.35 (d, 3H, J=6.8 Hz), 1.20–1.41 (m, 28H), 1.41–1.51 (m, 2H), 3.24–3.37 (m, 1H), 3.65–3.73 (m, 1H).

Example 41

(2S,3R)-2-(N,N-Dibenzylamino)-3-eicosanol, 44

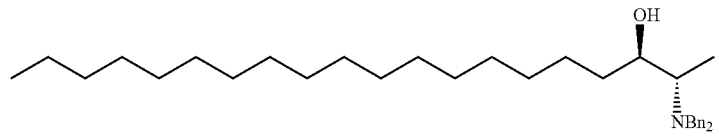

According to the method of Example 26, from aldehyde 4 (410 mg, 1.62 mmol) and 1-bromoheptadecane (2.07 g, 6.47 mmol), alcohol 44 was obtained as a colorless oil (427 mg, 53% yield).

R$_f$ 0.50 (hexane/EtOAc 5:1);

$^1$H NMR (300 MHz, CDCl$_3$) δ 0.93 (t, 3H, J=6.9 Hz), 1.14 (d, 3H, J=6.9 Hz), 1.20–1.40 (m, 30H), 1.65–1.80 (m, 2H), 1.94 (br s, 1H), 2.75 (quint, 1H, J=6.7 Hz), 3.51 (d, 2H, J=13.8 Hz), 3.56–3.64 (m, 1H), 3.80 (d, 2H, J=13.8 Hz), 7.23–7.40 (m, 10H);

$^{13}$C NMR (75 MHz, CDCl$_3$) δ 8.6, 14.1, 22.7, 25.9, 29.3, 29.6, 29.7, 31.9, 34.3, 54.8, 57.3, 73.6, 126.8, 128.2, 128.7, 140.2;

ESMS calcd for C$_{34}$H$_{56}$NO (M+H) 494.4, found 494.5.

Example 42

(2S,3R)-2-Amino-3-eicosanol, 3

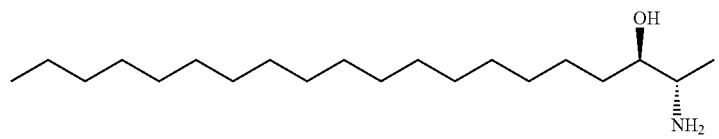

According to the method of Example 27, from N,N-dibenzylamine 44 (294 mg, 0.60 mmol), aminoalcohol 3 was obtained as a white solid (140 mg, 75% yield).

$^1$H NMR (300 MHz, CDCl$_3$) δ 0.88 (t, 3H, J=6.7 Hz), 1.00 (d, 3H, J=6.4 Hz), 1.20–1.40 (m, 30H), 1.45–1.55 (m, 2H), 1.70 (br s, 3H), 2.92–3.02 (m, 1H), 3.39–3.49 (m, 1H);

$^{13}$C NMR (75 MHz, CDCl$_3$) δ 14.1, 16.8, 22.7, 26.2, 29.3, 29.7, 29.8, 31.9, 32.5, 50.4, 74.7;

ESMS calcd for C$_{20}$H$_{44}$NO (M+H) 314.3, found 314.3.

Example 43

(2S,3R)-2-Amino-3-eicosanol hydrochloride, 45

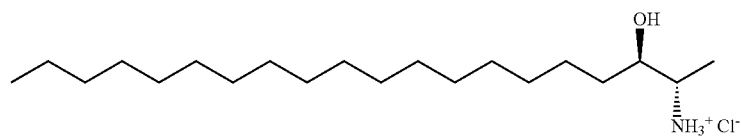

According to the method of Example 32, from aminoalcohol 3 (12 mg, 0.04 mmol), hydrochloride 45 was obtained as a white solid (11 mg, 82% yield).

$^1$H NMR (300 MHz, CD$_3$OD) δ 0.90 (t, 3H, J=6.5 Hz), 1.21 (d, 3H, J=6.7 Hz), 1.25–1.40 (m, 30H), 1.45–1.60 (m, 2H), 3.26 (qd, 1H, J=6.9, 3.0 Hz), 3.63–3.73 (m, 1H);

$^{13}$C NMR (75 MHz, CD$_3$OD) δ 12.1, 14.4, 23.7, 27.8, 30.5, 30.6, 30.8, 33.1, 34.0, 52.6, 71.7;

ESMS calcd for C$_{20}$H$_{44}$NO (M−Cl) 314.3, found 314.5.

Example 44

(2S,3R)-2-(N,N-Dibenzylamino)-3-heneicosanol, 46

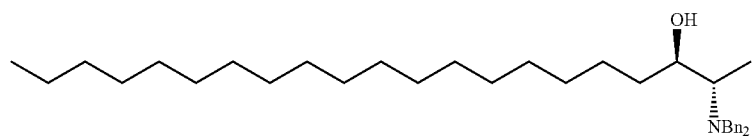

According to the method of Example 26, from aldehyde 4 (350 mg, 1.38 mmol) and 1-bromooctadecane (1.15 g, 3.45 mmol), alcohol 46 was obtained as a colorless oil (395 mg, 56% yield).

R$_f$ 0.50 (hexane/EtOAc 5:1);

$^1$H NMR (300 MHz, CDCl$_3$) δ 0.91 (t, 3H, J=6.9 Hz), 1.14 (d, 3H, J=6.9 Hz), 1.20–1.40 (m, 32H), 1.65–1.75 (m, 2H), 1.80 (br s, 1H), 2.75 (quint, 1H, J=6.7 Hz), 3.51 (d, 2H, J=13.9 Hz), 3.56–3.64 (m, 1H), 3.80 (d, 2H, J=13.8 Hz), 7.23–7.40 (m, 10H);

$^{13}$C NMR (75 MHz, CDCl$_3$) δ 8.6, 14.1, 22.7, 25.9, 29.3, 29.7, 31.9, 34.3, 54.8, 57.2, 73.6, 126.8, 128.2, 128.7, 140.1;

ESMS calcd for C$_{35}$H$_{58}$NO (M+H) 508.4, found 508.4.

Example 45

(2S,3R)-2-Amino-3-heneicosanol, 47

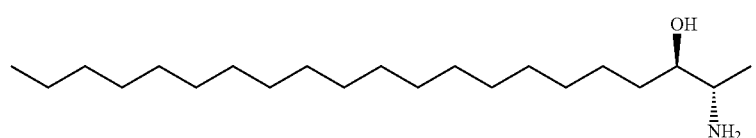

According to the method of Example 27, from N,N-dibenzylamine 46 (228 mg, 0.45 mmol), aminoalcohol 47 was obtained as a white solid (125 mg, 85% yield).

$^1$H NMR (300 MHz, CDCl$_3$) δ 0.87 (t, 3H, J7 6.9 Hz), 1.00 (d, 3H, J=6.5 Hz), 1.20–1.40 (m, 32H), 1.45–1.55 (m, 2H), 1.86 (br s, 3H), 2.92–3.02 (m, 1H), 3.39–3.49 (m, 1H);

$^{13}$C NMR (75 MHz, CDCl$_3$) δ 14.1, 16.8, 22.7, 26.2, 29.3, 29.7, 29.8, 31.9, 32.5, 50.4, 74.7;

ESMS calcd for C$_{21}$H$_{46}$NO (M+H) 328.3, found 328.3.

Example 46

(2S,3R)-2-Amino-3-heneicosanol hydrochloride, 48

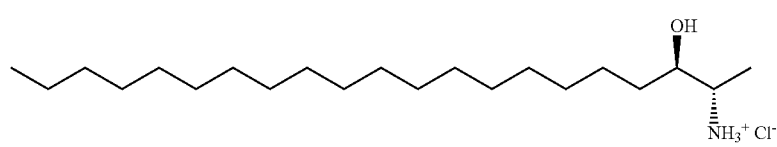

According to the method of Example 32, from aminoalcohol 47 (32.5 mg, 0.10 mmol), hydrochloride 48 was obtained as a white solid (32 mg, 89% yield).

$^1$H NMR (300 MHz, CD$_3$OD) δ 0.90 (t, 3H, J=6.6 Hz), 1.21 (d, 3H, J=6.9 Hz), 1.25–1.40 (m, 32H), 1.45–1.60 (m, 2H), 3.27 (qd, 1H, J=6.9, 3.0 Hz), 3.65–3.73 (m, 1H);

$^{13}$C NMR (75 MHz, CD$_3$OD) δ 12.1, 14.5, 23.8, 27.0, 30.5, 30.7, 30.7, 30.8, 33.1, 34.0, 52.6, 71.6;

ESMS calcd for C$_{21}$H$_{46}$NO (M−Cl) 328.3, found 328.5.

Example 47

(2S,3R)-2-(N,N-Dibenzylamino)-3-docosanol, 49

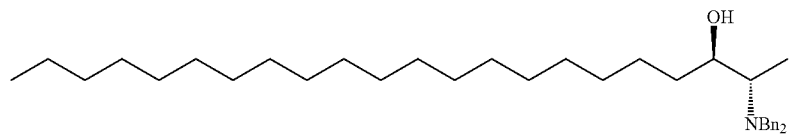

According to the method of Example 26, from aldehyde 4 (380 mg, 1.50 mmol) and 1-bromononadecane (1.30 g, 3.75 mmol), alcohol 49 was obtained as a colorless oil (349 mg, 45% yield).

R$_f$ 0.50 (hexane/EtOAc 5:1);

$^1$H NMR (300 MHz, CDCl$_3$) δ 0.91 (t, 3H, J=6.9 Hz), 1.14 (d, 3H, J=6.9 Hz), 1.20–1.40 (m, 34H), 1.65–1.75 (m, 2H), 1.81 (br s, 1H), 2.75 (quint, 1H, J=6.7 Hz), 3.51 (d, 2H, J=13.9 Hz), 3.56–3.64 (m, 1H), 3.80 (d, 2H, J=13.8 Hz), 7.23–7.40 (m, 10H);

$^{13}$C NMR (75 MHz, CDCl$_3$) δ 8.6, 14.1, 22.7, 25.9, 29.3, 29.7, 31.9, 34.3, 54.8, 57.2, 73.6, 126.8, 128.2, 128.7, 140.1;

ESMS calcd for C$_{36}$H$_{60}$NO (M+H) 522.5, found 522.4.

Example 48

(2S,3R)-2-Amino-3-docosanol, 50

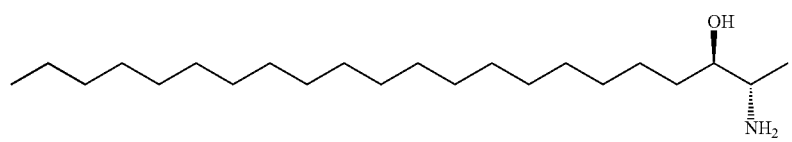

According to the method of Example 27, from N,N-dibenzylamine 49 (206 mg, 0.39 mmol), aminoalcohol 50 was obtained as a white solid (100 mg, 74% yield).

$^1$H NMR (300 MHz, CDCl$_3$) δ 0.87 (t, 3H, J=6.9 Hz), 1.00 (d, 3H, J=6.5 Hz), 1.20–1.40 (m, 34H), 1.45–1.55 (m, 2H), 1.65 (br s, 3H), 2.92–3.02 (m, 1H), 3.39–3.49 (m, 1H);

$^{13}$C NMR (75 MHz, CDCl$_3$) δ 14.1, 16.8, 22.7, 26.2, 29.3, 29.7, 29.8, 31.9, 32.5, 50.4, 74.7;

ESMS calcd for C$_{22}$H$_{48}$NO (M+H) 342.4, found 342.4.

Example 49

(2S,3R)-2-(N,N-Dibenzylamino)-3-tricosanol, 51

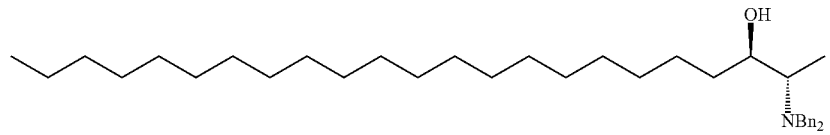

According to the method of Example 26, from aldehyde 4 (365 mg, 1.44 mmol) and 1-bromoeicosadecane (1.30 g, 3.60 mmol), alcohol 51 was obtained as a colorless oil (317 mg, 41% yield).

$R_f$ 0.50 (hexane/EtOAc 5:1);

$^1$H NMR (300 MHz, CDCl$_3$) δ 0.91 (t, 3H, J=6.9 Hz), 1.14 (d, 3H, J=6.9 Hz), 1.20–1.40 (m, 36H), 1.65–1.75 (m, 2H), 1.81 (br s, 1H), 2.75 (quint, 1H, J=6.7 Hz), 3.51 (d, 2H, J=13.9 Hz), 3.56–3.64 (m, 1H), 3.80 (d, 2H, J=13.8 Hz), 7.23–7.40 (m, 10H);

$^{14}$C NMR (75 MHz, CDCl$_3$) δ 8.6, 14.1, 22.6, 25.8, 9.3, 29.7, 31.9, 34.3, 54.7, 57.2, 73.6, 126.8, 128.2, 128.7, 140.1;

ESMS calcd for C$_{37}$H$_{62}$NO (M+H) 536.5, found 536.5.

Example 50

(2S,3R)-2-Amino-3-tricosanol, 52

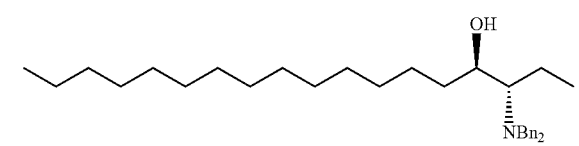

According to the method of Example 27, from N,N-dibenzylamine 51 (191 mg, 0.36 mmol), aminoalcohol 52 was obtained as a white solid (103 mg, 81% yield).

$^1$H NMR (300 MHz, CDCl$_3$) δ 0.87 (t, 3H, J=6.9 Hz), 1.00 (d, 3H, J=6.5 Hz), 1.20–1.40 (m, 36H), 1.45–1.55 (m, 2H), 1.65 (br s, 3H), 2.92–3.02 (m, 1H), 3.39–3.49 (m, 1H);

$^{13}$C NMR (75 MHz, CDCl$_1$) δ 14.1, 16.8, 22.7, 26.2, 29.3, 29.7, 29.8, 31.9, 32.5, 50.4, 74.7;

ESMS calcd for C$_{23}$H$_{50}$NO (M+H) 356.4, found 356.4.

Example 51

(3S,4R)-3-(N,N-Dibenzylamino)4octadecanol, 53

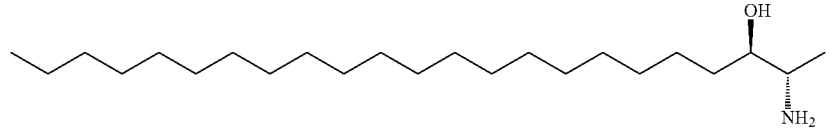

According to the method of Example 26, from aldehyde 6 (660 mg, 2.47 mmol) and 1-bromotetradecane (1.71 g, 6.17 mmol), alcohol 53 was obtained as a colorless oil (535 mg, 47% yield).

$R_f$ 0.50 (hexane/EtOAc 5:1);

$^1$H NMR (300 MHz, CDCl$_3$) δ 0.92 (t, 3H, J=6.6 Hz), 1.02 (t, 3H, J=7.4 Hz), 1.20–1.40 (m, 24H), 1.45–1.60 (m, 3H), 1.70–1.85 (m, 1H), 2.27 (br s, 1H), 2.62 (td, 1H, J=7.0, 4.2 Hz), 3.60–3.75 (m, 5H), 7.22–7.38 (m, 10H);

$^{13}$C NMR (75 MHz, CDCl$_3$) δ 12.3, 14.1, 18.1, 22.7, 26.6, 29.4, 29.6, 29.7, 31.9, 34.4, 55.2, 62.8, 70.6, 126.9, 128.2, 128.9, 140.1;

ESMS calcd for C$_{32}$H$_{52}$NO (M+H) 466.4, found 466.4.

Example 52

(3S,4R)-3-Amino-4-octadecanol, 54

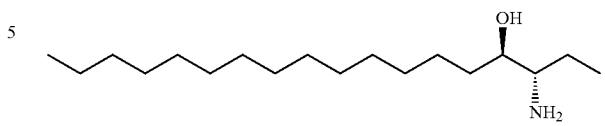

According to the method of Example 27, from N,N-dibenzylamine 53 (166 mg, 0.36 mmol), aminoalcohol 54 was obtained as a white solid (100 mg, 98% yield).

$^1$H NMR (300 MHz, CDCl$_3$) δ 0.89 (t, 3H, J=6.6 Hz), 1.00 (t, 3H, J=7.5 Hz), 1.20–1.40 (m, 26H), 1.45–1.60 (m, 2H), 2.05 (br s, 3H), 2.64–2.70 (m, 1H), 3.42–3.50 (m, 1H);

$^{13}$C NMR (75 MHz, CDCl$_3$) δ 11.0, 14.1, 22.7, 24.8, 26.2, 29.3, 29.6, 29.7, 29.8, 31.5, 31.9, 57.1, 74.0;

ESMS calcd for C$_{18}$H$_{40}$NO (M+H) 286.3, found 286.2.

Example 53

(3s,4R)-3-Amino-4-octadecanol hydrocloride, 55

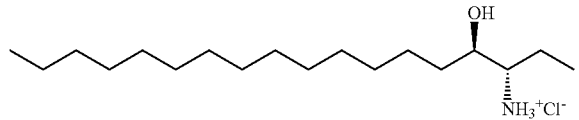

According to the method of Example 32, from aminoalcohol 54 (52 mg, 0.18 mmol), hydrochloride 55 was obtained as a white solid (38 mg, 65% yield).

$^1$H NMR (300 MHz, CD$_3$OD) δ 0.90 (t, 3H, J=6.7 Hz), 1.04 (t, 3H, J=7.4 Hz), 1.25–1.50 (m, 26H), 1.55–1.80 (m, 2H), 3.04–3.12 (m, 1H), 3.70–3.80 (m, 1H);

$^{13}$C NMR (75 MHz, CD$_3$OD) δ 10.6, 14.5, 21.4, 23.8, 27.1, 30.5, 30.6, 30.7, 30.8, 33.0, 33.1, 59.0, 71.4;

ESMS calcd for C$_{18}$H$_{40}$NO (M−Cl) 286.3, found 286.2.

Example 54

(3S,4R)-3-(N,N-Dibenzylamino)-4-nonadecanol, 56

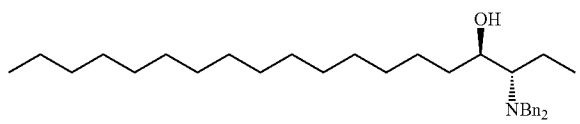

According to the method of Example 26, from aldehyde 6 (1.0 g, 3.7 mmol) and 1-bromopentadecane (6.55 g, 22.5 mmol), alcohol 56 was obtained as a colorless oil (800 mg, 45% yield).

$^1$H NMR (300 MHz, CDCl$_3$) δ 0.88 (t, 3H, J=6.8 Hz), 0.99 (t, 3H, J=7.4 Hz), 1.20–1.35 (m, 26H), 1.40–1.55 (m, 3H), 1.70–1.80 (m, 1H), 2.56–2.62 (m, 1H), 3.60–3.75 (m, 5H), 7.26–7.46 (m, 10H).

Example 55

(3S,4R)-3-Amino-4-nonadecanol, 57

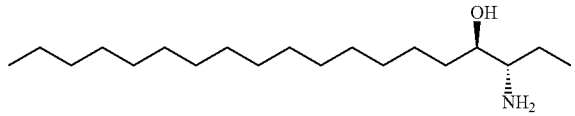

According to the method of Example 27, from N,N-dibenzylamine 56 (400 mg, 0.83 mmol), aminoalcohol 57 was obtained as a white solid (220 mg, 88% yield).

$^1$H NMR (500, MHz, CD$_3$OD) δ 0.80 (t, 3H, J=7.1 Hz), 0.91 (t, 3H, J=7.5 Hz), 1.15–1.25 (m, 26H), 1.30–1.40 (m, 2H), 1.40–1.50 (m, 1H), 1.55–1.65 (m, 1H), 2.70–2.75 (m, 1H), 3.45–3.50 (m, 1H);

$^{13}$C NMR (125 MHz, CD$_3$OD) δ 11.8, 15.4, 24.5, 24.7, 28.1, 31.4, 31.7, 33.9, 34.0, 59.8, 74.3;

ESMS calcd for C$_{19}$H$_{42}$NO (M+H) 300.3, found 300.4.

Example 56

(3S,4R)-3-Amino-4-nonadecanol hydrochloride, 58

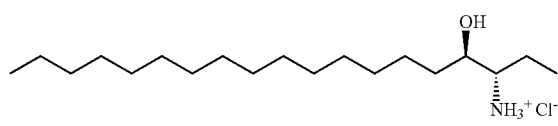

According to the method of Example 32, from aminoalcohol 57 (20 mg, 0.07 mmol), hydrochloride 58 was obtained as a white solid (6 mg, 27% yield).

$^1$H NMR (300 MHz, CD$_3$OD) δ 0.90 (t, 3H, J=6.6 Hz), 1.04 (t, 3H, J=7.6 Hz), 1.25–1.50 (m, 28H), 1.55–1.80 (m, 2H), 3.04–3.12 (m, 1H), 3.70–3.80 (m, 1H);

$^{13}$C NMR (75 MHz, CD$_3$OD) δ 10.6, 14.4, 21.4, 23.8, 27.1, 30.5, 30.6, 30.8, 33.0, 33.1, 59.0, 71.4;

ESMS calcd for C$_{19}$H$_{42}$NO (M−Cl) 300.3, found 300.5.

Example 57

(3S,4R)-3-(N,N-Dibenzylamino)-4-eicosanol, 59

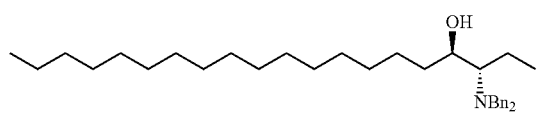

According to the method of Example 26, from aldehyde 6 (600 mg, 2.24 mmol) and 1-bromohexadecane (1.37 mL, 4.49 mmol), alcohol 59 was obtained as a colorless oil (775 mg, 70% yield).

R$_f$ 0.50 (hexane/EtOAc 9:1);

$^1$H NMR (300 MHz, CDCl$_3$) δ 0.87 (t, 3H, J=7.1 Hz), 0.95 (t, 3H, J=7.1 Hz), 1.20–1.40 (m, 28H), 1.45–1.60 (m, 3H), 1.70–1.85 (m, 1H), 2.22 (br s, 1H), 2.62–2.68 (m, 1H), 3.62–3.73 (m, 5H), 7.24–7.34 (m, 10H);

$^{13}$C NMR (75 MHz, CDCl3) δ 12.3, 14.1, 18.1, 22.6, 26.6, 29.3, 29.6, 29.7, 31.9, 34.4, 55.1, 62.7, 70.5, 126.9, 128.2, 128.9, 140.1;

ESMS calcd for C$_{34}$H$_{56}$NO (M+H) 494.4, found 494.5.

Example 58

(3S,4R)-3-Amino-4-eicosanol, 60

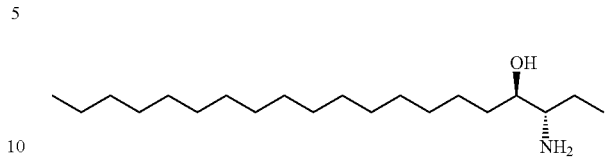

According to the method of Example 27, from N,N-dibenzylamine 59 (200 mg, 0.40 mmol), aminoalcohol 60 was obtained as a white solid (104 mg, 83% yield).

$^1$H NMR (300 MHz, CD$_3$OD) δ 0.87 (t, 3H, J=6.9 Hz), 0.89 (t, 3H, J=6.9 Hz), 1.20–1.40 (m, 30H), 1.45–1.53 (m, 2H), 2.55–3.20 (m, 4H), 3.50–3.61 (m, 1H);

ESMS calcd for C$_{20}$H$_{44}$NO (M+H) 314.3, found 314.4.

Example 59

(3S,4R)-3-Amino-4-eicosanol hydrochloride, 61

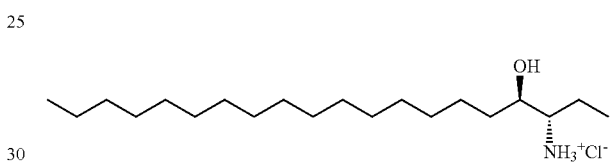

According to the method of Example 32, from aminoalcohol 60 (30.0 mg, 0.17 mmol), hydrochloride 61 was obtained as a white solid (20.4 mg, 61% yield).

$^1$H NMR (300 MHz, CD$_3$OD) δ 0.90 (t, 3H, J=7.4 Hz), 1.04 (t, 3H, J=7.4 Hz), 1.25–1.50 (m, 30H), 1.55–1.80 (m, 2H), 3.04–3.12 (m, 1H), 3.70–3.80 (m, 1H);

$^{13}$C NMR (75 MHz, CDCl$_3$) δ 10.5, 14.4, 21.3, 23.7, 27.1, 30.4, 30.6, 30.7, 30.8, 32.9, 33.0, 59.0, 71.4;

ESMS calcd for C$_{20}$H$_{44}$NO (M−Cl) 314.3, found 314.5.

Example 60

(3S,4R)-3-(N,N-Dibenzylamino)-4-heneicosanol, 62

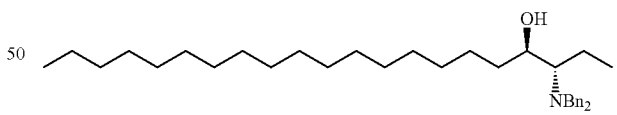

According to the method of Example 26, from aldehyde 6 (610 mg, 2.28 mmol) and 1-bromoheptadecane (1.82 g, 5.70 mmol), alcohol 62 was obtained as a colorless oil (620 mg, 54% yield).

R$_f$ 0.50 hexane/EtOAc 5:1);

$^1$H NMR (300 MHz, CDCl$_3$) δ 0.86 (t, 3H, J=6.9 Hz), 0.94 (t, 3H, J=7.3 Hz), 1.20–1.40 (m, 30H), 1.45–1.55 (m, 3H), 1.70–1.85 (m, 1H), 2.24 (br s, 1H), 2.73 (td, 1H, J=7.0, 4.2 Hz), 3.60–3.75 (m, 5H), 7.22–7.36 (m, 10H);

$^{13}$C NMR (75 MHz, CDCl$_3$) δ 12.3, 14.1, 18.1, 22.7, 26.7, 29.4, 29.6, 29.7, 31.9, 34.4, 55.2, 62.8, 70.6, 126.9, 128.3, 128.9, 140.1;

ESMS calcd for C$_{35}$H$_{58}$NO (M+H) 508.4, found 508.5.

Example 61

(3S,4R)-3-Amino-4-heneicosanol, 63

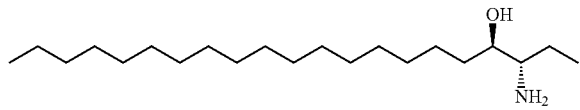

According to the method of Example 27, from N,N-dibenzylamine 62 (295 mg, 0.58 mmol), aminoalcohol 63 was obtained as a white solid (184 mg, 97% yield).

$^1$H NMR (300 MHz, CDCl$_3$) δ 0.87 (t, 3H, J=7.0 Hz), 0.94 (t, 3H, J=7.4 Hz), 1.20–1.40 (m, 32H), 1.45–1.60 (m, 2H), 1.79 (br s, 3H), 2.62–2.70 (m, 1H), 3.42–3.50 (m, 1H);

$^{13}$C NMR (75 MHz, CDCl$_3$) δ 11.0, 14.1, 22.7, 25.0, 26.2, 29.3, 29.7, 29.8, 31.4, 31.9, 57.1, 74.1;

ESMS calcd for C$_{21}$H$_{46}$NO (M+H) 328.3, found 328.4.

Example 62

(3S,4R)-3-Amino-4-heneicosanol hydrochloride, 64

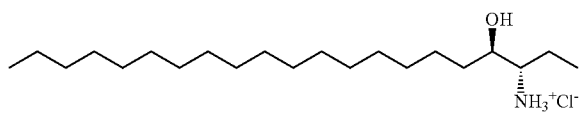

According to the method of Example 32, from aminoalcohol 63 (74 mg, 0.23 mmol), hydrochloride 64 was obtained as a white solid (51 mg, 62% yield).

$^1$H NMR (300 MHz, CD$_3$OD) δ 0.90 (t, 3H, * 6.9 Hz), 1.04 (t, 3H, J=7.4 Hz), 1.25–1.50 (m, 32H), 1.55–1.80 (m, 2H), 3.04–3.12 (m, 1H), 3.70–3.80 (m, 1H);

$^{13}$C NMR (75 MHz, CD$_3$OD) δ 10.6, 14.5, 21.4, 23.7, 27.1, 30.5, 30.6, 30.7, 30.8, 33.0, 33.1, 59.0, 71.4;

ESMS calcd for C$_{21}$H$_{46}$NO (M−Cl) 328.3, found 328.4.

Example 63

(4S,5R)4-(N,N-Dibenzylamino)-5-eicosanol, 65

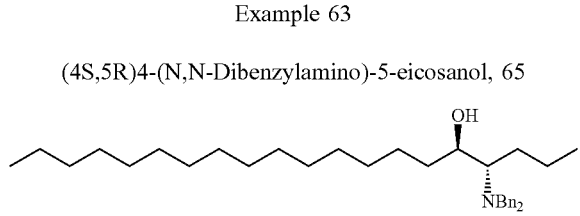

According to the method of Example 26, from aldehyde 11 (123 mg, 0.44 mmol) and 1-bromopentadecane (318 mg, 1.09 mmol), alcohol 65 was obtained as a colorless oil (161 mg, 75% yield).

R$_f$ 0.53 (hexane/EtOAc 5:1);

$^1$H NMR (300 MHz, CDCl$_3$) δ 0.89 (t, 3H, J=6.9 Hz), 0.91 (t, 3H, J=7.0 Hz), 1.20–1.40 (m, 28H), 1.40–1.55 (m, 3H), 1.70–1.80 (m, 1H), 2.22 (br S, 1H), 2.65–2.72 (m, 1H), 3.60–3.75 (m, 5H), 7.21–7.35 (m, 10H);

$^{13}$C NMR (75 MHz, CDCl$_3$) δ 14.1, 14.4, 20.6, 22.7, 26.7, 27.5, 29.4, 29.6, 29.6, 29.7, 31.9, 34.4, 55.2, 60.7, 70.7, 127.0, 128.3, 128.9, 140.1;

ESMS calcd for C$_{34}$H$_{56}$NO (M+H) 494.4, found 494.4.

Example 64

(4S,5R)-4-Amino-5-eicosanol, 66

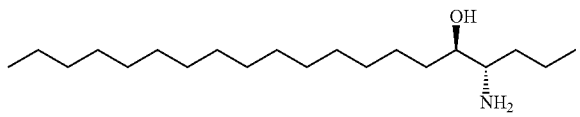

According to the method of Example 27, from N,N-dibenzylamine 65 (37 mg, 0.075 mmol), aminoalcohol 66 was obtained as a white solid (17 mg, 72% yield).

$^1$H NMR (300 MHz, CDCl$_3$) δ 0.87 (t, 3H, J=6.7 Hz), 0.93 (t, 3H, J=6.7 Hz), 1.20–1.40 (m, 30H), 1.45–1.55 (m, 2H), 2.75–2.80 (m. 1H), 3.40–3.45 (m, 1H);

$^{13}$C NMR (75 MHz, CDCl$_3$) δ 14.1, 19.7, 22.7, 26.2, 29.4, 29.7, 31.4, 31.9, 34.4, 55.0, 74.4;

ESMS calcd for C$_{20}$H$_{44}$NO (M+H) 314.3, found 314.3.

Example 65

(4S,5R)-4-Amino-5-eicosanol hydrochloride, 67

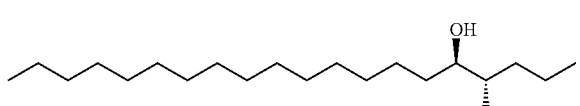

According to the method of Example 32, from aminoalcohol 66 (9 mg, 0.03 mmol), hydrochloride 67 was obtained as a white solid (3 mg, 30% yield).

$^1$H NMR (300 MHz, CD$_3$OD) δ 0.90 (t, 3H, J=6.9 Hz), 0.99 (t, 3H, J=7.0 Hz), 1.20–1.40 (m, 28H), 1.40–1.65 (m, 4H), 3.08–3.18 (m, 1H), 3.65–3.75 (m, 1H);

ESMS calcd for C$_{20}$H$_{44}$NO (M−Cl) 314.3, found 314.5.

Example 66

(3S,4R)-3-(N,N-Dibenzylamino)-2-methyl-4-nonadecanol, 68

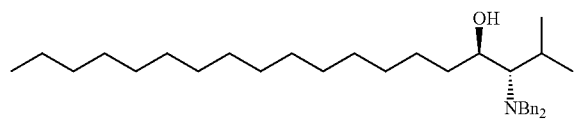

According to the method of Example 26, from aldehyde 14 (447 mg, 1.59 mmol) and 1-bromopentadecane (1.16 g, 4.0 mmol), alcohol 68 was obtained as a colorless oil (340 mg, 43% yield).

R$_f$ 0.50 (hexane/EtOAc 5:1);

$^1$H NMR (300 MHz, CDCl$_3$) δ 0.93 (t, 3H, J=7.0 Hz), 0.96 (d, 3H, J=6.5 Hz), 1.25–1.40 (m, 29H), 1.55–1.70 (m, 2H), 2.19–2.27 (m, 1H), 2.56 (dd, 1H, J=9.7, 4.7 Hz), 2.84 (br d, 1H,. J=7.9 Hz), 3.55–3.65 (m, 1H), 3.79 (d, 2H, J=13.4 Hz), 3.9.0 (d, 2H, J=13.4 Hz), 7.25–7.38 (m, 10H);

$^{13}$C NMR (75 MHz, CDCl$_3$) δ 14.1, 20.8, 22.7, 23.2, 27.1, 28.2, 29.3, 29.6, 29.6, 31.9, 33.2, 56.3, 67.2, 70.3, 127.2, 128.4, 129.1, 139.9;

ESMS calcd for C$_{34}$H$_{56}$NO (M+H) 494.4, found 494.4.

Example 67

(3S,4R)-3-Amino-2-methyl-4-nonadecanol, 69

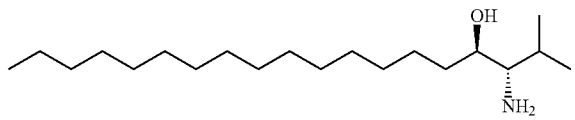

According to the method of Example 27, from N,N-dibenzylamine 68 (171 mg, 0.35 mmol), aminoalcohol 69 was obtained as a white solid (90 mg, 83% yield).

$^1$H NMR (300 MHz, CDCl$_3$) δ 0.85 (t, 3H, J=7.0 Hz), 0.88 (d, 3H, J=6.7 Hz), 0.95 (d, 3H, J=6.7 Hz), 1.20–1.40 (m, 26H), 1.50–1.65 (m, 3H), 2.02 (br s, 3H), 2.41 (dd, 1H, J=7.9, 4.7 Hz), 3.54–3.62 (m, 1H);

$^{13}$C NMR-(75 MHz, CDCl$_3$) δ 14.1, 19.2, 19.8, 22.6, 26.1, 29.3, 29.6, 29.7, 29.7, 30.4, 30.8, 31.9, 61.7, 71.5;

ESMS calcd for C$_{20}$H$_{44}$NO (M+H) 314.3, found 314.3.

Example 68

(3S,4R)-3-Amino-2-methyl-4-nonadecanol hydrocloride, 70

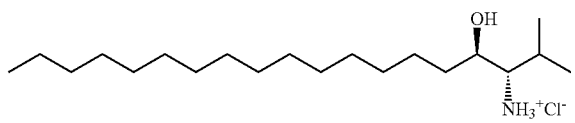

According to the method of Example 32, from aminoalcohol 69 (68.5 mg, 0.22 mmol), hydrochloride 70 was obtained as a white solid (55.5 mg, 73% yield).

$^1$H NMR (300 MHz, CD$_3$OD) δ 0.90 (t, 3H, J=6.7 Hz), 1.01 (d, 3H, J=6.7 Hz), 1.05 (d, 3H, J=6.7 Hz), 1.25–1.40 (m, 26H), 1.55–1.70 (m, 2H), 1.88–1.96 (m, 1H), 2.84 (dd, 1H, J=8.6, 4.1 Hz), 3.80–3.85 (m, 1H);

$^{13}$C NMR (75 MHz, CDOD$_3$) δ 14.5, 19.5, 19.9, 23.7, 27.0, 28.7, 30.5, 30.6, 30.7, 30.8, 31.1, 33.1, 63.8, 69.5;

ESMS calcd for C$_{20}$H$_{44}$NO (M−Cl) 314.3, found 314.4.

Example 69

(3S,4S,5R)-4-(N,N-Dibenzylamino)-3-methyl-5-eicosanol, 71

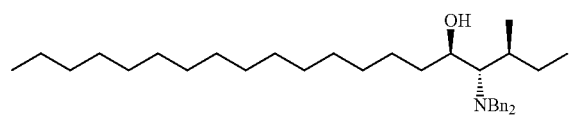

According to the method of Example 26, from aldehyde 17 (470 mg, 1.59 mmol) and 1-bromopentadecane (0.63 mL, 3.18 mmol), alcohol 71 was obtained as a colorless oil (499 mg, 60% yield).

R$_f$ 0.60 (hexane/EtOAc 9:1);

$^1$H NMR (300 MHz, CDCl$_3$) δ 0.85–0.90 (m, 6H), 0.98 (d, 3H, J=7.4 Hz), 1.25–1.40 (m, 27H), 1.55–1.60 (m, 2H), 1.86–1.97 (mi, 2H), 2.54–2.60 (m,2H), 3.58–3.68 (m, 1H), 3.70 (d, 2H, J=13.7 Hz), 3.85 (d, 2H, J=13.7 Hz), 7.25–7.38 (m, 10H);

$^{13}$C NMR (75 MHz, CDCl$_3$) δ 11.3, 14.1, 16.1, 22.6, 26.8, 28.1, 29.3, 29.5, 29.6, 31.8, 33.4, 34.2, 56.1, 65.5, 70.3, 127.1, 128.3, 129.1, 138.9;

ESMS calcd for C$_{35}$H$_{58}$NO (M+H) 508.4, found 508.8.

Example 70

(3S,4S,5R)-4-Amino-3-methyl-5-eicosanol, 72

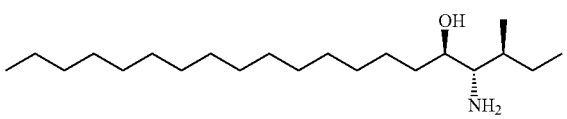

According to the method of Example 27, from N,N-dibenzylamine 71 (70 mg, 0.13 mmol), aminoalcohol 72 was obtained as a white solid (40 mg, 89% yield).

$^1$H NMR (300 MHz, CDCl$_3$) δ 0.91–1.10 (m, 6H), 1.15–1.46 (m, 31H), 2.45–2.51 (m, 2H), 1.65–1.69 (m, 1H), 2.68–2.72 (m, 1H), 3.62–3.69 (m, 1H), 4.25–4.60 (m, 2H);

ESMS calcd for C$_{21}$H$_{46}$NO (M+H) 328.3, found 328.4.

Example 71

(3S,4S,5R)-4-Amino-3-methyl-5-eicosanol hydrochloride, 73

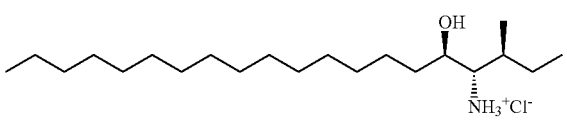

According to the method of Example 32, from aminoalcohol 72 (40 mg, 0.11 mmol), hydrochloride 73 was obtained as a white solid (32 mg, 78% yield).

$^1$H NMR (300 MHz, CDCl$_3$) δ 0.87 (t, 3H, J=6.9 Hz), 0.95 (t, 3H, J=6.9 Hz), 1.20–1.40 (m, 31H), 1.45–1.60 (m, 2H), 1.75–1.85 (m, 1H), 3.18–3.23 (m, 1H), 3.90–3.95 (m, 1H), 7.90–8.05 (br s, 3H);

$^{13}$C NMR (75 MHz, CDCl$_3$) δ 10.5, 14.1, 15.6, 22.6, 25.3, 26.1, 29.3, 29.6, 29.7, 31.9, 33.7, 61.6, 70.1;

ESMS calcd for C$_{21}$H$_{46}$NO (M−Cl) 328.3, found 328.4.

Example 72

(2S,3R)-1-(4'-Benzyloxyphenyl)-2-(N,N-dibenzylamino)-3-octadecanol, 74

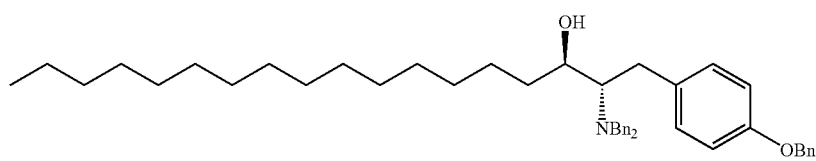

According to the method of Example 26, from aldehyde 20 (597 mg, 1.37 mmol) and 1-bromopentadecane (999 mg, 3.43 mmol), alcohol 74 was obtained as a colorless oil (496 mg, 56% yield).

$R_f$ 0.50 (hexane/EtOAc 10:1);

$^1$H NMR (300 MHz, CDCl$_3$) δ 0.90 (t, 3H, J=6.7 Hz), 1.25–1.40 (m, 26H), 1.55–1.70 (m, 2H), 1.96 (br s, 1H), 2.43 (dd, 1H, J=12.4, 5.2 Hz), 2.95–3.07 (m, 2H), 3.65 (d, 2H, J=13.8 Hz), 3.65–3.75 (m, 1H), 3.78 (d, 2H, J=13.8 Hz), 5.09 (s, 2H), 6.92 (d, 2H, J=8.6 Hz), 7.07 (d, 2H, J=8.6 Hz), 7.20–7.49 (m, 15H);

$^{13}$C NMR (75 MHz, CDCl$_3$) δ 14.1, 22.7, 26.4, 29.4, 29.5, 29.6, 29.7, 31.0, 31.9, 34.6, 55.1, 63.2, 70.1, 71.6, 114.8, 126.9, 127.4, 127.9, 128.2, 128.6, 128.8, 130.2, 132.8, 137.2, 139.8, 157.1;

ESMS calcd for C$_{45}$H$_{62}$NO$_2$ (M+H) 648.5, found 648.5.

Example 73

(2S,3R)-2-Amino-1-(4'-hydroxyphenyl)-3-octadecanol, 75

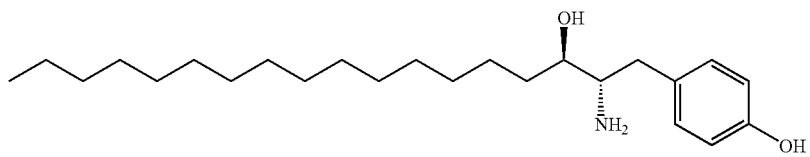

According to the method of Example 27, from N,N-dibenzylamine 74 (140 mg, 0.22 mmol), aminoalcohol 75 was obtained as a white solid (80 mg, 98% yield).

$^1$H NMR (300 MHz, CD$_3$OD) δ 0.89 (d, 3H, J=6.6 Hz), 1.25–1.40 (m, 26H), 1.50–1.65 (m, 21), 2.35–2.44 (m, 1H), 2.81–2.92 (m, 2H), 3.45–3.50 (m, 1H), 6.73 (d, 2H, J=8.2 Hz), 7.03 (d, 2H, J=8.2 Hz);

$^{13}$C NMR (75 MHz, CD$_3$OD) δ 14.5, 23.7, 27.2, 30.5, 30.8, 30.8, 33.1, 33.4, 38.3, 58.7, 74.8, 116.4, 130.9, 131.2, 157.1;

ESMS calcd for C$_{24}$H$_{44}$NO$_2$ (M+H) 378.3, found 378.3.

Example 74

(2S,3R)-2-Amino-1-(4'-hydroxyphenyl)-3-octadecanol hydrochloride, 76

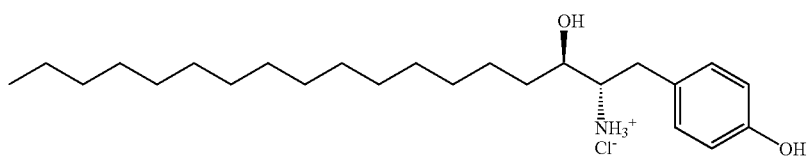

According to the method of Example 32, from aminoalcohol 75 (43 mg, 0.11 mmol), hydrochloride 76 was obtained as a white solid (10 mg, 21% yield).

$^1$H NMR (300 MHz, CD$_3$OD) δ 0.90 (d, 3H, J=6.7 Hz), 1.20–1.40 (m, 26H), 1.45–1.60 (m, 2H), 2.72 (dd, 1H, J=14.3, 9.3 Hz), 2.92 (dd, 1H, J=14.3, 5.4 Hz), 3.39 (ddd, 1H, J=9.1, 5.5, 3.2 Hz), 3.66–3.75 (m, 1H), 6.78 (d, 2H, J=8.6 Hz), 7.10 (d, 2H, J=8.6 Hz);

$^{13}$C NMR (75 MHz, CD$_3$OD) δ 14.5, 23.8, 27.1, 30.5, 30.6, 30.7, 30.8, 33.1, 33.6, 59.0, 71.3, 116.8, 127.9, 131.3, 157.9;

ESMS calcd for C$_{24}$H$_{44}$NO$_2$ (M−Cl) 378.3, found 378.3.

Example 75

(4S,5R)-1,4-Bis-(N,N-dibenzylamino)-5-eicosanol, 77

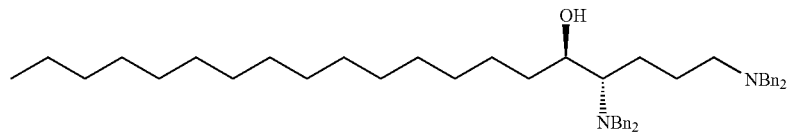

According to the method of Example 26, from aldehyde 23 (503 mg, 1.05 mmol) and 1-bromopentadecane (768; mg, 2.64 mmol), alcohol 77 was obtained as a colorless oil (350 mg, 48% yield).

$R_f$ 0.50 (hexane/EtOAc 5:1);

$^1$H NMR (300 MHz, CDCl$_3$) δ 0.90 (t, 3H, J=6.7 Hz), 1.25–1.40 (m, 28H), 1.40–1.60 (m, 2H), 1.60–1.75 (m, 2H), 1.97 (br s, 1H), 2.43 (t, 2H, J=6.7 Hz), 2.56–2.62 (m, 1H), 3.57 (s, 4H), 3.61 (d, 2H, J=13.8 Hz), 3.65–3.75 (m, 1H), 3.67 (d, 2H, J=13.8 Hz), 7.20–7.40 (m, 20H);

$^{13}$C NMR (75 MHz, CDCl$_3$) δ 14.1, 22.7, 23.1, 25.1, 26.6, 29.4, 29.6, 29.7, 31.9, 34.6, 53.9, 55.1, 58.4, 61.2, 70.9, 126.8, 127.0, 128.1, 128.3, 128.8, 128.9, 139.8, 140.1;

ESMS calcd for C$_{48}$H$_{69}$N$_2$O (M+H) 689.5, found 689.5.

Example 76

(4S,5R)-1,4-Diamino-5-eicosanol, 78

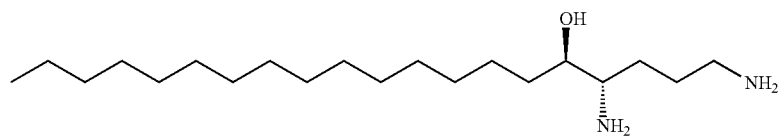

According to the method of Example 27, from bis-(N,N-dibenzylamine) 77 (105 mg, 0.15 mmol), diaminoalcohol 78 was obtained as a white solid (45 mg, 91% yield).

$^1$H NMR (300 MHz, CD$_3$OD) δ 0.88 (d, 3H, J=6.7 Hz), 1.25–1.45 (m, 28H), 1.60–1.75 (m, 4H), 2.65–2.85 (m, 3H), 3.42–3.52 (m, 1H);

$^{13}$C NMR (75 MHz, CD$_3$OD) δ 14.4, 23.7, 26.9, 27.2, 28.8, 30.5, 30.8, 33.1, 33.4, 41.1, 56.9, 74.6;

ESMS calcd for C$_{20}$H$_{45}$N$_2$O (M+H) 329.3, found 329.3.

Example 77

(4S,5R)-1,4-Diamino-5-eicosanol dihydrochloride, 79

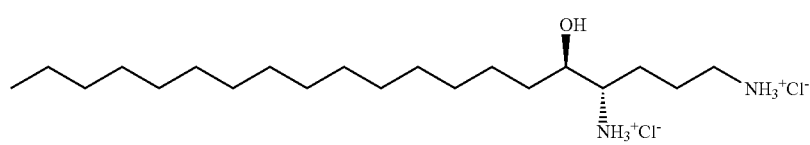

According to the method of Example 32, from diaminoalcohol 78 (40 mg, 0.12 mmol) dihydrochloride 79 was obtained as a white solid (30 mg, 61% yield).

$^1$H NMR (300 MHz, CD$_3$OD) δ 0.89 (d, 3H, J=6.5 Hz), 1.25–1.40 (m, 26H), 1.45–1.60 (m, 3H), 1.70–1.95 (m, 3H), 2.98 (t, 2H, J=7.0 Hz), 3.20–3.25 (m, 1H), 3.72–3.80 (m, 1H);

$^{13}$C NMR (75 MHz, CD$_3$OD) δ 14.5, 23.7, 25.1, 25.5, 27.1, 30.5, 30.7, 30.8, 30.8, 33.1, 33.3, 40.4, 56.9, 71.5;

ESMS calcd for C$_{20}$H$_{45}$N$_2$O (M−HCl$_2$) 329.3, found 329.4.

Example 78

(2R,3S)-2-(N,N-Dibenzylamino)-3-octadecanol, 80

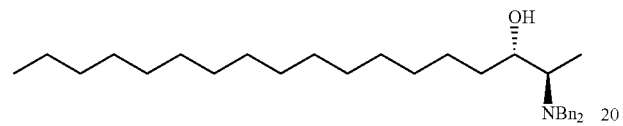

According to the method of Example 26, from aldehyde 26 (445 mg, 1.76 mmol) and 1-bromopentadecane (1.28 g, 4.39 mmol), alcohol 80 was obtained as a colorless oil (422 mg, 52% yield).

R$_f$ 0.50 (hexane/EtOAc 5:1);

$^1$H NMR (300 MHz, CDCl$_3$) δ 0.91 (t, 3H, J=6.9 Hz), 1.12 (d, 3H, J=6.7 Hz), 1.20–1.40 (m, 26H), 1.65–1.75 (m, 2H), 1.85 (br s, 1H), 2.73 (quint, 1H, J=6.4 Hz), 3.49 (d, 2H, J=13.9 Hz), 3.57–3.65 (m, 1H), 3.78 (d, 2H, J=13.8 Hz), 7.21–7.38 (m, 10H);

$^{13}$C NMR (75 MHz, CDCl$_3$) δ 8.6, 14.1, 22.7, 25.9, 29.3, 29.6, 29.7, 31.9, 34.4, 54.8, 57.3, 73.6, 126.9, 128.2, 128.8, 140.2;

ESMS calcd for C$_{32}$H$_{52}$NO (M+H) 466.4, found 466.4.

Example 79

(2R,3S)-2-Amino-3-octadecanol, 81

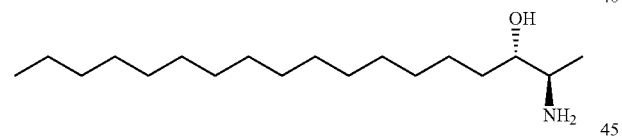

According to the method of Example 27, from N,N-dibenzylamine 80 (256 mg, 0.55 mmol), aminoalcohol 81was obtained as a white solid (175 mg, 92% yield).

$^1$H NMR (300 MHz, CDCl$_3$) δ 0.88 (t, 3H, J=7.0 Hz), 1.02 (d, 3H, J=6.5 Hz), 1.20–1.40 (m, 26H), 1.45–1.55 (m, 2H), 1.85 (br s, 3H), 2.94–3.04 (m, 1H), 3.42–3.52 (m, 1H);

$^{13}$C NMR (75 MHz, CDCl$_3$) δ 14.1, 16.3, 22.7, 26.2, 29.3, 29.7, 31.9, 32.5, 50.4, 74.2;

ESMS calcd for C18H$_{40}$NO (M+H) 286.3, found 286.2.

Example 80

(2S,3R)-O-Acetyl-2-(N,N-dibenzylamino)-3-octadecanol, 82

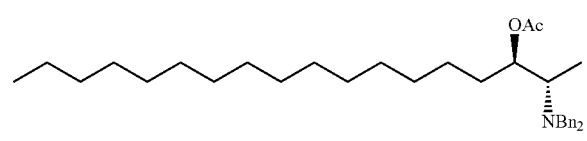

To a solution of alcohol 39 (48.5 mg. 0.104 mmol) in CH$_2$Cl$_2$ (1.0 mL) at room temperature, pyridine (25 μL, 0.313 mmol), Ac$_2$O (29 μL, 0.313 mmol) and DMAP (ca. 5 mg, cat.) were added. The reaction was stirred for 4 h, and then the solvents were evaporated in vacuo. The crude was purified by column chromatography on silica (hexane/EtOAc 10: 1) to obtain acetate 82 as a colorless oil (46 mg, 87% yield).

R$_f$ 0.62 (hexane/EtOAc 5:1);

$^1$H NMR (300 MHz, CDCl$_3$) δ 0.91 (t, 3H, J=6.8 Hz), 1.07 (d, 3H, J=6.6 Hz), 1.20–1.35 (m, 26H), 1.40–1.50 (m, 1H), 1.75–1.85 (m, 1H), 2.02 (s, 3H), 2.81 (quint, 1H, J=7.1 Hz), 3.46 (d, 2H, J=13.9 Hz), 3.76 (d, 2H, J=13.9 Hz), 5.11 (dt, 1H, J=7.5, 4.2 Hz), 7.22–7.39 (m, 10H);

$^{13}$C NMR (75 MHz, CDCl$_3$) δ 8.7, 14.1, 21.2, 22.7, 24.8, 29.3, 29.5, 29.6, 29.7, 31.9, 32.0, 54.2, 54.7, 75.2, 126.8, 128.1, 12.8, 140.0, 170.8;

ESMS calcd for C$_{34}$H$_{54}$NO$_2$ (M+H) 508.4, found 508.5.

Example 81

(2S,3R)-2-(N-Acetylamino)-3-octadecanol, 83

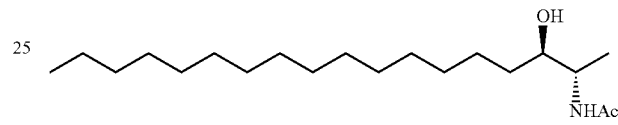

According to the method of Example 27, from N,N-dibenzylamine 82 (41 mg, 0.081 mmol), acetamide 83 was obtained as a white solid (13 mg, 49% yield).

$^1$H NMR (300 MHz, CDCl$_3$) δ 0.89 (t, 3H, J=7.1 Hz), 1.09 (d, 3H, J=6.8 Hz), 1.20–1.35 (m, 26H), 1.45–1.55 (m, 2H), 1.99 (s, 3H), 2.15 (br s, 1H), 3.60–3.65 (m, 1H), 4.00 (dquint, 1H, J=7.4, 2.4 Hz), 5.84 (br d, 1H, J=7.1 Hz);

$^{13}$C NMR (75 MHz, CDCl$_3$) δ 13.9, 14.1, 22.7, 23.5, 26.0, 29.4, 29.6, 29.7, 31.9, 33.6, 49.5, 74.2, 82.4, 170.0;

ESMS calcd for C$_{20}$H$_{41}$NO$_2$Na (M+Na) 350.3, found 350.3.

Example 82

(2S,3R)-2-(N,N-Dibenzylamino)-3-(methoxy)-octadecane, 84

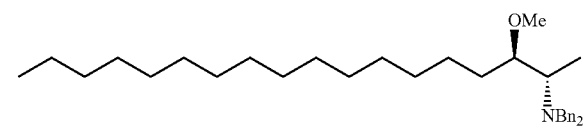

To a solution of alcohol 39 (322 mg, 0.69 mmol) in DMF (3.5 mL) at room temperature, NaH (60% mineral dispersion, 69 mg, 1.73 mmol) and MeI (0.22 mL, 3.46 mmol) were added. After stirring for 16 h, the mixture was quenched with H$_2$O (15 mL), extracted with Et$_2$O (3×15 mL), dried over Na$_2$SO$_4$ and concentrated in vacuo. The crude was purified by column chromatography on silica (hexane/EtOAc 15:1) to obtain 84 as a colorless oil (110 mg, 33% yield).

R$_f$ 0.56 (hexane/EtOAc 10:1);

$^1$H NMR (300 MHz, CDCl$_3$) δ 0.94 (t, 3H, J=6.7 Hz), 1.08 (d, 3H, J=6.7 Hz), 1.20–1.40 (m, 26H), 1.55–1.70 (m, 2H), 2.74 (quint, 1H, J=6.7 Hz), 3.27 (q, 1H, J=6.4 Hz), 3.36 (s, 3H), 3.50 (d, 2H, J=13.8 Hz), 3.77 (d, 2H, J=13.8 Hz), 7.23–7.42 (m, 10H);

$^{13}$C NMR (75 MHz, CDCl$_3$) δ 8.2, 14.1, 22.7, 24.4, 29.4, 29.7, 29.7, 29.7, 30.0, 30.6, 31.9, 54.3, 54.7, 57.4, 83.7, 126.7, 128.1, 128.8, 140.4;

ESMS calcd for C$_{33}$H$_{54}$NO (M+H) 480.4, found 480.7.

Example 83

(2S,3R)-2-Amino-3-(methoxy)-octadecane, 85

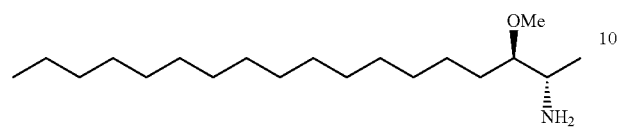

According to the method of Example 27, from N,N-dibenzylamine 84 (54 mg, 0.11 mmol), amine 85 was obtained as a white solid (14 mg, 42% yield).

R$_f$ 0.10 (hexane/EtOAc 1:1);
$^1$H NMR (300 MHz, CDCl$_3$) δ 0.87 (t, 3H, J=6.6 Hz), 1.03 (d, 3H, J=6.7 Hz), 1.20–1.35 (m, 26H), 1.40–1.55 (m, 2H); 1.96 (br s, 2H), 2.94–3.00 (m, 1H), 3.03–3.10 (m, 1H), 3.38 (s, 3H);
$^{13}$C NMR (75 MHz, CDCl$_3$) δ 14.1, 18.3, 22.7, 26.0, 29.1, 29.3, 29.6, 29.6, 29.7, 29.9, 31.9, 47.9, 57.9, 75.0, 85.7;
ESMS calcd for C$_{19}$H$_{42}$NO (M+H) 300.3, found 300.5.

Example 84

(2S,3S)-2-(N,N-Dibenzylamino)-3-chloro-octadecane, 86

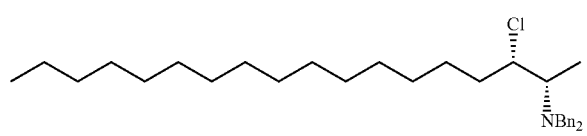

To a cold (0° C.) solution of alcohol 39 (24 mg, 0.051 mmol) in 1 mL of pyridine, POCl$_3$ (0.019 mL, 0.206 mmol) was added dropwise. After stirring at room temperature for 3 h, 0.2 mL of H$_2$O were added and the solvent was evaporated in vacuo. The crude was purified by column chromatography on silica (hexane/EtOAc 10:1) to give chloride 86 as a colorless oil (14 mg, 56% yield).

R$_f$ 0.56 (hexane/EtOAc 10:1);
$^1$H NMR (300 MHz, CDCl$_3$) δ 0.89 (t, 3H, J=6.6 Hz), 1.20–1.55 (m, 30H), 2.00–2.10 (m, 1H), 2.87 (quint, 1H, J=7.0 Hz), 3.47 (d, 2H, J=13.8 Hz), 3.75 (d, 2H, J=13.6 Hz), 3.98 (td, 1H, J=8.1, 3.5 Hz), 7.21–7.36 (m, 10H);
$^{13}$C NMR (75 MHz, CDCl$_3$) δ 10.2, 14.1, 22.7, 26.0, 29.2, 29.4, 29.5, 29.6, 29.7, 31.9, 35.6, 54.3, 57.3, 66.9, 126.9, 128.2, 128.8, 139.8;
ESMS calcd for C$_{32}$H$_{51}$ClN (M+H) 484.4, found 484.3.

Example 85

(2S,3S)-2-Amino-3-chloro-octadecane, 87

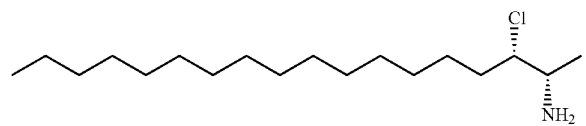

According to the method of Example 27, from N,N-dibenzylamine 86 (13 mg, 0.027 mmol), amine 87 was obtained as a white sohd (3 mg, 37% yield).

R$_f$ 0.10 (EtOAc); $^1$H NMR (300 MHz, CDCl$_3$) δ 0.88 (t, 3H, J=6.6 Hz), 1.12 (d, 3H, J=6.6 Hz), 1.20–1.70 (m, 30H), 3.09 (qd, 1H, J=6.2, 3.4 Hz), 3.90 (td, 1H, J=6.5, 3.5 Hz);

ESMS calcd for C$_{18}$H$_{38}$N (M−Cl) 268.3, found 268.2.

Example 86

(2S,3R)-2-(N,N-Dibenzylamino)-O-(dimethylphosphate)-3-octadecanol, 88

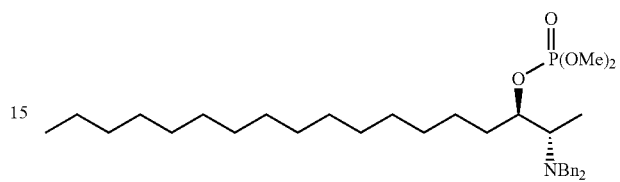

To a solution of alcohol 39 (44 mg, 0.095 mmol) and CBr$_4$ (47 mg, 0.142 mmol) in 0.3 mL of pyridine, (MeO)$_3$P (0.022 mL, 0.189 mmol) was added dropwise. After stirring at room temperature for 24 h, the mixture was diluted with EtOAc (10 mL), washed successively with 5% HCl (10 mL), NaHCO$_3$ (10 mL, sat. aq.) and brine (10 mL), dried over Na$_2$SO$_4$ and concentrated in vacuo. The crude was purified by column chromatography on silica (hexane/EtOAc 10:1 to 2:1) to give dimethyl phosphate 88 as a colorless oil (20 mg, 37% yield) together with unreacted alcohol (25 mg, 57% yield).

R$_f$ 0.31 (hexane/EtOAc 2:1);
$^1$H NMR (300 MHz, CDCl$_3$) δ 0.88 (t, 3H, J=6.5 Hz), 1.16 (d, 3H, J=6.5 Hz), 1.20–1.40 (m, 26H), 1.65–1.80 (m, 2H), 2.84 (quint, 1H, J=6.9 Hz), 3.40 (d, 2H, J=13.8 Hz), 3.69 (dd, 3H, J=2.3, 0.5 Hz), 3.73 (dd, 3H, J=2.3, 0.5 Hz), 3.73 (d, 2H, J=13.6 Hz), 4.47 (ddd, 1H, J=12.8, 7.4, 4.9 Hz), 7.20–7.34 (m, 10H);
$^{13}$C NMR (75 MHz, CDCl$_3$) δ 8.5, 14.1, 22.7, 23.4, 29.3, 29.5, 29.6, 29.6, 29.7, 31.9, 32.6, 54.0 (d), 54.1 (d), 54.2, 81.7 (d), 126.9, 128.2, 128.9, 139.8;
ESMS calcd for C$_{34}$H$_{57}$NO$_4$P (M+H) 574.4, found 574.4.

Example 87

(2S,3R)-2-Amino-O-(dimethylphosphate)-3-octadecanol, 89

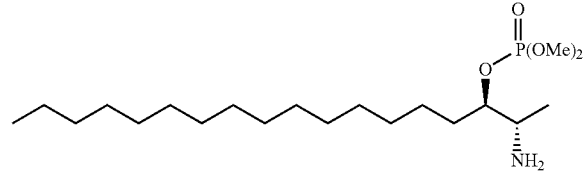

According to the method of Example 27, from N,N-dibenzylamine 88 (16 mg, 0.028 mmol), amine 89 was obtained as a white solid (6 mg, 55% yield).

R$_f$ 0.32 (EtOAc/MeOH 5:1);
$^1$H NMR (300 MHz, CDCl$_3$) δ 0.88 (t, 3H, J=6.6 Hz), 1.08 (d, 3H, J=6.6 Hz), 1.20–1.40 (m, 26H), 1.45–1.55 (m, 1H), 1.60–1.70 (m, 1H), 1.97 (br s, 2H), 3.12–3.20 (m, 1H), 3.76 (s, 3H), 3.80 (s, 3H), 4.24–4.34 (m, 1H);
ESMS calcd for C$_{20}$H$_{45}$NO$_4$P (M+H) 394.3, found 394.3.

Example 88

(2S,3S)-2-(N-Benzyloxycarbonylamino)-3-octadecanol, 90

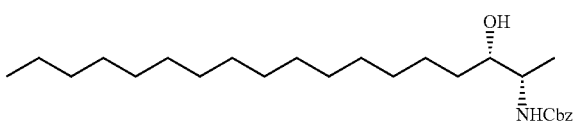

According to the method of Example 26, from aldehyde 28 (640 mg, 3.1 mmol) and 1-bromopentadecane (5.0 g, 17.2 mmol), alcohol 90 was obtained as a colorless oil (690 mg, 53% yield).

$^1$H NMR (500 MHz, CDCl$_3$) δ 0.88 (t, 3H, J=7.1 Hz), 1.20 (d, 3H, J=6.8 Hz), 1.20–1.35 (m, 26H), 1.40–1.50 (m, 2H), 1.74 (br s, 1H), 3.48–3.52 (m, 1H), 3.70–3.75 (m, 1H), 4.90–4.95 (m, 1H), 5.10 (s, 2H), 7.30–7.36 (m, 5H).

Example 89

(2S,3S)-2-Amino-3-octadecanol, 91

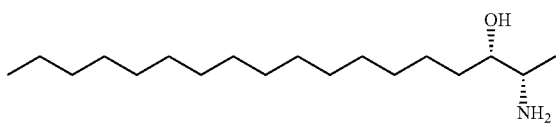

To a solution of N-benzyloxycarbonylamine 90 (330 mg, 0.79 mmol) in MeOH (40 mL) at room temperature, Pd—C (10% wt, 100 mg, 0.09 mmol) was added. The mixture was purged with a stream of dry Ar, and then H$_2$. The reaction was stirred overnight under a H$_2$ atmosphere (1 atm). The catalyst was filtered off through a 0.45 μm teflon filter in polypropylene housing, washing the filter with MeOH (50 mL) and the solvent was evaporated in vacuo. The crude was purified by column chromatography on silica (90:10 CH$_2$Cl$_2$/MeOH to 100% MeOH) to obtain aminoalcohol 91 as a white solid (200 mg, 89% yield).

$^1$H NMR (500 MHz, CD$_3$OD) δ 0.80 (t, 3H, J=7.2 Hz), 0.98 (d, 3H, J=6.5 Hz), 1.15–1.30 (m, 26H); 1.40–1.45 (m, 2H), 2.62–2.65 (m, 1H), 3.10–3.15 (m, 1H);

$^{13}$C NMR (125 MHz, CD$_3$OD) δ 14.8, 19.2, 24.1, 27.2, 20.9, 31.1, 33.5, 35.0, 53.0, 77.1;

ESMS calcd for C$_{18}$H$_{40}$NO (M+H) 286.3, found 286.4.

Example 90

(3S,4S)-3-(N-Benzyloxycarbonylamino)-4-nonadecanol, 92

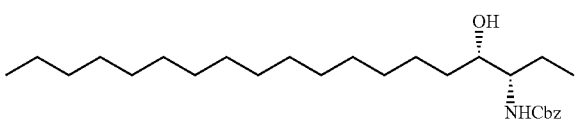

According to the method of Example 26, from aldehyde 8 (680 mg, 3.1 mmol) and 1-bromopentadecane (6.55 g, 22.5 mmol), alcohol 92 was obtained as a colorless oil (800 mg, 60% yield).

$^1$H NMR (500 MHz, CDCl$_3$) δ 0.88 (t, 3H, J=7.1 Hz), 0.96 (t, 3H, J=7.4 Hz), 1.20–1.35 (m, 26H), 1.40–1.45 (m, 2H), 1.55–1.60 (m, 1H), 1.65–1.70 (m, 1H), 3.46–3.52 (m, 1H), 3.60–3.65 (m, 1H), 4.91 (d, 1H, J=9.3 Hz), 5.11 (s, 2H), 7.30–7.36 (m, 5H).

Example 91

(3S,4S)-3-Amino-4-nonadecanol, 93

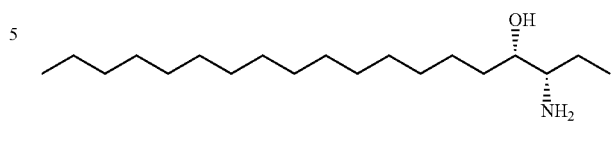

According to the method of Example 89, from N-benzyloxycarbonylamine 92 (230 mg, 0.53 mmol), aminoalcohol 93 was obtained as a white solid (140 mg, 89% yield).

$^1$H NMR (500 MHz, CD$_3$OD) δ 0.80 (t, 3H, J=7.1 Hz), 0.93 (t, 3H, J=7.5 Hz), 1.15–1.25 (m, 26H), 1.30–1.40 (m, 2H), 1.40–1.50 (m, 1H), 1.65–1.75 (m, 1H), 2.80–2.85 (m, 1H), 3.45–3.50 (m, 1H);

$^{13}$C NMR (125 MHz, CD$_3$OD) δ 10.0, 14.4, 23.7, 24.1, 26.6, 30.5, 30.6, 30.8, 33.1, 34.9, 58.8, 70.5;

ESMS calcd for C$_{19}$H$_{42}$NO (M+H) 300.3, found 300.4.

Example 92

(2S,3-S)-2-(N-tert-Butoxycarbonylamino)-3-octadecanol, 94

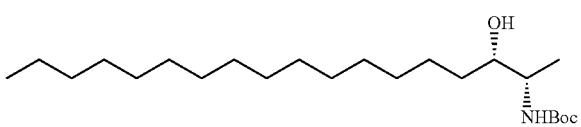

To a solution of aminoalcohol 91 (46 mg, 0.16 mmol) in CH$_2$Cl$_2$ (1.6 mL) at room temperature, Boc$_2$O (42 mg, 0.19 mmol) was added. After stirring for 3.5 h, the solvent was removed in vacuo to obtain 94 as a white solid (62 mg, 100% yield).

R$_f$ 0.35 (hexane/EtOAc 5:1);

$^1$H NMR (300 MHz, CDCl$_3$) δ 0.86 (t, J=6.5 Hz, 3H), 1.15 (d, J=6.8 Hz, 3H), 1.20–1.40 (m, 26H), 1.43 (s, 9H), 1.45–1.60 (m, 2H), 3.40–3.50 (m, 1H), 3.55–3.65 (m, 1H), 4.75 (d, 1H, J=8.8 Hz);

$^{13}$C NMR (75 MHz, CDCl$_3$) δ 14.1, 18.3, 22.7, 25.6, 27.4, 28.4, 29.3, 29.6, 29.6, 29.7, 31.9, 34.2, 50.5, 74.9, 156.2.

Example 93

(2S,3R)-3-Azido-2-(N-tert-butoxycarbonylamino)-octadecane, 95

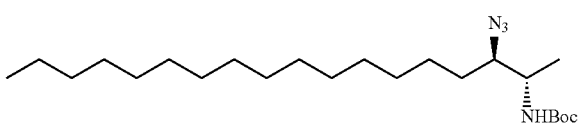

To a cold (0° C.) solution of alcohol 94 (48 mg, 0.12 mmol) in CH$_2$Cl$_2$ (1.25 mL), Et$_3$N (52 μL, 0.37 mmol) and MsCl (24 μL, 0.31 mmol) were added. After stirring for 2 h, the mixture was quenched with H$_2$O (10 mL), extracted with CH$_2$Cl$_2$ (3×10 mL), dried over Na$_2$SO$_4$ and concentrated in vacuo. The crude mesylate was dissolved in DMF (0.65 mL) and NaN$_3$ (40.5 mg, 0.62 mmol) was added. The mixture was stirred at 120 C. for 3 h and then quenched with H$_2$O (10 mL), extracted with Et$_2$O (3×10 mL), dried over Na$_2$SO$_4$ and concentrated in vacuo. The crude was purified by column chromatography on silica (hexane/EtOAc 10:1 to 5:1) to obtain azide 95 as a colorless oil (25 mg, 49% yield).

R$_f$ 0.31 (hexane/EtOAc 10:1);

¹H NMR (300 MHz, CDCl₃) δ 0.87 (t, 3H, J=6.6 Hz), 1.06 (d, 3H, J=6.7 Hz), 1.20–1.40 (m, 26H), 1.44 (s, 9H), 1.45–1.55 (m, 2H), 3.50–3.58 (m, 1H), 3.70–3.80 (m, 1H), 4.68 (br d, 1H, J=7.7 Hz);

¹³C NMR (75 MHz, CDCl₃) δ 14.1, 14.4, 22.7, 26.5,.28.2, 28.4, 29.3, 29.4, 29.4, 29.5, 29.6, 29.6, 29.7, 31.4, 31.9, 49.3, 66.5, 155.0.

Example 94

(2S,3R)-3-Amino-2-(N-tert-butoxycarbonylamino)-octadecane, 96

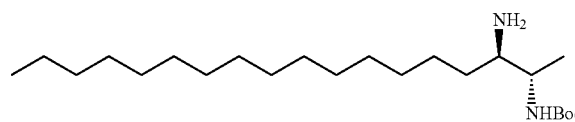

To a solution of azide 95 (25 mg, 0.06 mmol) in MeOH (1.5 mL) at room temperature, Pd—C (10% wt, 16 mg, 0.015 mmol) was added. The mixture was purged with a stream of dry Ar, and then H₂. The reaction was stirred overnight under a H₂ atmosphere (1 atm). The catalyst was filtered off through a 0.45 μm teflon filter in polypropylene housing, washing the filter with MeOH (15 mL) and the solvent was evaporated in vacuo to obtain amine 96 as a white solid (22 mg, 94% yield).

R$_f$ 0.12 (hexane/EtOac 1.10); ¹H NMR (300 MHz, CDCl₃) δ 0.86 (t, 3H, J=6.5 Hz), 1.02 (d, 3H, J=6.7 Hz), 1.20–1.40 (m, 26H), 1.43 (s, 9H), 1.45–1.55 (m, 2H), 2.0.5 (br s, 2H), 2.72–2.82 (m, 1H), 3.60–3.70 (m, 1H), 5.00–5.10 (m, 1H);

¹³C NMR (75 MHz, CDCl₃) δ 14.1, 22.7, 26.5, 28.4, 29.3, 29.7, 31.9, 34.8, 49.7, 54.8, 155.4;

ESMS calcd for C₂₃H₄₉N₂O₂ (M+H) 385.4, found 385.4.

Example 95

(2S,3R)-2,3-Diamino-octadecane dihydrochloride, 97

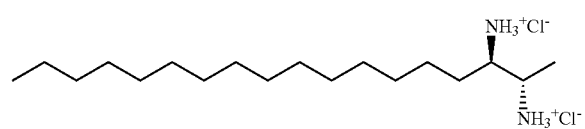

To a solution of N-Boc derivative 96 (22 mg, 0.057 mmol) in dioxane (0.4 mL), anhydrous HCl solution in dioxane (5.3M, 0.43 mL, 2.29 mmol) was added. After stirring at room temperature for 5 h, the solvent was removed in vacuo. The resulting solid was washed with dioxane to obtain dihydrochloride 97 as a white solid (11.5 mg, 56% yield).

¹H NMR (300 MHz, CD₃OD) δ 0.89 (t, 3H, J=6.4 Hz), 1.20–1.45 (m, 26H), 1.42 (d, 3H, J=7.0 Hz), 1.65–1.80 (m, 2H), 3.42–3.48 (m, 1H), 3.58–3.66 (m, 1H);

¹³C NMR (75 MHz, CD₃OD) δ 14.3, 14.4, 23.7, 26.3, 30.4, 30.5, 30.7, 30.7, 30.8, 33.1, 55.1;

ESMS calcd for C₁₈H₄₁N₂ (M–HCl₂) 285.3, found 285.3.

Example 96

(2S,3R)-2-(N-tert-Butoxycarbonylamino)-3-octadecanol, 98

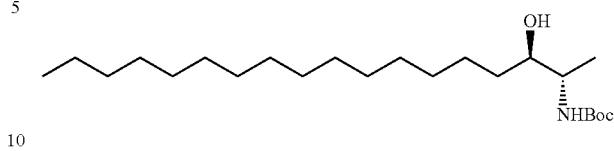

According of the method of Example 92, from aminoalcohol 1 (82.5 mg, 0.30 mmol) N-Boc derivative 98 was obtained as a white solid (110 mg, 95% yield).

R$_f$ 0.35 (hexane/EtOAc 5:1);

¹H NMR (300 MHz, CD₃OD) δ 0.89 (t, 3H, J=6.9 Hz), 1.09 (d, 3H, J=6.9 Hz), 1.20–1.40 (m, 26H), 1.45 (s, 9H), 1.49–1.60 (m, 2H), 2.01–2.09 (m, 1H), 3.55–3.69 (m, 3H), 4.61–4.72 (m, 1H);

¹³C NMR (75 MHz, CDCl₃) δ 14.1, 14.2, 22.6, 26.0, .28.3, 29.3, 29.6, 31.9, 33.4, 50.5, 74.4, 172.1;

ESMS calcd for C₂₃H₄₇NO₃Na (M+Na) 408.4, found 408.3.

Example 97

(2S,3R)-2-(N-tert-Butoxycarbonylamino)-O(2,2,2-trifluoroacetyl)-3-octadecanol, 99

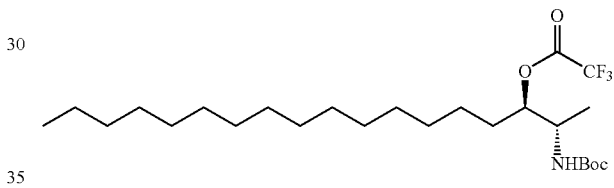

To a solution of alcohol 98 (54 mg, 0.14 mmol) in CH₂Cl₂ (6.0 mL) at room temperature, trifluoroacetic anhydride (28 μL, 0.14 mmol), pyridine (22 μL) 0.42 mmol) and DMAP (1.7 mg, 0.01 mmol) were added. After stirring for 1 h, the reaction was quenched with H₂O (10 mL), extracted with CH₂Cl₂ (3×10 mL), dried over Na₂SO₄ and concentrated in vacuo. The crude was purified by column chromatography on silica (hexane/AcOEt 9:1) to obtain trifluoroacetate 99 as a white solid (17 mg, 25% yield).

R$_f$ 0.24 (hexane/AcOEt 9:1);

¹H NMR (300 MHz, CD₃OD) δ 0.80 (t, 3H, J=6.5 Hz), 1.08 (d, 3H, J=6.5 Hz) 1.18–1.36 (m, 26H), 1.41 (s, 9Hi), 1.52–1.61 (m, 2H), 3.87–3.92 (m, 1H), 4.39–4.44 (m, 1H), 4.98–5.21 (m, 1H);

ESMS calcd for C₂₅H₄₆F₃NO₄Na (M+Na) 504.3, found 504.4.

Example 98

(2S,3R)-2-Ammonium-O-(2,2,2-trifluoroacetyl)-3-octadecanol trifluoroacetate, 100

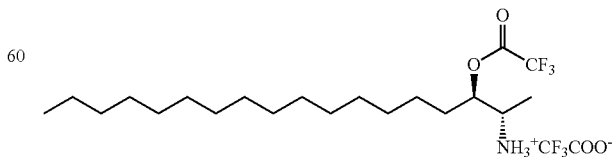

To a solution of N-Boc derivative 99 (17 mg, 0.03 mmol) in CH₂Cl₂ (4 mL) at room temperature, trifluoroacetic acid (1.0 mL) was added. After stirring for 1 h, the solvents were removed in vacuo to obtain 100 as a white solid (16 mg, 94% yield).

$R_f$ 0.24 (hexane/AcOEt 9:1);

$^1$H NMR (300 MHz, CD$_3$OD) δ 0.80 (t, 3H, J=6.1 Hz), 1.18–1.25 (m, 26H), 1.28 (d, 3H, J=6.5Hz), 1.49–1.56 (m, 1H), 1.64–1.69 (m, 1H), 3.51 (m, 1H), 5.27 (m, 1H), 7.94 (m, 1H);

$^{13}$C NMR (75 MHz, CDCl$_3$) δ 12.1, 21.4, 22.7, 25.9, 26.2, 26.3, 26.4, 26.6, 27.4, 28.9, 49.7, 79.0, 101.3, 111.4 161.1;

ESMS calcd for C$_{18}$H$_{39}$NO (M–C$_4$F$_6$O$_3$) 286.5, found 286.2.

Example 99

(2S,3R)-O-Acetyl 2-(N-tert-butoxycarbonylamino)-3-octadecanol, 101

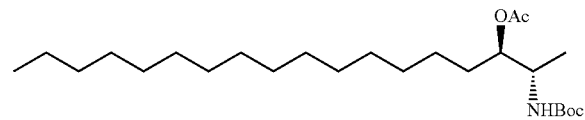

According of the method of Example 80, from alcohol 98 (20 mg, 0.052 mmol), acetate 101 was obtained as a white solid (18.5 mg, 83% yield).

$R_f$ 0.47 (hexane/EtOAc 5:1);

$^1$H NMR (300 MHz, CDCl$_3$) δ 0.87 (t, 3H, J=6.9 Hz), 1.08 (d, 3H, J=6.9 Hz), 1.20–1.35 (m, 26H), 1.43 (s, 9H), 1.45–1.55 (m, 2H), 2.06 (s, 3H), 3.79–3.89 (m, 1H), 4.60 (br d, 1H, J=7.7 Hz), 4.85 (dt, 1H, J=7.2, 4.9 Hz);

$^{13}$C NMR (75 MHz, CDCl$_3$) δ 14.1, 15.3, 21.1, 22.7, 25.5, 28.4, 29.3, 29.4, 29.5, 29.6, 29.6, 29.7, 30.7, 31.9, 48.3, 79.3, 155.1, 171.0;

ESMS calcd for C$_{25}$H$_{49}$NO$_4$Na (M+Na) 450.4, found 450.4.

Example 100

(2S,3R)-O-Acetyl-2-amino-3-octadecanol hydrochloride, 102

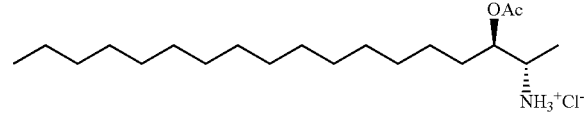

According to the method of Example 95, from N-Boc derivative 101 (13.7 mg, 0.032 mmol) hydrochloride 102 was obtained as a white solid (9 mg, 77% yield).

$^1$H NMR (300 MHz, CD$_3$OD) δ 0.89 (t, 3H, J=6.6 Hz), 1.20–1.40 (m, 29H), 1.55–1.65 (m, 2H), 2.12 (s, 3H), 3.49 (qd, 1H, J=6.7, 2.4 Hz), 5.07 (ddd, 1H, J: 8.7, 5.0, 2.6 Hz);

$^{13}$C NMR (75 MHz, CD$_3$OD) δ 12.9, 14.5, 20.9, 23.8, 26.5, 30.3, 30.5, 30.5, 30.7, 30.8, 31.3, 33.1, 51.1, 74.3, 172.5;

ESMS calcd for C$_{20}$H$_{42}$NO$_2$ (M–Cl) 328.3, found 328.3.

Example 101

(2S,3S)-3-Azido-2-(N-tert-butoxycarbonylamino)-octadecane, 103

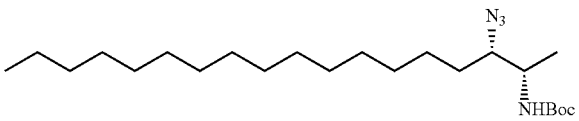

According to the method of Example 93, from alcohol 98 (50 mg, 0.13 mmol), azide 103 was obtained as a colorless oil (39 mg, 73% yield).

$R_f$ 0.64 (hexane/EtOAc 10:1);

$^1$H NMR (300 MHz, CD$_3$OD) δ 0.87 (t, 3H, J=6.8 Hz), 1.18 (d, 3H, J=6.8 Hz), 1.20–1.39 (m, 26H), 1.43 (s, 9H), 1.53–1.61 (m, 2H), 3.30–3.36 (m, 1H), 3.55–3.97 (m, 1H), 4.50 (d, 1H, J=9.2 Hz);

ESMS calcd for C$_{23}$H$_{46}$N$_4$O$_2$Na (M+Na) 433.3, found 433.4.

Example 102

(2S,3S)-3-Amino-2-(N-tert-butoxycarbonylamino)-octadecane, 104

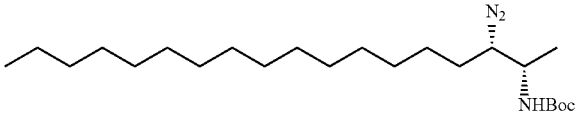

According to the method of Example 94, from azide 103 (15 mg, 0.03 mmol), amine 104 was obtained as a colorless oil (13 mg, 92% yield).

$^1$H NMR (300 MHz, CD$_3$OD) δ 0.87 (t, 3H, J=6.8 Hz), 1.10 (d, 3H, J=6.8 Hz), 1.21–1.40 (m, 26H), 1.43 (s, 9H), 1.45–1.47 (m, 2H), 2.70–2.75 (m, 1H), 3.60–3.55 (m, 1H), 4.90 (d, 1H, J=6.8 Hz);

ESMS calcd for C$_{23}$H$_{49}$N$_2$O$_2$ (M+H) 385.4, found 385.4.

Example 103

(2S,3 S)-2,3-Diamino-octadecane dihydrochloride, 105

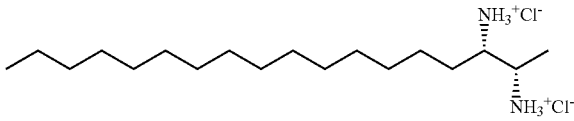

According to the method of Example 95, from N-Boc derivative 104 (13 mg, 0.03 mmol), dihydrochloride 105 was obtained as a white solid (11 mg, 75% yield).

$^1$H NMR (300 MHz, CD$_3$OD) δ 0.89 (t, 3H, J=6.8 Hz), 1.35 (d, 3H, J=6.8 Hz), 1.25–1.40 (m, 26H), 1.56–1.72 (m, 2H), 3.49–3.56 (m, 1H), 3.70–3.74 (m, 1H);

$^{13}$C NMR (75 MHz, CD$_3$OD) δ 13.1, 14.4, 22.7, 26.5, 27.8, 30.5, 30.8, 33.1, 54.1;

ESMS calcd for C$_{18}$H$_{41}$N$_2$ (M–HCl$_2$) 285.3, found 285.4.

Example 104

(2S,3R)-2-(N,N-Dimethylamino)-3-octadecanol, 106

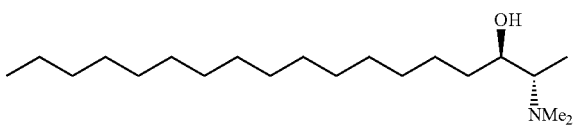

A mixture of aminoalcohol 1 (100 mg, 0.35 mmol), formaldehyde (37% w/w, aq. 142 mg, 1.75 mmol), NaB(OAc)$_3$H (370 mg, 1.75 mmol) and (CH$_2$Cl)$_2$ (2 mL) was stirred at room temperature for. 3 h. The reaction was quenched by the addition of NaHCO$_3$ (15 mL, sat. aq.) and extracted with EtOAc (3×25 mL). The combined extracts were dried over Na$_2$SO$_4$ and concentrated in vacuo to give 106 as a white solid (83 mg, 75% yield).

$^1$H NMR (500 MHz, CD$_3$OD) δ 0.80 (t, 3H, J=7.1 Hz), 0.92 (d, 3H, J=6.7 Hz), 1.15–1.25 (m, 26H), 1.30–1.40 (m, 2H), 2.19 (s, 6H), 2.30–2.35 (m, 1H), 3.60–3.65 (m, 1H);

$^{13}$C NMR (125 MHz, CD$_3$OD) δ 8.7, 14.9, 24.2, 27.7, 30.9, 31.2, 33.5, 36.8, 42.2, 65.0, 73.3;

ESMS calcd for C$_{20}$H$_{44}$NO (M+H) 314.3, found 314.4.

Example 105

(4S,5R)-4-Methyl-5-(n-pentadecyl)-1,3-oxazolidinone, 107

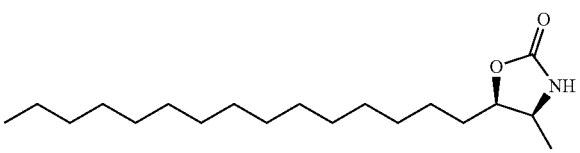

A mixture of aminoalcohol 1 (150 mg, 0.53 mmol) and carbonyl diimidazole (94 mg, 0.58 mmol) in THF (10 mL) was stirred at 60° C. for 3 h. Then, the solvent was removed in vacuo and the residue was dissolved in CH$_2$Cl$_2$ (40 mL), washed successively with HCl (2N, 40 mL), H$_2$O (40 mL) and brine (40 mL), dried over Na$_2$SO$_4$ and concentrated in vacuo to give oxazolidinone 107 as a white solid (160 mg, 98% yield).

R$_f$ 0.21 (hexane/EtOAc 2:1);

$^1$H NMR (300 MHz, CD$_3$OD) δ 0.80 (t, 3H, J=7.0 Hz), 1.02 (d, 3H, J=6.5 Hz), 1.15–1.30,(m, 26H), 1.40–1.55 (m, 2H), 3.81 (quint, 1H, J=6.5 Hz), 4.44–4.52 (m, 1H);

$^{13}$C NMR (75 MHz, CDCl$_3$) δ 14.1, 20.7, 22.7, 24.8, 29.3, 29.4, 29.4, 29.5, 29.7, 31.9, 34.1, 53.5, 84.2, 158.7;

ESMS calcd for C$_{19}$H$_{37}$NO$_2$Na (M+Na) 334.3, found 334.3.

Example 106

(2S,3R)-2-(N-Methylamino)-3-octadecanol, 108

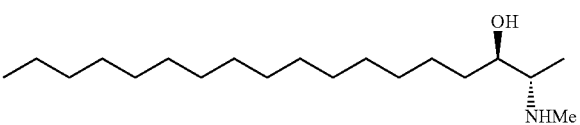

To a cold (0° C.) solution of 107 (160 mg, 0.52 mmol) in THF(20 mL), LiAlH$_4$ (1M in THF, 1.04 mL, 1.04 mmol), was added dropwise. The mixture was stirred overnight at room temperature. A further portion of LiAlH$_4$ (1.04 mL, 1.04 mmol) was added and the reaction left for 2 more days. The reaction was quenched with H$_2$O containing a few drops of NH$_4$OH (20 mL) and extracted with EtOAc (3×20 mL). The combined extracts were successively washed with. H$_2$O (30 mL) and brine (30 mL), dried over Na$_2$SO$_4$ and concentrated in vacuo. The crude was purified by column chromatography on silica (50% to 75% CH$_2$Cl$_2$/hexane to 100% CH$_2$Cl$_2$ to 10% MeOH/CHCl$_3$ and a few drops of NH$_4$OH) to give 108 as a white solid (35 mg, 23% yield).

$^1$H NMR (500 MHz, CD$_3$OD) δ 0.80 (t, 3H, J=7.1 Hz), 0.92 (d, 3H, J=6.7 Hz), 1.15–1.25 (m, 26H), 1.30–1.45 (m, 2H), 2.19 (s, 3H), 2.50–2.55 (m, 1H), 3.55–3.60 (m, 1H);

$^{13}$C NMR (125 MHz, CD$_3$OD) δ 13.3, 14.9, 24.2, 27.8, 30.9, 31.2, 33.5, 34.7, 36.8, 42.3, 60.5, 73.1;

ESMS calcd for C$_{19}$H$_{42}$NO (M+H) 300.3, found 300.3.

Example 107

(2S,3R)-2-Amino-N-(phenylthiocarbamoyl)-3-octadecanol, 109

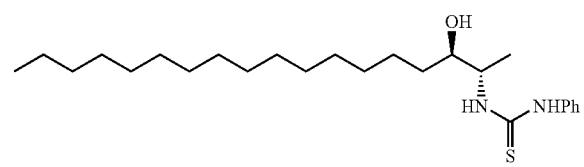

To a solution of aminoalcohol 1 (197 mg, 0.69 mmol) in THF (3.5 mL) at room temperature, PhNCS (0.165 mL, 1.38 mmol) was added. The reaction was stirred for 1 h, and then the solvents were evaporated in vacuo. The crude was purified by column chromatography on silica (hexane/EtOAc 5:1 to 2:1) to give phenylthiourea 109 as a white solid (246 mg, 85% yield).

R$_f$ 0.29 (hexane/EtOAc 2:1);

$^1$H NMR (300 MHz, CDCl$_3$) δ 0.85 (t, 3H, J=6.7 Hz), 1.08 (d, 3H, J=6.9 Hz), 1.20–1.30 (m, 26H), 1.35–1.45 (m, 2H), 2.20 (br s, 1H), 3.72–3.82 (m, 1H) 4.45–4.60 (m, 1H), 6.58 (d, 1H, J=8.6 Hz), 7.18–7.38 (m, 5H), 8.39 (br s, 1H);

$^{13}$C NMR (75 MHz, CDCl$_3$) δ 12.9, 14.0, 22.6, 25.8, 29.2, 29.4, 29.5, 29.5, 29.6, 31.8, 33.7, 54.5, 73.5, 124.4, 126.6, 129.9, 136.4, 179.0;

ESMS calcd for C$_{25}$H$_{43}$N$_2$OS (M–H) 419.3, found 419.2.

Example 108

(2S,3R)-2-Amino-N-(phenylcarbamoyl)-3-octadecanol, 110

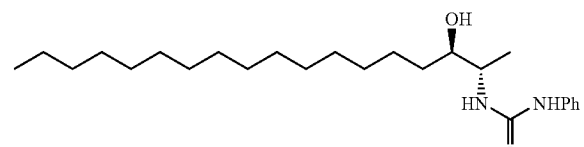

According to the method of Example 107, from aminoalcohol 1 (23 mg, 0.08 mmol) and PhNCO (18 µL, 0.16. mmol), phenylurea 110 was obtained as a white solid (15 mg, 46% yield).

R$_f$ 0.50 (hexane/EtOAc 5:1);

$^1$H NMR (300 MHz, CDCl$_3$) δ 0.87 (t, 3H, J=6.7 Hz), 1.11 (d, 3H, J=6.9 Hz), 1.20–1.30 (m, 26H), 1.35–1.45 (m, 2H), 2.17 (br s, 1H), 3.63–3.73 (m, 1H) 3.90–4.06 (m, 1H), 5.02 (d, 1H, J=7.2 Hz), 6.58 (br s, 1H), 7.05–7.12 (m, 1H), 7.25–7.34 (m, 4H);

ESMS calcd for C$_{25}$H$_{45}$N$_2$O$_2$ (M+H) 405.3, found 405.4.

Example 109

(2S,3R)-2-Amino-N-(n-butylcarbamoyl)-3-octadecanol, 111

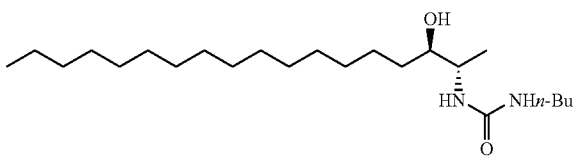

According to the method of Example 107, from aminoalcohol 1 (27 mg, 0.09 mmol) and n-BuNCO (21 μL, 0.19 mmol), n-butylurea 111 was obtained as a white solid (13 mg, 36% yield).

$R_f$ 0.25 (hexane/EtOAc 2:1);

$^1$H NMR (300 MHz, CDCl$_3$) δ 0.87 (t, 3H, J=6.9 Hz), 0.92.(t, 3H, J=7.2 Hz), 1.08 (d, 3H, J=6.9 Hz), 1.20–1.40 (m, 28H), 1.40–1.55 (m, 4H), 2.91 (br s, 1H), 3.14 (q, 2H, J=6.5 Hz), 3.61 (br s, 1H), 3.78–3.88 (m, 1H), 4.56–4.66 (m, 2H);

ESMS calcd for C$_{23}$H$_{49}$N$_2$O$_2$ (M+H) 385.4, found 385.4.

Example 110

(2S,3R)-2-(Methanesulfonamide)-3-octadecanol, 112

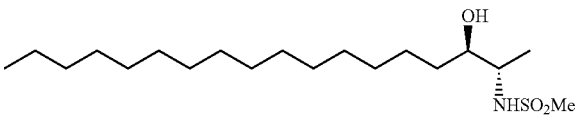

To a solution of aminoalcohol 1 (40 mg, 0.14 mmol) in CH$_2$Cl$_2$ (5.0 mL) at room temperature, ClSO$_2$Me (11 μL, 0.14 mmol) was added. After stirring for 1 h, the reaction was quenched with H$_2$O (10 mL), extracted with CH$_2$Cl$_2$ (3×10 mL), dried over Na$_2$SO$_4$ and concentrated in vacuo. The crude was purified by column chromatography on silica (hexane/EtOAc 4:1) to obtain sulfonamide 112 as a white solid (49 mg, 96% yield).

$R_f$ 0.13 (hexane/EtOAc 4:1);

$^1$H NMR (300 MHz, CD$_3$OD) δ 0.85 (t, 3H, J=6.8 Hz), 1.19 (t, 3H J=6.8 Hz), 1.20–1.40 (m, 26H), 1.47–1.53 (m, 2H), 1.86 (d, 1H,. J=5.1 Hz), 3.00 (s, 3H), 3.53 (t, 1H, J=6.1 Hz), 3.66–3.72 (m, 1H), 4.66 (d, 1H, J=8.1 Hz);

$^{13}$C NMR (75 MHz, CDCl$_3$) δ 12.0, 14.5, 16.4, 23.2, 26.9, 27.2, 30.6, 30.7, 30.8, 33.1, 34.2, 41.6, 55.3, 71.5;

ESMS calcd for C$_{18}$H$_{38}$NO (M–SO$_2$Me) 286.2, found 286.5.

Example 111

(2S,3R)-2-(Methanesulfonamide)-3-nonadecanol, 113

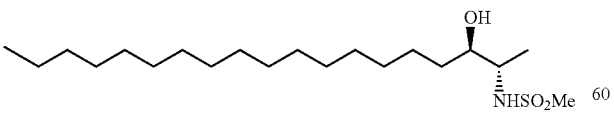

According to the method of Example 110, from aminoalcohol 2 (25 mg, 0.08 mmol), sulfonamide 113 was obtained as a white solid (29 mg, 94% yield).

$^1$H NMR (300 MHz, CD$_3$OD) δ 0.87 (t, 3H, J=6.4 Hz), 1.17 (d, 3H, J=6.4 Hz), 1.20–1.40 (m, 28H), 1.46–1.53 (m, 2H), 1.98–2.05 (m, 1H), 2.97–3.03 (m, 1H), 3.47–3.58 (m, 1H), 3.68–3.74 (m, 1H), 4.77–4.83 (m, 1H);

$^{13}$C NMR (75 MHz, CDCl$_3$) δ 14.3, 15.5, 22.9, 26.2, 29.5, 29.7, 29.8, 29.9, 32.1, 33.4, 42.0, 54.0, 74.6;

ESMS calcd for C$_{19}$H$_{40}$NO (M–SO$_2$Me) 300.3, found 300.3.

Example 112

(2S,3R)-2-(2,2,2-Trifluoroacetylamino)-3-octadecanol, 114, and (2S,3R)-2-(2,2,2-trifluoroacetylamino)-O-(2,2,2-trifluoroacetyl)-octadecanol, 115

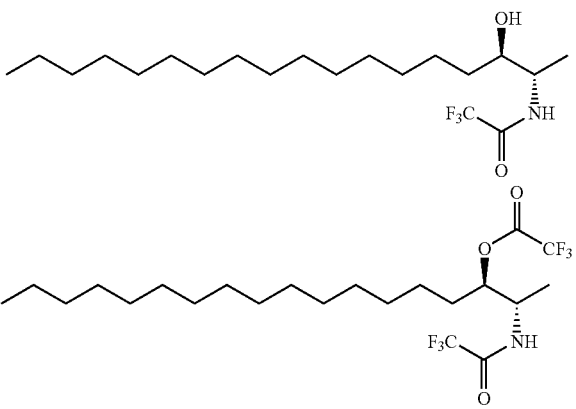

To a solution of aminoalcohol 1 (27 mg, 0.09 mmol) in CH$_2$Cl$_2$ (5.0 mL) at room temperature, trifluoroacetic anhydride (12.8 μL, 0.09 mmol) was added. After stirring for 1 h, the solvents were removed in vacuo. The crude was purified by column chromatography on silica (hexane/CH$_2$Cl$_2$ 1:1) to obtain 114 (9 mg, 25% yield) $R_f$ 0.34 (hexane/CH$_2$Cl$_2$ 1:1) and 115 (11 mg, 24% yield) $R_f$ 0.52 (hexane/CH$_2$Cl$_2$ 1:1) as white solids.

114: $^1$H NMR (300 MHz, CD$_3$OD) δ 0.85 (t, 3H, J=6.9 Hz), 1.05 (d, 3H, J=7.0 Hz), 1.19–1.38 (m, 26H), 1.45–1.53 (m, 2H), 3.60–3.66 (m, 1H), 3.93–3.98 (m, 1H), 6.65 (d, 1H, J=7.5 Hz);

$^{13}$C NMR (75 MHz, CDCl$_3$) δ 12.9, 14.3, 15.4, 22.9, 25.9, 29.5, 29.7, 29.8, 31,8, 32.1, 34.2, 49.6, 73.2, 76.8, 114.4, 118.2, 121.8, 151.4, 156.9;

ESMS calcd for C$_{20}$H$_{38}$F$_3$NO$_2$Na (M+Na) 404.3, found 404.8.

115: $^1$H NMR (300 MHz, CD$_3$OD) δ 0.89 (t, 3H, J=7.6 Hz), 1.20–1.39 (m, 26H), 2.46–2.55 (m, 2H), 4.01–4.43 (m,1H), 4.95–5.24 (m, 1H), 6.00–6.34 (m, 1H).

Example 113

(2S,3R)-2-(2,2,2-Trifluoroacetylamino)-3-nonadecanol, 116, and (2S,3R)-2-(2,2,2-trifluoroacetylamino)-O-(2,2,2-trifluoroacetyl)-nonadecanol, 117

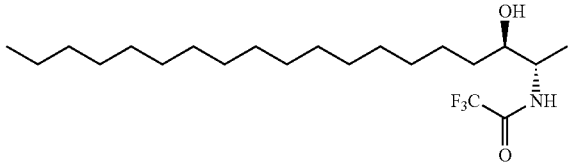

-continued

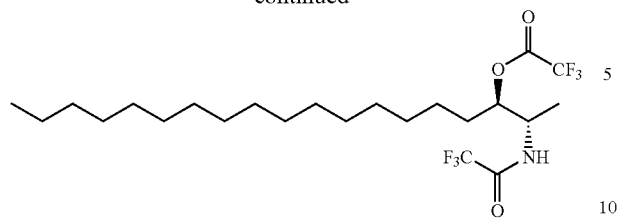

According to the method of Example 112, from aminoalcohol 2 (22 mg, 0.07 mmol), 116 (6 mg, 22% yield) and 117 (8 mg, 23% yield) were obtained as white solids.

116: $^1$H NMR (300 MHz, CD$_3$OD) δ 0.85 (t, 3H, J=6.8 Hz), 1.01 (d, 3H, J=6.8 Hz), 1.23–1.41 (m, 28H), 1.45–1.53 (m, 2H), 3.65–3.73 (m, 1H), 3.96–4.06 (m, 1H), 6.68–6.73 (m, 1H).

117: $^1$H NMR (300 MHz, CD$_3$OD) δ 0.88 (t, 3H, J=7.6 Hz,), 1.25–1.38 (m, 26H), 2.47–2.60 (m, 2H), 4.00–4.40 (m, 1H), 4.97–5.28 (m, 1H), 6.01–6.35 (m, 1H).

Example 114

(2S,3R)-2-Amino-N-(trans-cinnamoyl)-3-octadecanol, 118

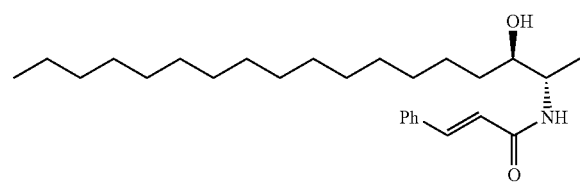

To a solution of aminoalcohol 1 (30 mg, 0.10 mmol) in CH$_2$Cl$_2$ (3.0 mL) at room temperature, pyridine (58 mL, 0.11 mmol) and cinnamoyl chloride (16.6 mg, 0.36 mmol) were added. After stirring for 1 h, the reaction was quenched with H$_2$O (10 mL), extracted with CH$_2$Cl$_2$ (3×10 mL), dried over Na$_2$SO$_4$ and concentrated in vacuo. The crude was purified by column chromatography on silica (hexane/EtOAc 4:1) to obtain 118 as a white solid (32 mg, 74% yield).

R$_f$ 0.31(hexane/EtOAc 2:1);

$^1$H NMR (300 MHz, CD$_3$OD) δ 0.87 (t, 3H, J=6.9 Hz), 1.16 (d, 3H, J=6.9 Hz), 1.21–1.40 (m, 26H), 1.33–1.40 (m, 2H), 2.28–2.35 (m, 1H), 3.64–3.71 (m, 1H), 4.06–4.18 (m, 1H), 5.92 (d, 1H, J=15.6 Hz), 6.40 (d, 1H, J=15.6 Hz), 7.31–7.36 (m, 3H), 7.41–7.50 (m, 2H), 7.62 (d, 1H, J=15.6 Hz);

$^{13}$C NMR (75 MHz, CDCl3) δ 14.9, 25.3, 26.2, 29.5, 29.9, 33.8, 49.9, 74.3, 124.2, 126.8, 129.8, 130.9, 136.1, 165.1;

ESMS calcd for C$_{27}$H$_{45}$NO$_2$Na (M+Na) 438.3, found 438.3.

Example 115

(2S,3R)-2-Amino-N-[trans-3-(trifluoromethyl)-cinnamoyl]-3-octadecanol, 119

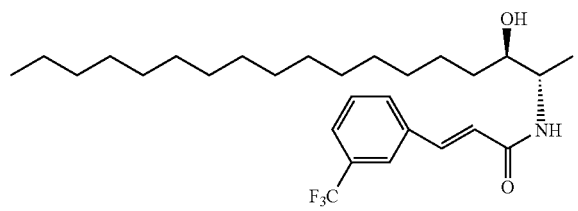

According to the method of Example 114, from aminoalcohol 1 (30 mg, 0.10 mmol) and 3-(trifluoromethyl)-cinnamoyl chloride (24.6 mg, 0.10 mmol), amide 119 was obtained as a white solid (28 mg, 56% yield).

R$_f$ 0.30 (hexane/EtOAc 2:1);

$^1$H NMR (300 MHz, CD$_3$OD) δ 0.87 (t, 3H, J=6.9 Hz), 1.16 (d, 3H, J=6.9 Hz), 1.20–1.40 (m, 26H), 1.35–1.41 (m, 2H), 3.68–3.74 (m, 1H), 3.98–4.20 (m, 1H), 6.06 (d, 1H, J=9.6 Hz), 6.45 (d, J=6.9 Hz, 1H), 7.48–7.78 (m, 4H);

$^{13}$C NMR (75 MHz, CDCl$_3$) δ 14.1, 22.9 26.2, 29.6, 29.8, 29.9, 32.1, 33.9, 49.9, 74.4, 122.8, 124.1, 124.2, 126.3, 129.5, 131.3, 135.8, 139.7, 165.2;

ESMS calcd for C$_{28}$H$_{44}$F$_3$NO$_2$Na (M+Na) 506.3, found 506.4.

Example 116

(2S,3R)-2-Amino-N-(palmitoyl)-3-octadecanol, 120

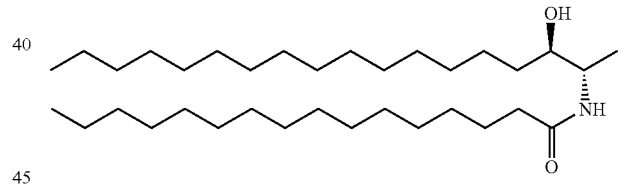

To a solution of aminoalcohol 1 (30 mg, 0.10 mmol) in CH$_2$Cl$_2$ (3.0 mL) at room temperature, palmitic acid (28 mg, 0.11 mmol), EDC (50.2 mg, 0.26 mmol), DIPEA (39 μL, 0.15 mmol) and DMAP (1.2 mg, 0.01 mmol) were added. After stirring for 2 h, the reaction was quenched with H$_2$O (10 mL), extracted with CH$_2$Cl$_2$ (3×10 mL), dried over Na$_2$SO$_4$ and concentrated in vacuo. The crude was purified by column chromatography on silica (hexane/EtOAc 4:1) to obtain 120 as a white solid (48 mg, 87% yield).

R$_f$ 0.21 (hexane/EtOAc 4:1);

$^1$H NMR (300 MHz, CD$_3$OD) δ 0.85–0.94 (m, 6H), 1.08 (d, 3H, J=7.1 Hz), 1.20–1.40 (m, 52H), 1.58–1.65 (m, 2H) 2.16 (t, 2H, J=7.1Hz), 2.29–2.33 (m, 1H), 3.58–3.64 (m, 1H), 3.93–4.13 (m, 1H), 5.72 (d, 1H, J=7.1 Hz);

$^{13}$C NMR (75 MHz, CDCl$_3$) δ 14.1, 15.2, 22.7, 25.8, 25.9, 29.2, 29.3, 29.5, 29.6, 29.7, 31.9, 33.5, 36.9, 49.4, 65.8, 74.4, 173.1;

ESMS calcd for C$_{34}$H$_{69}$NO$_2$Na (M+Na) 546.5, found 546.8.

Example 117

(2S,3R)-2-[2-(tert-Butoxycarbonylaminio)-3-methylbutyramide)]-3-octadecanol, 121

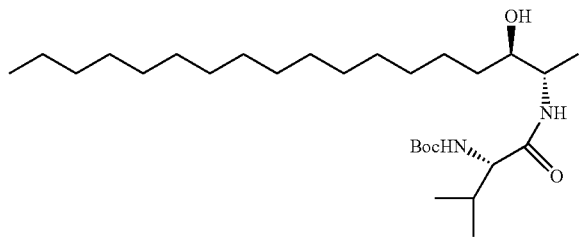

To a solution of aminoalcohol 1 (30 mg, 0.10 mmol) in CH$_2$Cl$_2$ (3.0 mL) at room temperature, N-Boc-valine (23 mg, 0.11 mmol), EDC (50.2 mg, 0.26 mmol), DIPEA (39 μL, 0.15 mmol) and DMAP (1.2 mg, 0.01 mmol) were added. After stirring for 2 h, the reaction was quenched with H$_2$O (10 mL), extracted with CH$_2$Cl$_2$ (3×10 mL), dried over Na$_2$SO$_4$ and concentrated in vacuo. The crude was purified by column chromatography on silica (hexane/EtOAc 4:1) to obtain 121 as a white solid (48 mg, 87% yield).

R$_f$ 0.13 (hexane/EtOAc 4:1);

$^1$H NMR (300 MHz, CD$_3$OD) δ 0.86 (t, 3H, J=6.9 Hz), 0.91 (d, 3H, J=6.9 Hz), 0.96 (d, 3H, J=6.9 Hz), 1.08 (d, 3H, J=6.9 Hz), 1.20–1.40 (m, 26H), 1.38–1.46 (m, 11H), 1.99–2.23 (m, 1H), 2.33–2.78 (m, 1H), 3.64 (m, 1H), 3.83 (t, 1H, J=6.3 Hz), 3.98 (m, 1H), 5.06 (d, 1H, J=6.8 Hz), 6.29 (d, 1H, J=7.8 Hz);

$^{13}$C NMR (75 MHz, CDCl$_3$) δ 13.7, 14.1, 17.8, 19.3, 22.7,.26.0, 28.3, 29.3, 29.5, 29.7, 30.6, 31.9, 33.5, 49.6, 60.4, 73.8, 157.4, 171.3;

ESMS calcd for C$_{28}$H$_{57}$N$_2$O$_4$ (M+Ha) 485.4, found 485.7.

Example 118

(2S,3R)-2-[2-Amino-3-methylbutyramide)]-3-octadecanol hydrochloride, 122

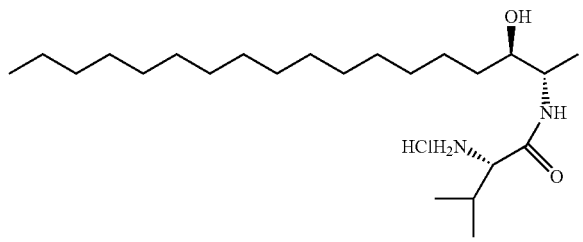

According to the method of Example 95, from N-Boc derivative 121 (24 mg, 0.05 mmol), hydrochloride 122 was obtained as a white solid (15 mg, 75% yield).

$^1$H NMR (300 MHz, CD$_3$OD) δ 0.87 (t, 3H, J=6.8 Hz), 1.07–1.11 (m, 6H), 1.13 (d, 3H, J=6.8 Hz), 1.21–1.40 (m, 26H), 1.41–1.52 (m, 2H), 2.09–2.11 (m, 1H), 3.40–3.47 (m, 1H), 3.66–3.77 (m, 1H), 3.87–3.93 (m, 1H);

$^{13}$C NMR (75 MHz, CDCl$_3$) δ 12.7, 13.1, 16.7, 17.8, 18.3, 21.6, 25.2, 27.2, 28.3, 28.7, 29.6, 30.9, 32.3, 49.6, 66.0,. 72.5, 166.7;

ESMS calcd for C$_{23}$H$_{49}$N$_2$O$_2$ (M–Cl) 385.3, found 385.3.

Example 119

(2S)-2-(N-tert-Butoxycarbonylamino)-3-heptadecanone, 123

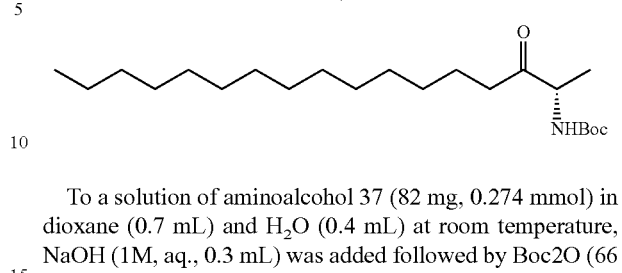

To a solution of aminoalcohol 37 (82 mg, 0.274 mmol) in dioxane (0.7 mL) and H$_2$O (0.4 mL) at room temperature, NaOH (1M, aq., 0.3 mL) was added followed by Boc2O (66 mg, 0.301 mmol). After stirring for 2 h, the reaction was diluted with EtOAc (10 mL) and KHSO$_4$ (10% aq., 10 mL) was added. The layers were separated and the aqueous layer extracted with EtOAc (3×10 mL). The organic layers were dried over Na$_2$SO$_4$ and concentrated in vacuo to obtain the crude N-Boc derivative as a white solid. To a cold (–78° C.) solution of (COCl)$_2$ (2M in CH$_2$Cl$_2$, 0.22 mL, 0.447 mmol) in CH$_2$Cl$_2$ (4.5 mL), DMSO (0.063 mL, 0.894 mmol) was added dropwise. After stirring at –78° C. for 15 min, a solution of the N-Boc derivative (69 mg, 0.179 mmol) in CH$_2$Cl$_2$ (2 mL) was added dropwise. The mixture was stirred at –78° C. for 1 h, and then Et$_3$N (0.187 mL, 1.34 mmol) was added. The reaction was warmed up to 0° C. and stirred for 15 min, followed by the addition of NH$_4$Cl (15 mL, sat. aq.). The crude was extracted with CH$_2$Cl$_2$ (3×15 mL), washed successively with NaHCO$_3$ (30 mL, sat. aq.) and brine (30 mL), dried over Na$_2$SO$_4$ and concentrated in vacuo. The crude was purified by column chromatography on silica (hexane/EtOAc 5:1) to obtain ketone 123 as a white solid (40 mg, 56% yield) together with unreacted starting material (30 mg). R$_f$ 0.42 (hexane/EtOAc 5:1);

$^1$H NMR (300 MHz, CDCl$_3$) δ 0.85 (t, 3H, J=6.4 Hz), 1.20–1.37 (m, 25H), 1.42 (s, 9H), 1.54–1.62 (m, 2H), 2.38–2.56 (m, 2H), 4.29 (quint, 1H, J=6.5 Hz), 5.28 (br d, 1H, J=5.2 Hz);

$^{13}$C NMR (75 MHz, CDCl$_3$) δ 14.0, 17.9, 22.6, 23.5, 28.3, 29.2, 29.3, 29.4, 29.5, 29.6, 31.9, 39.1, 55.0, 209.7;

ESMS calcd for C$_{22}$H$_{43}$NO$_3$Na (M+Na) 392.3, found 392.3.

Example 120

(2S)-2-Amino-3-heptadecanone hydrochloride, 124

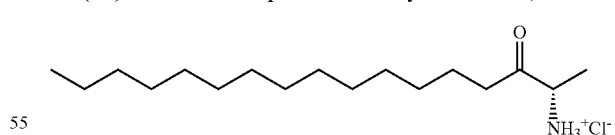

According to the method of Example 95, from ketone 123 (33.5 mg, 0.091 mmol), hydrochloride 124 was obtained as a white solid (22 mg, 79% yield).

$^1$H NMR (300 MHz, CD$_3$OD) δ 0.89 (t, 3H, J=6.9 Hz), 1.20–1.35 (m, 22H), 1.51 (d, 3H, J=7.4 Hz), 1.55–1.65. (m, 2H), 2.50–2.72 (m, 2H), 4.13 (q, 1H, J=7.4 Hz);

$^{13}$C NMR (75 MHz, CD$_3$OD) δ 14.4, 15.7, 23.7, 24.3, 30.1, 30.5, 30.5, 30.6, 30.7, 30.8, 33.1, 39.2, 55.8, 207.4;

ESMS calcd for C$_{17}$H$_{36}$NO (M–Cl) 270.3, found 270.2.

Example 121

(2S)-2-(N-tert-Butoxycarbonylamino)-3-octadecanone, 125

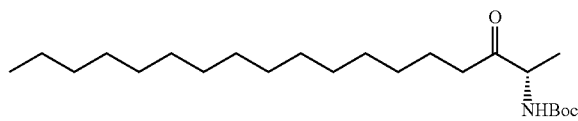

According to the method of Example 119, from aminoalcohol 1 (53 mg, 0.186 mmol), ketone 125 was obtained as a white solid (27 mg, 38% yield), together with unreacted starting alcohol (24 mg). $R_f$ 0.42 (hexane/EtOAc 5:1);

$^1$H NMR (300 MHz, CDCl$_3$) δ 0.87 (t, 3H, J=6.4 Hz), 1.20–1.37 (m, 27H), 1.43 (s, 9H), 1.54–1.62 (m, 2H), 2.38–2.56 (m, 2H), 4.30 (quint, 1H, J=6.8 Hz), 5.27. (br s, 1H);

$^{13}$C NMR (75 MHz, CDCl$_3$) δ 14.1, 17.9, 22.7, 23.6, 28.3, 29.2, 29.3, 29.4, 29.6, 29.7, 31.9, 39.2, 55.0, 209.7;

ESMS calcd for C$_{23}$H$_{45}$NO$_3$Na (M+Na) 406.3, found 406.3.

Example 122

(2S)-2-Amino-3-octadecanone hydrochloride, 126

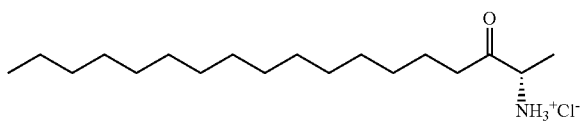

According to the method of Example 95, from ketone 125 (24 mg, 0.063 mmol), hydrochloride 126 was obtained as a white solid (17 mg, 85% yield).

$^1$H NMR (300 MHz, CD$_3$OD) δ 0.89 (t, 3H, J=6.9 Hz), 1.20–1.35 (m, 24H), 1.51 (d, 3H, J=7.4 Hz), 1.55–1.65 (m, 2H), 2.50–2.72 (m, 2H), 4.13 (q, 1H, J=7.4 Hz);

$^{13}$C NMR (75 MHz, CD$_3$OD) δ 14.4, 15.7, 23.7, 24.3, 30.1, 30.5, 30.5, 30.6, 30.8, 33.1, 39.2, 55.8, 207.4;

ESMS calcd for C$_{18}$H$_{38}$NO (M−Cl) 284.3, found 284.3.

Example 123

(2S)-2-Amino-3-octadecanoneoxime, 127

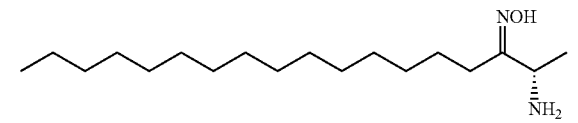

To a solution of ketone 126 (108 mg, 0.34 mmol) in 2.5 mL of EtOH, NH$_2$OH.HCl (117 mg, 1.69 mmol) and AcONa (249 mg, 3.04 mmol) were added. The mixture was stirred at 80° C. for 8 h, and then the solvent was evaporated in vacuo. The residue was suspended in H$_2$O, filtered and washed with H$_2$O. The collected solid was recyrstallised from EtOAc to obtain oxime 127 as a white solid (70 mg, 69% yield).

$^1$H NMR (300 MHz, CD$_3$OD) δ 0.90 (t, 3H, J=6.7 Hz), 1.20–1.35 (m, 27H), 1.55–1.65 (m, 2H), 2.18 (ddd, 1H, J=12.9, 10.1, 6.0 Hz), 2.47 (ddd, 1H, J=12.9, 9.6, 6.4 Hz), 3.72 (q, 1H, J=6.7 Hz);

$^{13}$C NMR (75 MHz, CD$_3$OD) δ 14.5, 18.3, 23.7, 24.0, 26.6, 26.7, 30.4, 30.5, 30.7, 30.8, 31.0, 33.1, 50.2, 158.0;

ESMS calcd for C$_{18}$H$_{39}$N$_2$O (M+H) 299.3, found 299.3.

Example 124

(2S)-2-(N-tert-Butoxycarbonylamino)-3-nonadecanone, 128

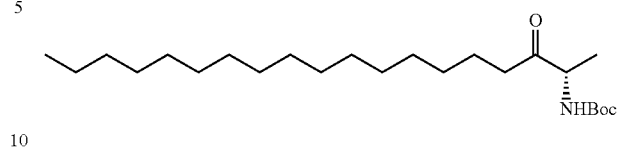

According to the method of Example 119, from aminoalcohol 2 (59 mg, 0.197 mmol), ketone 128 was obtained as a white solid (44 mg, 56% yield).

$R_f$ 0.42 (hexane/EtOAc 5:1);

$^1$H NMR (300 MHz, CDCl$_3$) δ 0.85 (t, 3H, J=6.4 Hz), 1.20–1.37 (m, 29H), 1.42 (s, 9H), 1.54–1.62 (m, 2H), 2.38–2.56 (m, 2H), 4.28 (quint, 1H, J=6.7 Hz), 5.29 (br d, 1H, J=6.2 Hz);

$^{13}$C NMR (75 MHz, CDCl$_3$) δ 14.0, 17.8, 22.6, 23.5, 28.3, 29.2, 29.3, 29.4, 29.5, 29.6, 31.9, 39.1, 55.0, 209.7;

ESMS calcd for C$_{24}$H$_{47}$NO$_3$Na (M+Na) 420.4, found 420.2.

Example 125

(2S)-2-Amino-3-nonadecanone hydrochloride, 129

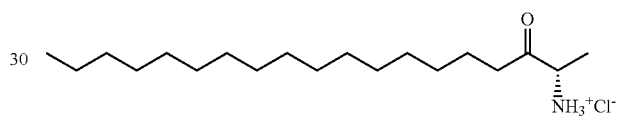

According to the method of Example 95, from ketone 128 (33 mg, 0.083 mmol), hydrochloride 129 was obtained as a white solid (25 mg, 90% yield).

$^1$H NMR (300 MHz, CD$_3$OD) δ 0.89 (t, 3H, J=6.9 Hz), 1.20–1.35 (m, 26H), 1.51 (d, 3H, J=7.4 Hz), 1.55–1.65 (m, 2H), 2.50–2.72 (m, 2H), 4.13 (q, 1H, J=7.4 Hz);

$^{13}$C NMR (75 MHz, CD$_3$OD) δ 14.4, 15.7, 23.7, 24.3, 30.1, 30.5, 30.5, 30.6, 30.8, 33.1, 39.2, 55.8, 207.4;

ESMS calcd for C$_{19}$H$_{40}$NO (M−Cl) 298.3, found 298.3.

Example 126

(2S)-2-(N-tert-Butoxycarbonylamin)-3-eicosadecanone, 130

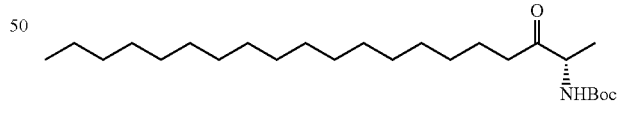

According to the method of Example 119, from aminoalcohol 3 (81 mg, 0.258 mmol), ketone 130 was obtained as a white solid (75 mg, 70% yield).

$R_f$ 0.42 (hexane/EtOAc 5:1);

$^1$H NMR (300 MHz, CDCl$_3$) δ 0.86 (t, 3H, J=6.2 Hz), 1.20–1.37 (m, 31H), 1.42 (s, 9H), 1.54–1.62 (m, 2H), 2.38–2.56 (m, 2H), 4.29 (quint, 1H, J=6.5 Hz), 5.29 (br d, 1H, J=5.4 Hz);

$^{13}$C NMR (75 MHz, CDCl$_3$) δ 14.0, 17.8, 22.6, 23.5, 28.3, 29.2, 29.3, 29.4, 29.5, 29.6, 31.9, 39.1, 55.0, 209.6;

ESMS calcd for C$_{25}$H$_{49}$NO$_3$Na (M+Na) 434.4, found 434.3.

Example 127

(2S)-2-Amino-3-eicosadecanone hydrochloride, 131

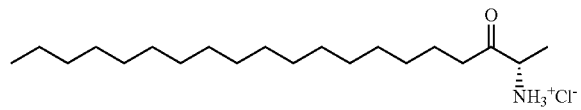

According to the method of Example 95, from ketone 130 (47 mg, 0.114 mmol), hydrochloride 131 was obtained as a white solid (30.5 mg, 77% yield).

$^1$H NMR (300 MHz, CD$_3$OD) δ 0.89 (t, 3H, J=6.9 Hz), 1.20–1.35 (m, 28H), 1.50 (d, 3H, J=7.2 Hz), 1.55–1.65 (m, 2H), 2.50–2.72 (m, 2H), 4.13 (q, 1H, J=7.2 Hz);

$^{13}$C NMR (75 MHz, CD$_3$OD) δ 14.4, 15.7, 23.7, 24.3, 30.1, 30.5, 30.5, 30.6, 30.7, 30.8, 33.1, 39.2, 55.8, 207.4;

ESMS calcd for C$_{20}$H$_{42}$NO (M−Cl) 312.3, found 312.3.

Example 128

(3S)-3-(N-tert-Butoxycarbonylamino)-4-nonadecanone, 132

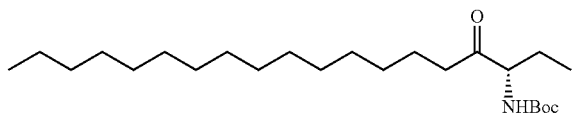

According to the method of Example 119, from aminoalcohol 57 (82 mg, 0.274 mmol), ketone 132 was obtained as a white solid (54 mg, 50% yield).

R$_f$ 0.42 (hexane/EtOAc 5:1);

$^1$H NMR (300 MHz, CDCl$_3$) δ 0.86 (t, 6H, J=7.0 Hz), 1.20–1.35 (m, 24H), 1.43 (s, 9H), 1.55–1.65 (m, 3H), 1.84–1.96 (m, 1H), 2.38–2.56 (m, 2H), 4.28 (q, 1H, J=5.5 Hz), 5.24 (br d, 1H, J=6.9 Hz);

$^{13}$C NMR (75 MHz, CDCl$_3$) δ 9.2, 14.0, 22.6, 23.5, 24.8, 28.3, 29.2, 29.3, 29.4, 29.6, 29.6, 31.9, 39.8, 60.1, 209.4;

ESMS calcd for C$_{24}$H$_{47}$NO$_3$Na (M+Na) 420.4, found 420.3.

Example 129

(3S)-3-Amino-4-nonadecanone hydrochloride, 133

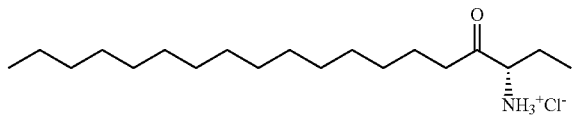

According to the method of Example 95, from ketone 132 (36.5 mg, 0.092 mmol), hydrochloride 133 was obtained as a white solid (29 mg, 95% yield).

$^1$H NMR (300 MHz, CD$_3$OD) δ 0.89 (t, 3H, J=6.7 Hz), 1.00 (t, 3H, J=7.5 Hz), 1.20–1.35 (m, 24H), 1.55–1.65 (m, 2H), 1.82–1.96 (m, 1H), 2.00–2.12 (m, 1H), 2.50–2.72 (m, 2H), 4.11 (dd, 1H, J=7.2, 4.5 Hz);

$^{13}$C NMR (75 MHz, CD$_3$OD) δ 9.3, 14.5, 23.8, 23.9, 24.3, 30.1, 30.5, 30.5, 30.6, 30.7, 30.8, 33.1, 39.8, 61.0, 207.1;

ESMS calcd for C$_{19}$H$_{40}$NO (M−Cl) 298.3, found 298.3.

Example 130

(2R)-2-(N-tert-Butoxycarbonylamino)-3-octadecanone, 134

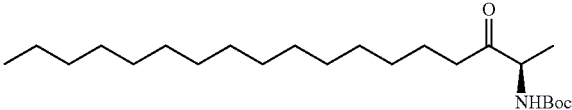

According to the method of Example 119, from aminoalcohol 81 (53 mg, 0.186 mmol), ketone 134 was obtained as a white solid (40 mg, 56% yield).

R$_f$ 0.42 (hexane/EtOAc 5:1);

$^1$H NMR (300 MHz, CDCl$_3$) δ 0.87 (t, 3H, J=6.4 Hz), 1.20–1.37 (m, 27H), 1.43 (s, 9H), 1.54–1.62 (m, 2H), 2.38–2.56 (m, 2H), 4.30 (quint, 1H, J=6.8 Hz), 5.27 (br s, 1H);

$^{13}$C NMR (75 MHz, CDCl$_3$) δ 14.1, 17.9, 22.7, 23.6, 28.3, 29.2, 29.3, 29.4, 29.6, 29.7, 31.9, 39.2, 55.0, 209.7;

ESMS calcd for C$_{23}$H$_{45}$NO$_3$Na (M+Na) 406.3, found 406.2.

Example 131

(2R)-2-Amino-3-octadecanone hydrochloride, 135

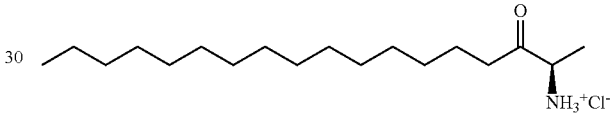

According to the method of Example 95, from ketone 134 (30 mg, 0.078 mmol), hydrochloride 135 was obtained as a white solid (24 mg, 96% yield).

$^1$H NMR (300 MHz, CD$_3$OD) δ 0.89 (t, 3H, J=6.9 Hz), 1.20–1.35 (m, 24H), 1.51 (d, 3H, J=7.4 Hz), 1.55–1.65 (m, 2H), 2.50–2.72 (m, 2H), 4.13 (q, 1H, J=7.4 Hz);

$^{13}$C NMR (75 MHz, CD$_3$OD) δ 14.4, 15.7, 23.7, 24.3, 30.1, 30.5, 30.5, 30.6, 30.8, 33.1, 39.2, 55.8, 207.4;

ESMS calcd for C$_{18}$H$_{38}$NO (M−Cl) 284.3, found 284.2.

Example 132

(2S,3R)-2-Amino-1-(tert-butyldiphenylsilyloxy)-octadec4-en-3-ol, 136

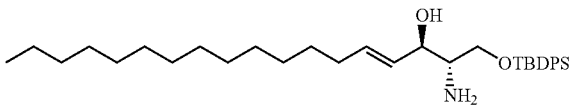

To a solution of D-erythro-sphingosine (46 mg, 0.153 mmol) in CH$_2$Cl$_2$ (1.5 mL) at room temperature, Et$_3$N (32 μL, 0.230 mmol), TBDPSCl (44 μL, 0.169 mmol) and 4-DMAP (ca. 5 mg, cat.) were added. After stirring for 4 h, the reaction was quenched with H$_2$O (10 mL), extracted with EtOAc (3×10 mL), dried over Na$_2$SO$_4$ and concentrated in vacuo. The crude was purified by column chromatography on silica (hexane/EtOAc 5:1 to 100% EtOAc) to obtain 136 as a colorless oil (33 mg, 40% yield).

R$_f$ 0.20 (hexane/EtOAc 1:5);

$^1$H NMR (300 MHz, CDCl$_3$) δ 0.88 (t, 3H, J=6.9 Hz), 1.06 (s, 9H), 1.20–1.40 (m, 22H), 1.91 (br s, 3H), 2.01 (q, 2H, J=6.5 Hz), 2.93 (q, 1H, J=5.5 Hz), 3.69 (d, 2H, J=4.5

Hz), 4.09 (t, 1H, J=6.1 Hz), 5.40 (dd, 1H, J=15.3, 6.9 Hz), 5.73 (dt, 1H, J=15.4, 6.5 Hz), 7.35–7.46 (m, 6H), 7.64–7.68 (m, 4H);
$^{13}$C NMR (75 MHz, CDCl$_3$) δ 14.1, 19.2, 22.7, 26.8, 29.2, 29.2, 29.3, 29.5, 29.6, 29.7, 31.9, 32.3, 56.3, 66.2, 74.6, 127.7, 128.9, 129.8, 133.1, 134.1, 135.5;
ESMS calcd for C$_{34}$H$_{56}$NO$_2$Si (M+H) 538.4, found 538.4.

Example 133

(4S,5R)-4-(tert-Butyldimethylsilyloxymethyl)-5-(n-pentadec-2'-enyl)-1,3-oxazolidinone, 137

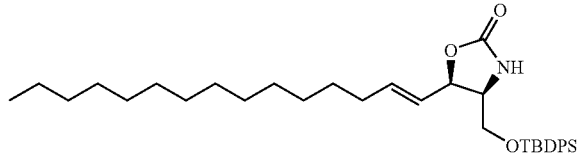

According to the method of Example 105, from aminoalcohol 136 (33 mg, 0.061 mmol), oxazolidinone 137 was obtained as a colorless oil (32 mg, 92% yield).
R$_f$ 0.60 hexane/EtOAc 1:1);
$^1$H NMR (300 MHz, CDCl$_3$) δ 0.86 (t, 3H, J=7.0 Hz), 1.06 (s, 9H), 1.20–1.40 (m, 22H), 2.00 (q, 2H, J=6.9 Hz), 3.58 (dd, 1H, J=10.6, 4.7 Hz), 3.64 (dd, 1H, J=10.6, 6.7 Hz), 3.82–3.88 (m, 1H), 5.02 (t, 1H, J=8.1 Hz), 5.32 (br s, 1H), 5.51 (dd, 1H, J=15.4, 8.1 Hz), 5.83 (dt, 1H, J=15.4, 6.5 Hz), 7.37–7.46 (m, 6H), 7.61–7.65 (m, 4H);
$^{13}$C NMR (75 MHz, CDCl$_3$) δ 14.1, 19.1, 22.7, 26.7, 28.7, 29.1, 29.3, 29.4, 29.5, 29.6, 31.9, 32.1, 57.2, 63.1, 79.4, 122.1, 127.9, 130.0, 132.7, 135.5, 138.4, 158.9;
ESMS calcd for C$_{35}$H$_{53}$NO$_3$SiNa (M+Na) 586.4, found 586.5.

Example 134

(4S,5R)-4-(Hydroxymethyl)-5-(n-pentadec-2'-enyl)-1,3-oxazolidinone, 138

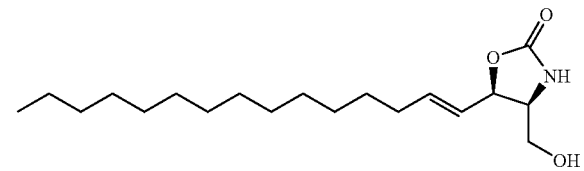

To a solution of 137 (32 mg, 0.057 mmol) in THF (0.6 mL) at room temperature, TBAF (1M in THF, 113 μL, 0.113 mmol) was added. After stirring for 30 min, the reaction was quenched with H$_2$O (10 mL), extracted with EtOAc (3×10 mL), dried over Na$_2$SO$_4$ and concentrated in vacuo. The crude was purified by column chromatography on silica (hexane/EtOAc 1:1 to 1:5) to obtain alcohol 138 as a white solid (13 mg, 70% yield).
R$_f$ 0.27 (hexane/EtOAc 1:5);
$^1$H NMR (300 MHz, CD$_3$OD) δ 0.90 (t, 3H, J=6.7 Hz), 1.25–1.50 (m, 22H), 2.12 (q, 2H, J=6.9 Hz), 3.51 (dd, 1H, J=11.6, 5.9 Hz), 3.58 (dd, 1H, J=11.6, 4.0 Hz), 3.84 (ddd, 1H, J=8.4, 5.9, 4.2 Hz), 5.10 (t, 1H, J=8.2 Hz), 5.67 (dd, 1H, J=15.4, 8.2 Hz), 5.90 (dt, 1H, J=15.4, 6.7 Hz);
$^{13}$C NMR (75 MHz, CD$_3$OD) δ 14.5, 23.8, 30.0, 30.2, 30.5, 30.6, 30.8, 33.1, 33.3, 58.7, 62.2, 81.5, 124.4, 139.1, 168.1;
ESMS calcd for C$_{19}$H$_{35}$NO$_3$Na (M+Na) 348.3, found 348.2.

Example 135

(4S,5R)-4-(Fluoromethyl)-5-(n-pentadec-2'-enyl)-1,3-oxazolidinone, 139

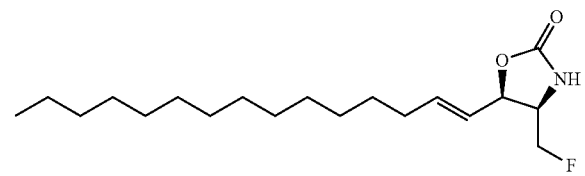

To a cold (−78° C.) solution of 138 (11.5 mg, 0.035 mmol) in THF (0.35 mL), DAST (14 μL, 0.106 mmol) was added. After stirring for 30 min, the mixture was warmed up to room temperature and stirred for 2 h. The reaction was quenched with NaHCO$_3$ (5 mL), extracted with EtOAc (3×10 mL), dried over Na$_2$SO$_4$ and concentrated in vacuo. The crude was purified by column chromatography, on silica (hexane/EtOAc 1:1) to obtain fluoride 139 as a white solid (7.5 mg, 65% yield).
R$_f$ 0.22 (hexane/EtOAc 1:1);
$^1$H NMR (300 MHz, CDCl$_3$) δ 0.88 (t, 3H, J=7.0 Hz), 1.20–1.40 (m, 22H), 2.09 (q, 2H, J=6.9 Hz), 4.03–4.13 (m, 1H), 4.41 (dm, 2H, J=46.5 Hz), 5.11 (t, 1H, J=7.9 Hz), 5.44 (br s, 1H), 5.48 (dd, 1H, J=15.3, 8.1 Hz), 5.95 (dt, 1H, J=15.3, 7.0 Hz);
$^{13}$C NMR (75 MHz, CDCl$_3$) δ 14.1, 22.6, 28.6, 29.1, 29.3, 29.4, 29.5, 29.6, 31.9, 32.2, 55.3 (d), 79.0 (d), 81.8 (d), 121.4, 139.4, 159.3;
ESMS calcd for C$_{19}$H$_{34}$FNO$_2$Na (M+Na) 350.3, found 350.2.

Example 136

(2S,3R)-2-Amino-1-fluoro-octadec-4-en-3-ol, 140

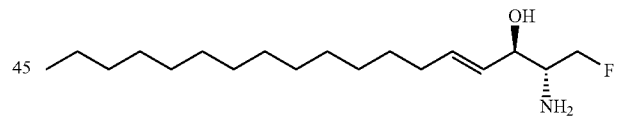

To a solution of 139 (46 mg, 0.140 mmol) in dioxane (2.5 mL), NaOH (1M, 1.40 mL, 1.405 mmol) was added. After stirring for 4 h at 100° C., the reaction was quenched with H$_2$O (10 mL), extracted with EtOAc (3×10 mL), dried over Na$_2$SO$_4$ and concentrated in vacuo. The crude was purified by column chromatography on silica (hexane/EtOAc 1:1 to 100% EtOAc) to obtain aminoalcohol 140 as a white solid (20 mg, 47% yield).
R$_f$ 0.18 (hexane/EtOAc 1:5);
$^1$H NMR (300 MHz, CDCl$_3$) δ 0.87 (t, 3H, J=6.2 Hz), 1.20–1.40 (m, 22H), 1.79 (br s, 3H), 2.05 (q, 2H, J=6.9 Hz), 3.03–3.13 (m, 1H), 4.05 (t, 1H, J=6.4 Hz), 4.40 (ddd, 1H, J=47.5, 9.2, 6.9 Hz), 4.51 (ddd, 1H, J=47.0, 9.2, 4.2 Hz), 5.44 (dd, 1H, J=15.6, 7.4 Hz), 5.76 (dt, 1H, J=15.4, 6.9 Hz);
$^{13}$C NMR (75 MHz, CDCl$_3$) δ 14.1, 22.7, 29.1, 29.2, 29.3, 29.4, 29.6, 29.6, 31.9, 32.3, 55.2 (d), 73.1 (d), 85.2 (d), 128.4, 135.2;
ESMS calcd for C$_{18}$H$_{37}$FNO (M+H) 302.3, found 302.2.

Example 137

(2S,3R)-2-Amino-1-fluoro-3-octadecanol, 141

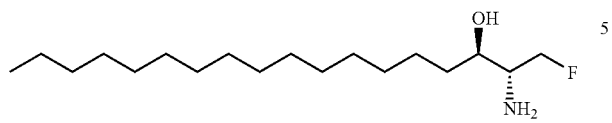

According to the method of Example 89, from olefin 140 (4 mg, 0.013 mmol), aminoalcohol 141 was obtained as a white solid (1.8 mg, 45% yield).

$^1$H NMR (300 MHz, CDCl$_3$) δ 0.87 (t, 3H, J=6.7 Hz), 1.20–1.40 (m, 26H), 1.50–1.60 (m, 2H), 1.87 (br s, 3H), 3.04–3.14 (m, 1H), 3.54–3.62 (m, 1H), 4.40 (ddd, 1H, J=48.0, 9.2, 7.4 Hz), 4.56 (ddd, 1H, J=46.8, 9.2, 3.9 Hz);

$^{13}$C NMR (75 MHz, CDCl$_3$) δ 14.1, 22.7, 26.0, 29.3, 29.6, 29.7, 31.9, 32.9, 55.0 (d), 72.5 (d), 85.1 (d);

ESMS calcd for C$_{18}$H$_{39}$FNO (M+H) 304.3, found 304.3.

What is claimed is:

1. A compound of formula:

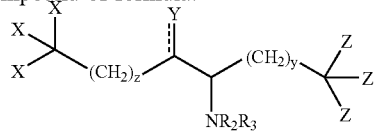

wherein:

the terminal group —C(X)$_3$ is CH$_3$;

Y is OR$_1$, wherein R$_1$ is selected from H, C(=O)R', P(=O)R'R", S(=O)R'R", substituted or unsubstituted C$_1$–C$_{18}$ alkyl, substituted or unsubstituted C$_2$–C$_{18}$ alkenyl, substituted or unsubstituted C$_2$–C$_{18}$ alkynyl, or substituted or unsubstituted aryl and wherein the dotted line indicates an optional double bond such that Y can also be =O; or the group Y with NR$_2$R$_3$ and the intervening atoms can form a heterocycle;

the terminal group —C(Z)$_3$ is CH$_3$;

z is 11 to 19;

y is 1 to 3, wherein when y is 2, then z is not 14;

R$_2$ and R$_3$ are the same or different and each is H, C(=O)R', C(=S)R', P(=O)R'R", S(=O)R'R", S(=O)$_2$R', substituted or unsubstituted C$_1$–C$_{18}$ alkyl, substituted or unsubstituted C$_2$–C$_{18}$ alkenyl, substituted or unsubstituted C$_2$–C$_{18}$ alkynyl, substituted or unsubstituted aryl;

each of the R', R" groups is independently selected from the group consisting of H, OH, NO$_2$, NH$_2$, NHR', NR'R", SH, CN, halogen, =O, C(=O)H, C(=O)CH$_3$, CO$_2$H, CO$_2$CH$_3$, substituted or unsubstituted C$_1$–C$_{18}$ alkyl, substituted or unsubstituted C$_1$–C$_{18}$ alkoxy, substituted or unsubstituted C$_2$–C$_{18}$ alkenyl, substituted or unsubstituted C$_2$–C$_{18}$ alkynyl, substituted or unsubstituted aryl; and salts thereof.

2. A compound or salt according to claim 1, wherein Y is OH, O(C=O)R' where R' is optionally halogen-substituted alkyl, OP(=O)R'$_2$ where R' is alkoxy, NH$_2$, =O, =NOH, or the group Y when OH with NR$_2$ R$_3$ and the intervening atoms form a heterocycle of formula:

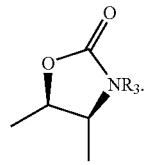

3. A compound or salt according to claim 1, wherein R$_2$ and R$_3$ are the same.

4. A compound or salt according to claim 1, wherein at least one of R$_2$ and R$_3$ is alkyl; alkyl substituted by aryl; hydrogen; C (=O)R' where R' is alkyl or alkoxy, halogen-substituted alkyl, optionally substituted amino-substitued alkyl; aryloxy, alkoxy, optionally substituted aryl-substituted alkenyl; (C=S)NHR' where R' is aryl; (C=O)NHR' where R' is aryl or alkyl; SO$_2$R' where R' is alkyl, or (C=O)R' where R' is optionally substituted aminoalkyl thereby giving an optionally substituted aminoacid acyl group.

5. A compound or salt according to claim 1, which has the stereochemistry

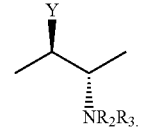

6. A compound or salt according to claim 1, wherein two or more of the following criteria are met:

Y is OR$_1$ where R$_1$ is H, methyl, acetyl, PO(OMe)$_2$, or COCF$_3$; or Y is =O;

R$_2$ and R$_3$ are independently selected from the group consisting of H, methyl, acetyl, benzyl, Boc, CSNHPh, CONHPh, CONH"Bu, SO$_2$Me, COCF$_3$, COCH=CHPh, COCH=CHPhCF$_3$, COC$_{15}$H$_{32}$, COCH(NHBoc)CHMe$_2$, COCH(NH$_3^+$Cl$^-$)CHMe$_2$;

the stereochemistry is

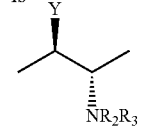

or the compound or salt is in the form of a salt.

7. A compound or salt according to claim 6, which meets one of the following criteria:

z is not 12, 13 or 14; or

Y is not OH; or

At least one of R$_2$ and R$_3$ is not hydrogen;

the compound or salt is in the form of a salt.

8. A compound or salt according to claim 1, which is of the formula:

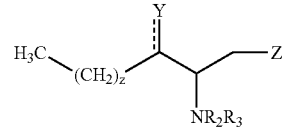

where z is 11 to 19;

Y is OR$_1$ where R$_1$ is H, methyl, acetyl, PO(OMe)$_2$, or COCF$_3$; or Y is =O;

R$_2$ and R$_3$ are independently selected from the group consisting of H, methyl, acetyl, benzyl, Boc, CSNHPh, CONHPh, CONHnBu, SO$_2$Me, COCF$_3$, COCH=CHPh, COCH=CHPhCF₃, COC₁₅H₃₂, COCH(NHBoc)CHMe₂, COCH (NH₃⁺Cl⁻)CHMe₂;

Z represents methyl or ethyl.

9. A compound or salt according to claim 1, which is one of the following compounds:

54
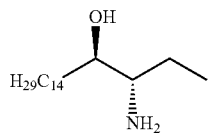

55
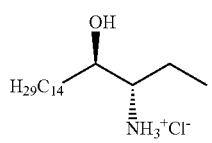

57
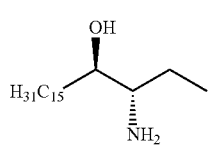

58
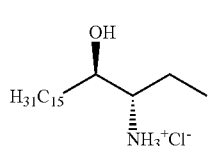

60
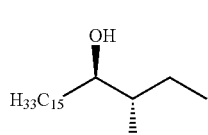

61
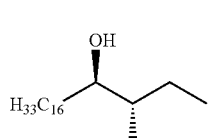

63
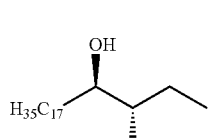

64
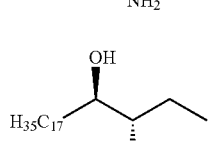

93
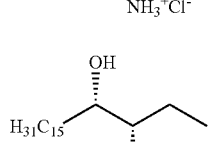

102
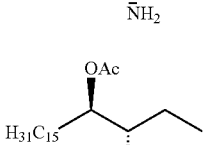

133
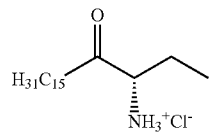

10. A pharmaceutical composition comprising a compound of formula:

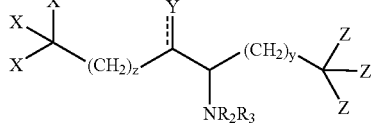

wherein:
the terminal group $-C(X)_3$ is $-CH_3$;
Y is $OR_1$, wherein $R_1$ is selected from H, C(=O)R', P(=O)R'R'', S(=O)R'R'', substituted or unsubstituted $C_1-C_{18}$ alkyl, substituted or unsubstituted $C_2-C_{18}$ alkenyl, substituted or unsubstituted $C_2-C_{18}$ alkynyl, or substituted or unsubstituted aryl and wherein the dotted line indicates an optional double bond such that Y can also be =O; or the group Y with $NR_2R_3$ and the intervening atoms can form a heterocycle;
the terminal group $-C(Z)_3$ is $CH_3$;
z is 10 to 19;
y is 1 to 3;
$R_2$ and $R_3$ are the same or different and each is H, C(=O)R', C(=S)R', P(=O)R'R'', S(=O)R'R'', S(=O)₂R', substituted or unsubstituted $C_1-C_{18}$ alkyl, substituted or unsubstituted $C_2-C_{18}$ alkenyl, substituted or unsubstituted $C_2-C_{18}$ alkynyl, substituted or unsubstituted aryl;
each of the R', R'' groups is independently selected from the group consisting of H, OH, NO₂, NH₂, NHR', NR'R'', SH, CN, halogen, =O, C(=O)H, C(=O)CH₃, CO₂H, CO₂CH₃, substituted or unsubstituted $C_1-C_{18}$ alkyl, substituted or unsubstituted $C_1-C_{18}$ alkoxy, substituted or unsubstituted $C_2-C_{18}$ alkenyl, substituted or unsubstituted $C_2-C_{18}$ alkynyl, substituted or unsubstituted aryl; and salts thereof, together with a pharmaceutically acceptable carrier.

11. A method of treating a tumor which includes administration of an effective amount of a compound of formula:

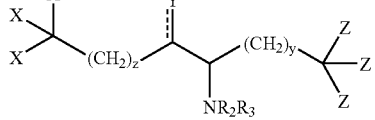

wherein:
the terminal group $-C(X)_3$ is $-CH_3$;
Y is $OR_1$, wherein $R_1$ is selected from H, C(=O)R', P(=O)R'R'', S(=O)R'R'', substituted or unsubstituted $C_1-C_{18}$ alkyl, substituted or unsubstituted $C_2-C_{18}$ alkenyl, substituted or unsubstituted $C_2-C_{18}$ alkynyl, or substituted or unsubstituted aryl and wherein the dotted line indicates an optional double bond such that Y can also be =O; or the group Y with $NR_2R_3$ and the intervening atoms can form a heterocycle;
the terminal group $-C(Z)_3$ is $CH_3$;
z is 10 to 19;
y is 1 to 3;

$R_2$ and $R_3$ are the same or different and each is H, C(=O)R', C(=S)R', P(=O)R'R", S(=O)R'R", S(=O)$_2$R', substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl;

each of the R', R" groups is independently selected from the group consisting of H, OH, $NO_2$, $NH_2$, NHR', NR'R", SH, CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_1$–$C_{18}$ alkoxy, substituted or unsubstituted $C_2$–$C_{18}$ alkenyl, substituted or unsubstituted $C_2$–$C_{18}$ alkynyl, substituted or unsubstituted aryl; and salts thereof, or a pharmaceutical composition thereof.

12. The compound or salt of claim 1, wherein Y is $OR_1$, wherein $R_1$ is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl and wherein the dotted line indicates an optional double bond such that Y can also be =O.

13. The compound or salt of claim 1, wherein wherein Y is OH, O(C=O)R' where R' is optionally halogen-substituted alkyl, OP(=O)R'$_2$ where R' is alkoxy, $NH_2$, =O, =NOH.

* * * * *

UNITED STATES PATENT AND TRADEMARK OFFICE
CERTIFICATE OF CORRECTION

PATENT NO. : 7,138,547 B2  Page 1 of 1
APPLICATION NO. : 10/297352
DATED : November 21, 2006
INVENTOR(S) : Javier Adrio et al.

It is certified that error appears in the above-identified patent and that said Letters Patent is hereby corrected as shown below:

Column 2, line 30, delete "$C_2$-$C_{18}$ynyl", insert -- $C_2$-$C_{18}$alkynyl --

Column 4, line 16, delete "alksulfinyl", insert -- alkylsulfinyl --

Column 113, lines 26-30, claim 9, the structure of compound 60:

Delete " 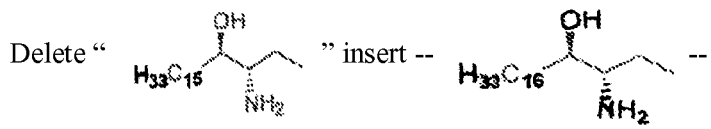 " insert --

Column 13, lines 50-55, the structure of compound 112:

Delete " 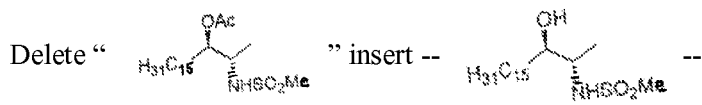 " insert --

Signed and Sealed this

Twenty-seventh Day of May, 2008

JON W. DUDAS
*Director of the United States Patent and Trademark Office*